United States Patent
Mithen

(10) Patent No.: US 6,977,297 B1
(45) Date of Patent: Dec. 20, 2005

(54) METHODS AND MEANS FOR MODIFICATION OF GLUCOSINOLATES IN PLANTS

(75) Inventor: Richard F. Mithen, Norwich (GB)

(73) Assignee: Plant Bioscience Limited, Norwich (GB)

( * ) Notice: Subject to any disclaimer, the term of this patent is extended or adjusted under 35 U.S.C. 154(b) by 0 days.

(21) Appl. No.: 09/554,761

(22) PCT Filed: Nov. 23, 1998

(86) PCT No.: PCT/GB98/03525

§ 371 (c)(1),
(2), (4) Date: May 19, 2000

(87) PCT Pub. No.: WO99/27120

PCT Pub. Date: Jun. 3, 1999

(30) Foreign Application Priority Data

Nov. 21, 1997 (GB) .............................. 9724691

(51) Int. Cl.[7] ........................ C12N 15/29; C12N 15/52; C12N 15/64; C12N 15/82
(52) U.S. Cl. .................... 536/23.6; 536/23.1; 536/23.2; 435/252.3; 435/320.1; 435/419; 435/465; 800/278; 800/298
(58) Field of Search ................................ 800/278, 286, 800/298, 285; 435/419, 320.1, 465; 536/23.1, 23.2, 23.6

(56) References Cited

FOREIGN PATENT DOCUMENTS

WO        97 16559 A    5/1997

OTHER PUBLICATIONS

GenBank Accession No. D38015 Submitted Aug. 19, 1994.*
By Koucji et al., Mol. Plant Microb. Interact. 1995, vol. 8; pp. 172–176 GenBank Accession No. D38015.*
Broun P. et al. Science vol. 282; Nov. 13, 1998, pp. 1315–1317.*
Crete P. et al. Plant Mol Biol Sep. 1999; 41(1):105–114.*
van der Krol A. et al., Plant Molecular Biology, 1990; vol. 14: 457–466.*
Robbins M. et al. Plant Physiol., 1998; vol. 116: 1133–1144.*
Chavadej S. et al. PNAS, Mar. 1994, vol. 91; pp. 2166–2170.*
Magrath, R., et al.: "Genetics of Aliphatic Glucosinolates. I. Side Elongation in *Brassica napus* and *Arabidopsis thaliana*" HEREDITY, vol. 72, 1994, pp. 290–299.
Kotani, H., et al.: "Structural Analysis of *Arabidopsis thaliana* Chromosome 5. II. Sequence Features of the Regions of 1, 044, 062bp covered by thirteen physically asigned P1 clones" EMBL Sequence Data Library, Sep. 1997, heidelberg, Germany accession No. AB006708.
Toroser, D., et al.: "RFLP Mapping of Quantitative Trait Loci Controlling Seed Aliphatic–Glucosinolate Content in Oilseed Rape (*Brassica napus* L.)" Theor. Appl. Genet., vol. 91, 1995, pp. 802–808.
Giamoustraris, A. and Mithen, R.: "Genetics of Aliphatic Glucosinolates. IV. Side–Chain Modificatior *Brassica oleracea*" Theor. Appl. Genet., vol. 93, 1996, pp. 1006–1010.
Kouchi, H. and Hata, S.: "GmN56, a Novel Nodule–Specific cDNA from Soybean Root Nodules Encodes Protein Homologous to Isopropylmalate Synthase and Homocitrate Synthase" Molecular Plant–Microbe Interactions, vol. 8, No. 1, 1995, pp. 172–176.
Haughn, G.W., et al.: "Biochemical Genetics of Plant Secondary Metabolites in *Arabidopsis thaliana*" Plant Physiology, vol. 97, 1991, pp. 217–226.
Love H K et al.: "Development of Low Glucosinolate Mustard" Canadian Journal of Plant Science, vol. 70 No. 2, Apr. 1990, pp. 419–424.

* cited by examiner

*Primary Examiner*—Phuong T. Bui
*Assistant Examiner*—Russell Kallis
(74) *Attorney, Agent, or Firm*—Nixon & Vanderhye P.C.

(57) ABSTRACT

GSL-ELONGASE gene of *Arabidopsis thaliana* and other plants, especially *Brassica oleracea, Brassica rapa* and *Brassica napus*. The nature and level of glucosinolates in plants can be modified by transgenic expression of the genes or control of the level of expression.

17 Claims, 25 Drawing Sheets

Fig. 5

```
004974    MASITANHPI  SGKPLISFRP  KNPLLQTQTL  PNFKPSISKH   40
Q39891    ..........  ..........  ..MPTKTSTP              8
Aaseq     ..MVLRSGLP  IGSSFPSLRL  TRPYDKATLF  VSCCSAESKK   38
Q01181    ..........  ..........  ..........  ..........    0
Consensus ----------  ----------  ----------  -------S--   40

004974    SNSSFSIPVV  RCSIRRIPEY  TPSHIPDPNY  VRIF..DTTL   78
Q39891    SSQSPKLSHL  R......PQY  IPNHIPDSSY  VRIL..DTTL   40
Aaseq     VATSA..TDL  KPIMERRPEY  IPNKLPHKNY  VRVL..DTTL   74
Q01181    ..........  ....MSRQQP  R SFLPESPL  APVALCDTTL   26
Consensus ---S------  -------P-Y  -P---P---Y  VR----DTTL   80

004974    RDGEQSPGAT  MTKEKLDVA   RQSAKLGVDI  IEAGFPASSE  118
Q39891    RDGEQSPGAT  MTAKEKLDIA  RQLVKLGVDI  IQPGFPSASN   80
Aaseq     RDGEQSPGAA  LTPPQKLEIA  RQLAKLRVDI  MEVGFPVSSE  114
Q01181    RDGEQTAGVA  FTRAERRAIA  EALQAAGVAE  VEVGVPAHGE   66
Consensus RDGEQSPGA-  -T---EKL-IA ROL--KLGVDI -E-GFP--SE  120
                        ——— Region 1 ———

004974    ADLEAVKLIA  KEVGNGVYEE  .EYVPVICGL  ARCNKKDIDK  157
Q39891    SDFMAVKMIA  QEVGNAVDDD  .GYVPVIAGF  CRCVEKDIST  119
Aaseq     EEFEAIKTIA  KTVGNEVDEE  TGYVPVICGI  ARCKKRDIEA  154
Q01181    EERADIRAVA  AVLKTA....  ......APV   VWCRLRAEDL   95
Consensus ----A-K-IA  --VGN-V---  ---YVPVI-G- -RC---DI--  160

004974    AWEAVKYAKK  PRIHTFIATS  EVHMNYKLKM  SRDQVVEKAR  197
Q39891    AWEAVKYAKR  PRLCTSIATS  PIHMEHKLRK  SKDQVIQIAR  159
Aaseq     TWEALKYAKR  DRVMLFTSTS  EIHMKYKLKK  TKEEVIEMAV  194
Q01181    A..AQRTGV   VRLHIGVPVS  ERQISAKLGK  DAAWVRDKVE  133
Consensus AWEA-KYAK-  PR------TS  E-HM--KL-K  ----V---A-  200

004974    SMVAYARSIG  CEDVEFSPED  AGRSDPEFLY  HILGEVIKAG  237
Q39891    DMVKFARSLG  CNDIQFGAED  ATRSDREFLY  EILGVVIEAG  199
Aaseq     NSVKYAKSLG  FKDIQFGCED  GGRTEKDFIC  KILGESIKAG  234
Q01181    KLVR..AASWA GHKVSVGAED  ASRADPFFLA  EIAHVAAEAG  172
Consensus --V--A-S-G  --D--FG-ED  A-R-D---FL- -ILG--I-AG  240

004974    ATTLNIPDTV  GYTVPEEFGQ  LIAKIKANTP  GVEDVIISTH  277
Q39891    ATTVNIADTV  GIVMPLBLGK  LIVDIKDNTP  GIANVIISTH  239
Aaseq     ATTVGFADTV  GINMPQEFGE  LVAYVIENTP  GADDIVFAIH  274
Q01181    AIRFRISDTL  GVLDPFAAHE  LVGRVVTRCP  ....LPVEFH  208
Consensus ATT--I-DTV  G---P-E-G-  L------NTP  G--------H  280

004974    CQNDLGLSTA  NTLAGACAGA  RQLEVTINGI  GERAGNASLE  317
Q39891    CHNDLGLATA  NTIEGARTGA  RQLEVTINGI  GERAGNASLE  279
Aaseq     CHNDLGVATA  NTISGICAGA  RQVEVTINGI  GERSGNAPLE  314
Q01181    GHNDLGMATA  NSLAAARAGA  SHLSVTVNGL  GERAGNAALE  248
Consensus CHNDLG-ATA  NT--GA-AGA  RQLEVTINGI  GERAGNA-LE  320
                                    ——— Region 2 ———

004974    EVVHALKCRG  EQVLGGLYTG  INTQHILMSS  KMVEGISGLH  357
Q39891    EVVHALASKG  DHALNGLYTR  INTRHILETS  KMVEEYSGMH  319
Aaseq     EVVHALKCRG  ESLMDGVYTK  IDSRQIHATS  KMVQEHTGMY  354
Q01181    EVAAALEAAG  RA......TG  VALGQLCALS  ELVARASGRP  282
Consensus EVVHAL---G  -----G-YT-  I----I---S  KMV---SG--  360

004974    VQPHKAIVGA  NAFVHESGIH  QDGMLKHKDT  YEIISPEDIG  397
Q39891    LQPHKPLVGA  NAFVHASGIH  QDGMLKHKGT  YETISPEEIG  359
Aaseq     VQPHKPIVGD  NCFVHESGIH  ODGILKNRST  YEILSPEDVG  394
Q01181    LSPQKPIVGE  GVFTHECGIH  VDGLMKDRAT  YESADLRPER  322
Consensus -QPHKPIVG-  N-FVHESGIH  ODG-LK---T  YE--SPE--G  400
                      ——— Region 3 ———

004974    LNRANESGIV  FGKLSGVMLC  KPKMLELGYE  IEGKELDDLF  437
Q39891    HKRTTRIGIV  LGKLSGSQAL  RKRLELGYD   LKEDEVDSVF  399
Aaseq     IVKSENSGIV  LGKLSGRHAV  KDRLKELGYE  ISDEKFNDIF  434
Q01181    FGRSHRIAI.  .GKHSSAAGL  ARALAEAGLP  ADAATLAALM  360
Consensus --R----GIV  -GKLSG----  ---L-ELGY-  ---------F  440

004974    WRFKSVAE.K  KKITDDDLV   ALHSDEVFQP  QFVWQLQNVQ  476
Q39891    WQFKAKME.K  KVVTDVDLK   ALVSYKAFHA  ESIWKLGDLQ  438
Aaseq     SRYRELTK.D  KKRITDADLK  ALV.......  ....VNGAE   461
Q01181    PALRDWAAIT  KRAAAPEDLA  ALLAAQTETA  R..........  391
Consensus ------A---  KK--TD-DL-  AL--------  ----------  480

004974    VTCGSLGLST  ATVKLIDADG  REHISCSVGT  GPVDAAYKAV  516
Q39891    VTCGTIGLST  ATVKLVNIDG  STHVACSIGI  GAVDSTYKAI  478
Aaseq     ISSEKL....  ......NSKG  INDLHSSPQI  SAVV.......  485
Q01181    ..........  ..........  ..........  ..........  391
Consensus ----------  --------G   -----S---  --V-------  520
```

Fig. 6A

```
gsl-elong_s  MASSLLTSSV MIPTTGSTVV GRSVLPFQSS LHSLRLTHSY 40
     aaseq  MASLLLTSSS MITTSCPSMV LRSGLPIGSS FPSLRLTRPY 40
    o04974  .......... ......MASI TANHPISGKP LISFRPKNPL 24
    q39891  .......... .......... .......... ..........  0
    q01181  .......... .......... .......... ..........  0
 Consensus  MAS-LLTSS- MI-T-----V -RS-LP-GSS L-SLRLT-PY 40 gsl-elong_s  KNPALFISCC SSVSKNAATS S..TDLKPVV ERWPEYIPNK 78
     aaseq  DKATLFVSCC SAESKKVATS A..TDLKPIM ERRPEYIPNK 78
    o04974  LQTQTLFNFK PSISKHSNSS FSIPVVRCSI RRIPEYTPSH 64
    q39891  ........MP TKTSTPSSQS PKLSHLR... ...PQYIPNH 26
    q01181  .......... .......... ....MSRQ QPRASFLPES 14
 Consensus  ----LF-SCC SS-SK-SATS ---TDL-P-- ERRPEYIPN- 80 gsl-elong_s  LPDGNYVRVF DTTLRDGEQS PGGSLTPPQK LEIARQLAKL 118
     aaseq  LPHKNYVRVL DTTLRDGEQS PGAALTPPQK LEIARQLAKL 118
    o04974  IPDPNYVRIF DTTLRDGEQS PGATMTTKEK LDVARQSAKL 104
    q39891  IPDSSYVRIL DTTLRDGEQS PGATMTAKEK LDIAROLVKL 66
    q01181  PLAP..VALC DTTLRDGEQT AGVAFTRAEK RAIAEALQAA 52
 Consensus  -PDPNYVR-- DTTLRDGEQS PGA--TP-EK L-IARQLAKL 120 gsl-elong_s  RVDIMEVGFP GSSEEELETI KTIAKTVGNE VDEETGYVPV 158
     aaseq  RVDIMEVGFP VSSEEFEAI KTIAKTVGNE VDEETGYVPV 158
    o04974  GVDIIEAGFP ASSEADLEAV KLIAKEVGNG VYEE.EYVPV 143
    q39891  GVDIIQPGFP SASNSDFMAV KMIAQEVGNA VDDD.GYVPV 105
    q01181  GVAEVEVGVP AMGEEERADI RAVAAVLKTA .......... 82
 Consensus  GVDI-EVGFP ASSEEE-EAI KTIAK-VGN- VDEETGYVPV 160 gsl-elong_s  ICAIARCKHR DIEATWEALK YAKRPRILVF TSTSDIHMKY 198
     aaseq  ICGIARCKKR DIEATWEALK YAKRPVMLF TSTSEIHMKY 198
    o04974  ICGLARCNKK DIDKAWEAVK YAKKPRIHTF IATSEVHMNY 183
    q39891  IAGFCRCVEK DISTAWEAVK YAKRPRLCTS IATSPIHMEH 145
    q01181  .APVVWCRLR AED..LAAAQ RTGVVRLHIG VPVSERQISA 119
 Consensus  ICGIARCKKR DI-A-WEA-K YAKRPR-HTF --TSEIHMKY 200 gsl-elong_s  KLKKTQEEVI EMAVSIRFA KSLGFNDIQF GCEDGGRSDK 238
     aaseq  KLKKTKEEVI EMAVNSVKYA RSIGCEDVEF GCEDGGRTEK 238
    o04974  KLKMSRDQVV EKARSMVAYA RSIGCEDVEF SPEDAGRSDP 223
    q39891  KLRKSKDQVI QIARDMVKFA RSLGCNDIOF GAEDATRSDR 185
    q01181  KLGKDAAWVR DKVEKLVR.A ASWAGHKVSV GAEDASRADP 158
 Consensus  KLKK-K--VI E-A-S-V--A -SLG-NDIQF G-EDAGRSD- 240 gsl-elong_s  DFICKILGEA IKAGVTVVTI GDTVGINMPH EYGELVTYLK 278
     aaseq  DFICKILGES IKAGATTVGF ADTVGINMPQ EFGELVAYVI 278
    o04974  EFYHILGEV IKAGATTLNI PDTVGYTVPE BFGQLIAKIK 263
    q39891  EFLYEILGVV IEAGATTVNI ADTVGIVMPL ELGKLIVDIK 225
    q01181  FPLAEIHVA AEAGAIRFRI SDTLGVLDPF AAHELVGRVV 198
 Consensus  -FI--ILGE- IKAGATTVNI ADTVGINMP- EFGELVAY-K 280 gsl-elong_s  ANTPGIDDV VAVHCHNDLG LATANSIAGI RAGAROVEVT 318
     aaseq  ENTPGADDIV FAIHCHNDLG VATANTISGI CAGAROVEVT 318
    o04974  ANTPGVEDVI ISTHCQNDLG LSTANTLAGA CAGAROLEVT 303
    q39891  DNTPGIANVI ISTHCHNDLG LATANTIEGA RTGAROLEVT 265
    q01181  TRCP....LP VEFHGHNDLG MATANSLAAA RAGASHLSVT 234
 Consensus  ANTPGIDDV- --THCHNDLG LATANTIAGA RAGAROLEVT 320 gsl-elong_s  INGIGERSGN ASLEEVVMAL KCRGAYVING VYTKIDTRQI 358
     aaseq  INGIGERSGN APLEEVVMAL KCRGESLMDG VYTKIDSROI 358
    o04974  INGIGERAGN ASLEEVVMAL KCRGEQVLGG LYTGINTQHI 343
    q39891  INGIGERAGN ASLEEVVMAL ASKGDHALNG LYTRINTRHI 305
    q01181  VNGLGERAGN AALEEVAAAL EAAGRA.... ..TGVALGQL 268
 Consensus  INGIGERAGN ASLEEVVMAL KCRGE-VLNG -YT-I-TROI 360
```

Fig. 6B

```
gsl-elong_s  MATSKMVQEY  TGLYVQAHKP  IVGANCFVHE  SGIHQ..VRN  396
      aaseq  MATSKMVQEH  TGMYVQPHKP  IVGDNCFVHE  SGIHQDGILK  398
     o04974  LMSSKMVEGI  SGLHVQPHKA  IVGANAFVHE  SGIHQDGMLK  383
     q39891  LETSKMVEEY  SGMHLQPHKP  LVGANAFVHA  SGIHODGNLK  345
     q01181  CALSELVARA  SGRPLSPQKP  IVGEGVFTHE  CGIHVDGLMK  308
  Consensus  -ATSKMV-EY  SG--VQPHKP  IVGAN-FVHE  SGIHQDGMLK  400 gsl-elong_s  WWSTYEILSP  EDIGIVKSQN  SGLVLGKLSG  RHAVKDRLKE  436
      aaseq  NRSTYEILSP  EDVGIVKSEN  SGIVLGKLSG  RHAVKDRLKE  438
     o04974  HKDTYEIISP  EDIGLNRANE  SGIVFGKLSG  VMLCKPKMLE  423
     q39891  HKGTYETISP  FEIGHKRTTR  IGIVLGKLSG  SQALRKRLEE  385
     q01181  DRATYESADL  RPERFGRSHR  IAI..GKHSS  AAGLARALAE  346
  Consensus  H-STYEI-SP  EDIGIVRS--  SGIVLGKLSG  RHA-KDRLKE  440 gsl-elong_s  LGYELDDEKL  NAVFSLFRDL  TKNKKRITD.  ADLKALV...  472
      aaseq  LGYEISDEKF  NDIFSRYREL  TKDKKRITD.  ADLKALV...  474
     o04974  LGYEIEGKEL  DDLFWRFKSV  AEKKKKITD.  DDLVALMSDE  462
     q39891  LGYDLKEDEV  DSVFWQFKAM  AEKKKVVTD.  VDLKALVSYK  424
     q01181  AGLPADAATL  AALMPALRDW  AAITKRAAAE  EDLAALLAAQ  386
  Consensus  LGYE-DDE-L  ---F-RFRDL  A-KKKRITDP  ADLKALVS--  480 gsl-elong_s  .........T  SSDEISLEKL  N.GANGLKSN  GYIPVPQVSS  502
      aaseq  .........V  NGAEISSEKL  N.SKG...IN  DLMSSPQISA  501
     o04974  VFQPQFVMQL  QNVQVTCGSL  GLSTATVKLI  DADGREHISC  502
     q39891  AFHAESIWKL  GDLQVTCGTI  GLSTATVKLV  NIDGSTHVAC  464
     q01181  TETAR.....  ..........  ..........  ..........  391
  Consensus  -F-A---M-L  ------C-KL  -LSTATVKLN  D-DGSP--SC  520 gsl-elong_s  NV........  ..........  ..........  ..........  504
      aaseq  VV........  ..........  ..........  ..........  503
     o04974  SVGTGPVDAA  YKAVDLIVKV  PVTLIEYSMN  AVTQGIDAIA  542
     q39891  SIGIGAVDST  YKAINLIVKE  PTKLLDYSLN  SVTEGIGVNV  504
     q01181  ..........  ..........  ..........  ..........  391
  Consensus  SVG-G-VD--  YKA--LIVK-  P--LL-YS-N  -VT-GI----  560 gsl-elong_s  ..........  ..........  ..........  ..........  504
      aaseq  ..........  ..........  ..........  ..........  503
     o04974  STRVLIRGEN  GHTSTHALTG  ETVHRTFSGT  GADMDIVISS  582
     q39891  TARVVICREN  NHTSTYAFTE  DANYPTFSGI  AAEMDVVVST  544
     q01181  ..........  ..........  ..........  ..........  391
  Consensus  --RV-I--EN  -HTST-A-T-  -----TFSG-  -A-MD-V-S-  600 gsl-elong_s  ..........  ..........  ..........          504
      aaseq  ..........  ..........  ..........          503
     o04974  VRAYVGALNK  MMSFRKLMAK  NNKPESSAVI          612
     q39891  VKAYLVALNK  LLRWKESFRC  A.........          565
     q01181  ..........  ..........  ..........          391
  Consensus  V-AY--ALNK  ----------  -NKPESSAVI          630
```

Fig. 8A

```
GCTGAGTTTC AATGGTTTTT GATAATGTGA TGAGAGTTTA GAACTGGAAG
AAGTTATACT TACTCTCATA AGAATAATGA TTAGGATTAC ATAGGTTTAT
ATAGTAAAGA GATTTCATAA ACTAGATGAA TACAAATATG TAAAATATCT
TATATCATAA CTATACAATA TTTGATTATA TATTGAGAAT CTTCTAGATA
CTTCCATACC CTTCTATAGT TTTAACTCAA AAATCAATTG GCAATTGGAT
TTAAAGAATA TAATGTGGGA TTCCATTACA CTTACGATGG ATTTGCTCAA
AAAAAGAAAA AAGAAAGAAA GATTCCATTA CATTTAGGAT GTGAGATTCG
TAACACGATT CAAAATAATA GCTAAGACCT TTTATCTTAC CGAATTCCCT
TTTAAAACTG CAATACCC TACTTGGATC ACCCTAAACT AAAGTCTAAA
CTATCATTTT ATGGTTATAA ACTTAATTAA AACCAACTGA CAATGAATTG
AAAAAATAAT GTGAGATTCC AAACATTATT TAATTTTTGG TTGTAAAATC
CCAAAAGGTA TATTTACCGC CTTTAAAAAA AACTAATGAA AGCAATTTAA
ATTGTTTCTG TGTATTCTCA TCATTTCCCG TCACTTTTGT AACAATTCCA
ACGTTAGAAC GATCATTCAC TCGCGTAAAT TGTTTTTATT TTATTTTAAA
GCGTTTTAAA CCATAACATA AAAAAGTTTA AGGATATTAT AATTTTTTAT
CAAAAATTAA TGATATTAGG TTATCAAGTG GTCGAGTAAA TCATCTGGTT
ATATAAAATT GGAGAAAAAG ATTTCTACC TATATAAATA TAGATATCAT
CTGTACATGC ACTCCACCTC ATTGCAAAAC AATTTCCCCA CTATCTATCC
TCCATAATAT AGTATTCTTC TTTTCTCTCC TACTTTCTCT ATAGTAATGG
CTTCGTTACT TCTCACATCG TCGAGTATGA TAACCACTAG CTGTCGCTCC
ATGGTTCTCC GGTCAGGGTT ACCCATCGGA TCTTCTTTTC CCTCTCTTCG
CCTGACCCGT CCATACGACA AGGCGACTCT GTTCGTCTCA TGTTGCTCCG
CTGAGTCCAA AAAGGTGGCA ACTAGTGCTA CTGATCTCAA ACCTATCATG
GAACGGAGGC CGGAGTACAT TCCGAACAAG CTTCCCCACA AGAACTATGT
GCGTGTATTA GACACGACGC TTCGTGACGG TGAACAATCT CCCGGTGCAG
CACTTACTCC ACCGCAGAAG TTAGAGATTG CCAGGCAGCT AGCTAAACTC
CGAGTAGACA TCATGGAAGT TGGTTTTCCG GTGTCGTCTG AGGAAGAATT
CGAAGCTATT AAAACCATCG CCAAGACCGT GGGGAACGAG GTTAGTTTCT
TTATTTCCCT CACTTCAAGA AAATAATATA ATGATTTATG TTCAAACTAT
ATATAGATAT AATAAAATTA GATGTGCAAA GTGTTAGTTA AAGAATCTCA
CATTAGAAAT AAGAAGTAAT AATCTATACT AGCATTTAAA AAATATGGGC
CAATCTACTC ACTAATAAAT GATTTTTTTT TAACTTGGAA GCTCATGAAT
GCTTACAGAA AATTACAAAC ACATATTTAG TAATTGTCCA AAATTGACAG
GAACGAAAAT AAACTACTAT ATATTGCTGT TTTCCTTAGG TGGATGAGGA
AACCGGTTAC GTTCCTGTGA TATGCGGCAT TGCACGATGC AAAAAGAGAG
ACATCGAGGC AACTTGGGAG GCACTGAAGT ATGCAAGAG GCCGAGGGTA
ATGCTATTCA CATCTACTAG TGAAATTCAC ATGAAATATA AGTTGAAAAA
GACTAAAGAA GAAGTGATCG AGATGGCCGT GAACAGTGTT AAGTACGCTA
AAAGCTTGGG CTTCAAAGAC ATCCAATTTG GGTGCGAAGA TGGCGGCAGG
TATCTTGAAA CTTAGTATAA CTCGATTGTT CTTTTTTTCC GGCCACTAGG
TTTAACGTTA CAAAATCTTT GTTAGTAAAC TTACTTTTT TTTTTAATTA
CGTACGTTTA TCTTTTACAA GAATATTGAA AATGTTTTGA TTAATTTTTT
TTTGTTTTAT AAAACAATAT TTACATGCAA ACACAAAAGC ATAAATTCAA
CGCTGAAATA ATATATCTCA TAATCTAAAA CGCTTTTAGC TGATTTGTTT
```

Fig. 8B

TGTGAAATTT AAAATTTTGT TTTTTGAAAG TTGTTTTTAT ATAAGGTATG
AGAATGAAAA ATATAAGGGT GTGCCTTATA CAGTTATCTG GCCCAGTTTT
GATCATGTCA TATATAGATT TTATAGTATA CTAGTTTGTG ATTCAGGACG
GAGAAAGATT TTATATGTAA GATTCTAGGA GAATCGATAA AAGCGGGTGC
AACCACGGTG GGGTTTGCGG ACACGGTCGG GATCAACATG CCGCAAGAAT
TCGGAGAACT CGTGGCCTAT GTCATAGAAA ACACTCCAGG GGCTGATGAT
ATTGTCTTCG CCATTCATTG TCATAACGAC CTTGGTGTTG CTACCGCCAA
CACAATATCC GTACGTAATT GCTCTCCCTT TGTCTGAGTT AGATTAATCA
ACAAAAATTC CGAACAAATT TAAATTATCG AGGTGACAAG ATTATAAATA
TAAAACAATG ATATGTATAG GGTATATGTG CGGGAGCAAG ACAAGTCGAA
GTGACGATCA ACGGAATTGG TGAAAGAAGT GGGAATGCGC CGCTTGAAGA
GGTAAGATCG TCGTCGTGAG TATTTCTTTG GTATGTGTCG GCAGGGTATG
GTAAAGCAAA AAATTTAGAA GTGTGGTCTT ACACTTCTCT ACTAATTTTA
TCATAATTTA AAAGACTAAA AAAAAGTTGT CGTAAAACTA AAGTAAAACC
ACATAAACGG TACGGCTAGC TAGTAAATTA TTTAATAGTA ACGCCATAAA
AGTATAAATA TAATAATTTA ACATTACAAT AAGACCAACA TTACAATCTA
GAAGCGTTTA TGTGTTAAAA AAAAAAAAAA AAAATTACA ATCTAGAAGT
AGGCTACAAT GGAATTGACA TCAGGAAAGA GAGGAATTGG AATCGAATGC
TTCACGTAAC CCTTACATTA AGTATTTCAA ACGATAGCCA CCAAAAAGTT
ATGTAATGTG ACCCTAAAT TGCGTATTTA AATTGTGGAC TAGACGTACA
TGCTTCATGT GCTTTATGAA AAGACTGGTT CTGTGATTGT ATGTAGGTCG
TGATGGCTTT GAAATGTCGA GGAGAATCTC TGATGGATGG TGTTTACACA
AAAATAGACT CACGCCAAAT TATGGCTACA AGCAAGATGG TACGTAACAA
ACTAGATATT GAAATTTCGA TATTTATATG AAAACAATGA TGCTAATATT
TGGCCTTTAT ATATAATAAT TGACTAAAAC GTAAATTCTT GCGCAGGTTC
AAGAGCATAC CGGCATGTAT GTTCAACCAC ATAAGCCAAT AGTTGGAGAC
AACTGTTTTG TTCATGAGAG CGGCATTCAC CAGGTTCCAT ATATATATAT
ATATATATAT TACTTATGAA AATTGTATAT GAGATTGTTG CGTTGTATGT
GTATAATTGT CCAAACATTT TGCAGGATGG AATATTGAAA AATCGAAGTA
CATATGAGAT CTTATCACCA GAAGATGTTG GGATCGTAAA ATCTGAAAAT
TCTGGCATTG TTCTTGGAAA GCTTAGGTAA TTATTCTATT AAGTTATGTT
TCTTGGTTTT AGATAACTAT AAGTCTAAAA CTATGTACCA TCGTCTGATA
AATTTATTTC AACAACTATG AAAATATGCA GCGGACGTCA TGCTGTAAAA
GACCGGCTTA AAGAGGTACC ACACACACAC ACAGTATATA TTAGTGACTT
CGTACTATTT TTAGTCTTTA CTTATAATAA TCACACACAC ACATATATAT
GGGACCATGG CACAATAGAG ACTTTATAGA GATAAATATT TGATTAGTCA
TATGTTTTTT TTTTTTTTT GTAATCTCAA GTTGGGATAT GAAATCAGTG
ATGAGAAATT CAACGACATC TTCTCACGAT ACAGAGAATT AACGAAGGAC
AAAAAGGTTT TCATATTATA TTTTGTATCT TCTCATTTAC ATATGCGTCA
AATTTGAAAT ATTTAGTTAT ACATAAAATA CGAATAGATT TATAAAATTC
TACCAAACAT ATAAACCCCC ATACTTACTT GATTTCAATT TGTTAAACTC
CACAGAGAAT CACAGACGCT GATCTGAAGG CATTAGTGGT GAACGGTGCT

Fig. 8C

```
GAAATCTCAT CAGAAAAATT AAACAGTAAA GGAATTAACG ACCTTATGTC
AAGCCCTCAG ATTTCCGCTG TTGTATAAGT TTGGGAAGAC ATTGTGTAAT
TTTGTACTAC GATGGTATTA AGTCACTTTT GTTTTACTGT GTTTTGTGTA
CTATATATAC GTACCTTTTG GTTTTTATGT TATCGTTGTA ATGAATAAAA
CAGTATTAAT AGGGAGTGTT TTTATTCTAT AATTAAACTC TCTTTTTTAT
AATGATTTTC ACCAAAGTAT TGGAAATTTA AACAAACATT ACCATATTCC
ATTGAAGATT CAACAAAGTA TTGTTCATTT TCAGTTGTGA TCATTATTCT
TCCTCACACT ACTGCATTAA ATTGTTAATC AAATGCTCCC GTCATGACAA
CTACTATAAT TTACTGTTAA CTAAGCATTA ATAAAATTTT GATCATCTAC
CGTTAAAATT ATAAAACATG AATTGCCTCA TCATAGTAAG AGTCGTATTT
TCTTTCAGGG GTGGTTGATA GCTATATTGT CGTTCTATAT GTGGGACAT
GTTACCCTAA ACGGAAAAGT ATTTG
```

Fig. 9

ATGGTTCTCC GGTCAGGGTT ACCCATCGGA TCTTCTTTTC CCTCTCTTCG
CCTGACCCGT CCATACGACA AGGCGACTCT GTTCGTCTCA TGTTGCTCCG
CTGAGTCCAA AAAGGTGGCA ACTAGTGCTA CTGATCTCAA ACCTATCATG
GAACGGAGGC CGGAGTACAT TCCGAACAAG CTTCCCCACA AGAACTATGT
GCGTGTATTA GACACGACGC TTCGTGACGG TGAACAATCT CCCGGTGCAG
CACTTACTCC ACCGCAGAAG TTAGAGATTG CCAGGCAGCT AGCTAAACTC
CGAGTAGACA TCATGGAAGT TGGTTTTCCG GTGTCGTCTG AGGAAGAATT
CGAAGCTATT AAAACCATCG CCAAGACCGT GGGGAACGAG GTGGATGAGG
AAACCGGTTA CGTTCCTGTG ATATGCGGCA TTGCACGATG CAAAAAGAGA
GACATCGAGG CAACTTGGGA GGCACTGAAG TATGCAAGA GGCCGAGGGT
AATGCTATTC ACATCTACTA GTGAAATTCA CATGAAATAT AAGTTGAAAA
AGACTAAAGA AGAAGTGATC GAGATGGCCG TGAACAGTGT TAAGTACGCT
AAAAGCTTGG GCTTCAAAGA CATCCAATTT GGGTGCGAAG ATGGCGGCAG
GACGGAGAAA GATTTTATAT GTAAGATTCT AGGAGAATCG ATAAAAGCGG
GTGCAACCAC GGTGGGGTTT GCGGACACGG TCGGGATCAA CATGCCGCAA
GAATTCGGAG AACTCGTGGC CTATGTCATA GAAAACACTC CAGGGGCTGA
TGATATTGTC TTCGCCATTC ATTGTCATAA CGACCTTGGT GTTGCTACCG
CCAACACAAT ATCCGGTATA TGTGCGGGAG CAAGACAAGT CGAAGTGACG
ATCAACGGAA TTGGTGAAAG AAGTGGGAAT GCGCCGCTTG AAGAGGTCGT
GATGGCTTTG AAATGTCGAG GAGAATCTCT GATGGATGGT GTTTACACAA
AAATAGACTC ACGCCAAATT ATGGCTACAA GCAAGATGGT TCAAGAGCAT
ACCGGCATGT ATGTTCAACC ACATAAGCCA ATAGTTGGAG ACAACTGTTT
TGTTCATGAG AGCGGCATTC ACCAGGATGG AATATTGAAA AATCGAAGTA
CATATGAGAT CTTATCACCA GAAGATGTTG GGATCGTAAA ATCTGAAAAT
TCTGGCATTG TTCTTGGAAA GCTTAGCGGA CGTCATGCTG TAAAAGACCG
GCTTAAAGAG TTGGGATATG AAATCAGTGA TGAGAATTC AACGACATCT
TCTCACGATA CAGAGAATTA ACGAAGGACA AAAAGAGAAT CACAGACGCT
GATCTGAAGG CATTAGTGGT GAACGGTGCT GAAATCTCAT CAGAAAAATT
AAACAGTAAA GGAATTAACG ACCTTATGTC AAGCCCTCAG ATTTCCGCTG
TTGTA

Fig. 10

MVLRSGLPIG SSFPSLRLTR PYDKATLFVS CCSAESKKVA TSATDLKPIM
ERRPEYIPNK LPHKNYVRVL DTTLRDGEQS PGAALTPPQK LEIARQLAKL
RVDIMEVGFP VSSEEEFEAI KTIAKTVGNE VDEETGYVPV ICGIARCKKR
DIEATWEALK YAKRPRVMLF TSTSEIHMKY KLKKTKEEVI EMAVNSVKYA
KSLGFKDIQF GCEDGGRTEK DFICKILGES IKAGATTVGF ADTVGINMPQ
EFGELVAYVI ENTPGADDIV FAIHCHNDLG VATANTISGI CAGARQVEVT
INGIGERSGN APLEEVVMAL KCRGESLMDG VYTKIDSRQI MATSKMVQEH
TGMYVQPHKP IVGDNCFVHE SGIHQDGILK NRSTYEILSP EDVGIVKSEN
SGIVLGKLSG RHAVKDRLKE LGYEISDEKF NDIFSRYREL TKDKKRITDA
DLKALVVNGA EISSEKLNSK GINDLMSSPQ ISAVV

Fig. 11

MASLLLTSSS MITTSCPSMV LRSGLPIGSS FPSLRLTRPY DKATLFVSCC
SAESKKVATS ATDLKPIMER RPEYIPNKLP HKNYVRVLDT TLRDGEQSPG
AALTPPQKLE IARQLAKLRV DIMEVGFPVS SEEEFEAIKT IAKTVGNEVD
EETGYVPVIC GIARCKKRDI EATWEALKYA KRPRVMLFTS TSEIHMKYKL
KKTKEEVIEM AVNSVKYAKS LGFKDIQFGC EDGGRTEKDF ICKILGESIK
AGATTVGFAD TVGINMPQEF GELVAYVIEN TPGADDIVFA IHCHNDLGVA
TANTISGICA GARQVEVTIN GIGERSGNAP LEEVVMALKC RGESLMDGVY
TKIDSRQIMA TSKMVQEHTG MYVQPHKPIV GDNCFVHESG IHQDGILKNR
STYEILSPED VGIVKSENSG IVLGKLSGRH AVKDRLKELG YEISDEKFND
IFSRYRELTK DKKRITDADL KALVVNGAEI SSEKLNSKGI NDLMSSPQIS
AVV

Fig. 12

ACCTCATTGC AAAGCAATTT CCCCACTATC TATCCTCCAT AATATAGTAT
TCCTCTTTTC TCTCCTACGT TCTCTATAGT AATGGCTTCG TTACTTCTCA
CATCTTCCAG TATGATAACC ACTAGCTGTC CCTCCATGGT TCTCCGGTCA
GGGTTACCCA TCGGATCTTC TTTTCCCTCT CTTCGCCTGA CCCGTCCATA
CGACAAGGCG ACTCTGTTCG TCTCATGTTG CTCCGCTGAG TCCAAAAGG
TGGCAACTAG TGCTACTGAT CTCAAACCTA TCATGGAACG GAGGCCGGAG
TACATTCCGA ACAAGCTTCC CCACAAGAAC TATGTGCGTG TATTAGACAC
GACGCTTCGT GACGGTGAAC AATCTCCGG TGCAGCACTT ACTCCACCGC
AGAAGTTAGA GATTGCCAGG CAGCTAGCTA AACTCCGAGT AGACATCATG
GAAGTTGGTT TTCCGGTGTC GTCTGAGGAA GAATTCGAAG CTATTAAAAC
CATCGCCAAG ACCGTGGGGA ACGAGGTGGA TGAGGAAACC GGTTACGTTC
CTGTGATATG CGGCATTGCA CGATGCAAAA AGAGAGACAT CGAGGCAACT
TGGGAGGCAC TGAAGTATGC GAAGAGGCCG AGGGTAATGC TATTCACATC
TACTAGTGAA ATTCACATGA AATATAAGTT GAAAAAGACT AAAGAAGAAG
TGATCGAGAT GGCCGTGAAC AGTGTTAAGT ACGCTAAAAG CTTGGGCTTC
AAAGACATCC AATTTGGGTG CGAAGATGGC GGCAGGACGG AGAAAGATTT
TATATGTAAG ATTCTAGGAG AATCGATAAA AGCGGGTGCA ACCACGGTGG
GGTTTGCGGA CACGGTCGGG ATCAACATGC CGCAAGAATT CGGAGAACTC
GTGGCCTATG TCATAGAAAA CACTCCAGGG GCTGATGATA TTGTCTTCGC
CATTCATTGT CATAACGACC TTGGTGTTGC TACCGCCAAC ACAATATCCG
GTATATGTGC GGGAGCAAGA CAAGTCGAAG TGACGATCAA CGGAATTGGT
GAAAGAAGTG GGAATGCGCC GCTTGAAGAG GTCGTGATGG CTTTGAAATG
TCGAGGAGAA TCTCTGATGG ATGGTGTTTA CACAAAAATA GACTCACGCC
AAATTATGGC TACAAGCAAG ATGGTTCAAG AGCATACCGG CATGTATGTT
CAACCACATA AGCCAATAGT TGGAGACAAC TGTTTTGTTC ATGAGAGCGG
CATTCACCAG GATGGAATAT TGAAAAATCG AAGTACATAT GAGATCTTAT
CACCAGAAGA TGTTGGGATC GTAAAATCTG AAAATTCTGG CATTGTTCTT
GGAAAGCTTA GCGGACGTCA TGCTGTAAAA GACCGGCTTA AGAGTTGGG
ATATGAAATC AGTGATGAGA AATTCAACGA CATCTTCTCA CGATACAGAG
AATTAACGAA GGACAAAAAG AGAATCACAG ACGCTGATCT GAAGGCATTA
GTGGTGAACG GTGCTGAAAT CTCATCAGAA AAATTAAACA GTAAAGGAAT
TAACGACCTT ATGTCAAGCC CTCAGATTTC CGCTGTTGTA

Fig. 13A

ACCTCATTGC AAAACAATTT CCCCACTATC TATCCTCCAT AATATAGTAT
TCCTCTTTTC TCTCCTACGT TCTCTATAGT AATGGCTTCG TTACTTCTCA
CATCTTCCAG TATGATAACC ACTAGCTGTC CCTCCATGGT TCTCCGGTCA
GGGTTACCCA TCGGATCTTC TTTTCCCTCT CTTCGCCTGA CCCGTCCATA
CGACAAGGCG ACTCTGTTCG TCTCATGTTG CTCCGCTGAG TCCAAAAAGG
TGGCAACTAG TGCTACTGAT CTCAAACCTA TCATGGAACG GAGGCCGGAG
TACATTCCGA ACAAGCTTCC CCACAAGAAC TATGTGCGTG TATTAGACAC
GACGCTTCGT GACGGTGAAC AATCTCCCGG TGCAGCACTT ACTCCACCGC
AGAAGTTAGA GATTGCCAGG CAGCTAGCTA AACTCCGAGT AGACATCATG
GAAGTTGGTT TTCCGGTGTC GTCTGAGGAA GAATTCGAAG CTATTAAAAC
CATCGCCAAG ACCGTGGGGA ACGAGGTTAG TTTCTTTATT TCCCTCACTT
CAAGAAAATA ATATAATGAT TTATGTTCAA ACTATATATA GATATAATAA
AATTAGATGT GCAAAGTGTT AGTTAAAGAA TCTCACATTA GAAATAAGAA
GTAATAATCT ATACTAGCAT TTAAAAAATA TGGGCCAATC TACTCACTAA
TAAATGATTT TTTTTTAACT TGGAAGCTCA TGAATGCTTA CAGAAAATTA
CAAACACATA TTTAGTAATT GTCCAAAATT GACAGGAACG AAAATAAACT
ACTATATATT GCTGTTTTCC TTAGGTGGAT GAGGAAACCG GTTACGTTCC
TGTGATATGC GGCATTGCAC GATGCAAAAA GAGAGACATC GAGGCAACTT
GGGAGGCACT GAAGTATGCG AAGAGGCCGA GGGTAATGCT ATTCACATCT
ACTAGTGAAA TTCACATGAA ATATAAGTTG AAAAAGACTA AGAAGAAGT
GATCGAGATG GCCGTGAACA GTGTTAAGTA CGCTAAAAGC TTGGGCTTCA
AAGACATCCA ATTTGGGTGC GAAGATGGCG GCAGGTATCT TGAAACTTAG
TATAACTCGA TTGTTCTTTT TTTCCGGCCA CTAGGTTTAA CGTTACAAAA
TCTTTGTTAG TAAACTTACT TTTTTTTTTT AATTACGTAC GTTTATCTTT
TACAAGAATA TTGAAAATGT TTTGATTAAT TTTTTTTTGT TTTATAAAAC
AATATTTACA TGCAAACACA AAAGCATAAA TTCAACGCTG AAATAATATA
VWTCTCATAATC TAAAACGCTT TTAGCTGATT TGTTTTGTGA AATTTAAAAT
TTTGTTTTTT GAAAGTTGTT TTTATATAAG GTATGAGAAT GAAAAATATA
AGGGTGTGCC TTATACAGTT ATCTGGCCCA GTTTTGATCA TGTCATATAT
AGATTTTATA GTATACTAGT TTGTGATTCA GGACGGAGAA AGATTTTATA
TGTAAGATTC TAGGAGAATC GATAAAGCG GGTGCAACCA CGGTGGGGTT
TGCGGACACG GTCGGGATCA ACATGCCGCA AGAATTCGGA GAACTCGTGG
CCTATGTCAT AGAAAACACT CCAGGGGCTG ATGATATTGT CTTCGCCATT
CATTGTCATA ACGACCTTGG TGTTGCTACC GCCAACACAA TATCCGTACG
TAATTGCTCT CCCTTTGTCT GAGTTAGATT AATCAACAAA AATTCCGAAC
AAATTTAAAT TATCGAGGTG ACAAGATTAT AAATATAAAA CAATGATATG
TATAGGGTAT ATGTGCGGGA GCAAGACAAG TCGAAGTGAC GATCAACGGA
ATTGGTGAAA GAAGTGGGAA TGCGCCGCTT GAAGAGGTAA GATCGTCGTC
GTGAGTATTT CTTTGGTATG TGTCGGCAGG GTATGGTAAA GCAAAAAATT
TAGAAGTGTG GTCTTACACT TCTCTACTAA TTTTATCATA ATTTAAAAGA

Fig. 13B

```
CTAAAAAAAA GTTGTCGTAA AACTAAAGTA AAACCACATA AACGGTACGG
CTAGCTAGTA AATTATTTAA TAGTAACGCC ATAAAAGTAT AAATATAATA
ATTTAACATT ACAATAAGAC CAACATTACA ATCTAGAAGC GTTTATGTGT
TAAAAAAAAA AAAAAAAAAA TTACAATCTA GAAGTAGGCT ACAATGGAAT
TGACATCAGG AAAGAGAGGA ATTGGAATCG AATGCTTCAC GTAACCCTTA
CATTAAGTAT TTCAAACGAT AGCCACCAAA AAGTTATGTA ATGTGACCCC
TAAATTGCGT ATTTAAATTG TGGACTAGAC GTACATGCTT CATGTGCTTT
ATGAAAAGAC TGGTTCTGTG ATTGTATGTA GGTCGTGATG GCTTTGAAAT
GTCGAGGAGA ATCTCTGATG GATGGTGTTT ACACAAAAAT AGACTCACGC
CAAATTATGG CTACAAGCAA GATGGTACGT AACAAACTAG ATATTGAAAT
TTCGATATTT ATATGAAAAC AATGATGCTA ATATTTGGCC TTTATATATA
ATAATTGACT AAAACGTAAA TTCTTGCGCA GGTTCAAGAG CATACCGGCA
TGTATGTTCA ACCACATAAG CCAATAGTTG GAGACAACTG TTTTGTTCAT
GAGAGCGGCA TTCACCAGGT TCCATATATA TATATATATA TATATTACTT
ATGAAAATTG TATATGAGAT TGTTGCGTTG TATGTGTATA ATTGTCCAAA
CATTTTGCAG GATGGAATAT TGAAAAATCG AAGTACATAT GAGATCTTAT
CACCAGAAGA TGTTGGGATC GTAAAATCTG AAAATTCTGG CATTGTTCTT
GGAAAGCTTA GGTAATTATT CTATTAAGTT ATGTTCTTG GTTTTAGATA
ACTATAAGTC TAAAACTATG TACCATCGTC TGATAAATTT ATTTCAACAA
CTATGAAAAT ATGCAGCGGA CGTCATGCTG TAAAAGACCG GCTTAAAGAG
GTACCACACA CACACACAGT ATATATTAGT GACTTCGTAC TATTTTTAGT
CTTTACTTAT AATAATCACA CACACACATA TATATGGGAC CATGGCACAA
TAGAGACTTT ATAGAGATAA ATATTTGATT AGTCATATGT TTTTTTTTTT
TTTTTGTAAT CTCAAGTTGG GATATGAAAT CAGTGATGAG AAATTCAACG
ACATCTTCTC ACGATACAGA GAATTAACGA AGGACAAAAA GGTTTTCATA
TTATATTTTG TATCTTCTCA TTTACATATG CGTCAAATTT GAAATATTTA
GTTATACATA AAATACGAAT AGATTTATAA AATTCTACCA AACATATAAA
CCCCCATACT TACTTGATTT CAATTTGTTA AACTCCACAG AGAATCACAG
ACGCTGATCT GAAGGCATTA GTGGTGAACG GTGCTGAAAT CTCATCAGAA
AAATTAAACA GTAAAGGAAT TAACGACCTT ATGTCAAGCC CTCAGATTTC
CGCTGTTGTATAA
```

Fig. 14

MASSLLTSSV MIPTTGSTVV GRSVLPFQSS LHSLRLTHSY KNPALFISCC
SSVSKNAATS STDLKPVVER WPEYIPNKLP DGNYVRVFDT TLRDGEQSPG
GSLTPPQKLE IARQLAKLRV DIMEVGFPGS SEEELETIKT IAKTVGNEVD
EETGYVPVIC AIARCKHRDI EATWEALKYA KRPRILVFTS TSDIHMKYKL
KKTQEEVIEM AVSSIRFAKS LGFNDIQFGC EDGGRSDKDF LCKILGEAIK
AGVTVVTIGD TVGINMPHEY GELVTYLKAN TPGIDDVVVA VHCHNDLGLA
TANSIAGIRA GARQVEVTIN GIGERSGNAS LEEVVMALKC RGAYVINGVY
TKIDTRQIMA TSKMVQEYTG LYVQAHKPIV GANCFVHESG IHQVRNWWST
YEILSPEDIG IVKSQNSGLV LGKLSGRHAV KDRLKELGYE LDDEKLNAVF
SLFRDLTKNK KRITDADLKA LVTSSDEISL EKLNGANGLK SNGYIPVPQV
SSNV

Fig. 15

CAATTCCCAC ACTATCTTTC CTCCACATTA AAGTAAAGTA TCTCTCTCTT
TTTTCTCCTA CGTACTCCAT AGTGATGGCT TCATCGCTTC TGACATCTTC
CGTTATGATC CCTACCACCG GTTCCACCGT GGTTGGCCGG TCAGTGTTAC
CCTTTCAATC TTCCCTGCAC TCTCTCCGCC TGACCCATTC GTACAAGAAC
CCCGCATTGT TCATCTCATG TTGCTCTTCT GTGTCCAAAA ATGCGGCAAC
TAGTTCTACT GATCTCAAAC CCGTTGTGGA ACGGTGGCCG GAGTACATAC
CGAACAAGCT TCCCGACGGA AACTATGTGC GTGTATTCGA CACGACGCTC
CGTGACGGTG AACAATCTCC TGGTGGATCC CTCACTCCGC CGCAGAAGCT
AGAGATTGCC CGACAGCTCG CTAAACTCCG AGTAGACATC ATGGAAGTCG
GTTTTCCGGG ATCATCTGAA GAAGAGTTAG AAACCATTAA GACCATCGCC
AAGACTGTGG GGAATGAGGT GGATGAGGAA ACAGGTTACG TCCCTGTGAT
ATGCGCCATA GCTCGATGCA AACATAGAGA CATTGAGGCG ACTTGGGAGG
CGCTGAAGTA CGCGAAGAGG CCAAGGATAC TCGTATTCAC ATCTACTAGT
GACATTCACA TGAAATATAA GTTGAAAAAG ACTCAAGAAG AAGTGATTGA
GATGGCCGTG AGTAGTATTA GGTTTGCTAA AGCTTGGGC TTCAATGACA
TCCAGTTTGG GTGCGAAGAT GGCGGCAGGT CGGACAAGGA TTTCCTATGC
AAGATTCTAG GAGAAGCCAT AAAAGCCGGT GTTACGGTGG TGACCATCGG
TGATACGGTA GGGATCAACA TGCCACATGA ATACGGGGAA CTCGTGACTT
ATCTCAAAGC AAACACCCCT GGAATTGACG ATGTTGTCGT CGCTGTTCAT
TGTCACAACG ACCTTGGTCT TGCAACCGCC AACTCAATCG CCGGTATACG
TGCGGGAGCA AGACAGGTCG AAGTAACTAT CAACGGAATT GGTGAAAGAA
GTGGCAATGC GTCGCTTGAG GAGGTCGTGA TGGCTTTGAA ATGTCGAGGG
GCATATGTGA TCAATGGGGT TTACACAAAA ATAGACACAC GCCAAATCAT
GGCTACCAGC AAGATGGTTC AAGAGTACAC GGGCTTGTAT GTTCAAGCAC
ATAAGCCCAT AGTTGGAGCG AACTGTTTTG TTCATGAGAG CGGCATTCAT
CAGGTTCGTA ATTGGTGGAG TACTTATGAG ATCTTATCAC CAGAAGATAT
TGGGATTGTA AAATCTCAAA ATTCCGGCCT TGTTCTTGGA AAGCTTAGTG
GACGTCACGC TGTGAAAGAT CGGCTGAAAG AGTTGGGATA TGAACTCGAT
GATGAGAAAT TGAACGCTGT CTTCTCACTA TTCAGAGATT TAACCAAGAA
TAAAAAGAGA ATCACGGATG CTGATTTGAA GGCATTAGTA ACATCTAGCG
ATGAAATCTC TTTGGAGAAA TTAAACGGCG CTAACGGTTT AAAGTCTAAC
GGCTATATAC CAGTTCCTCA GGTTTCATCG AATGTG

Fig. 16A

TACTAGAAAT TAAAATTAGT AAGACTGACT AATTACAAAT ATCCCAAGTC
TGTGTTTATT CTAAGACAAC TACTAGAAAA CTTAACTATA TTAGACTACC
AACTAGGCAA CAAATATCAC AAAGAATATC GTATGTCACC TACCTGGAGG
TGCATACCAC GTGATTTTAT CCCCATTTTA GATATGGTCA TATCGATTAG
TTATTGTATA TAAAAAAAAA ATTCTTACAG GCTATAAACT ATTATGCTAC
AAATTTTGGT AAAAACCTAT TACTTGTTAT TCCGTTTCCA AAACATATTA
TGGCTATATT AAAGTGTGTA TAAATGAGTT AAAACATTTT TAACAACAAA
TAAATGTAAA AAAAATGAGT TTAACATCGT TGTAAGTAAA CTTAGGATTT
GTTTGTTACC TCAAACTTAA ATATTATTCC CTCTGTTTCT AACTAAGTGT
AGTTTAAAGG TTTTTTATTT TTTTCAGTAT AAGTATTGTT TTCACTTTTC
GATGCAAACA TTAAATGTAT TTAATAGTTT TTAACCAATT ATATTTTACA
TCATATTTTT TATTGGTTGG ATTAGTTGTA ATTGGTGATA TTTTTTTTAA
AAAAAGATAA ATCAAATGAG ATTTATATAT TTTCTTAATT TGCGTGCAAA
AACTTTAAAT TAAAAATATT AAGAAACAGA GAGAGTATCT TTTCTATACA
TAGGTATATC ACTTATATAT ATATATATGT ATACAGCTAA ATATTTATGT
AAAAATGTAA ACATACGAAA CTGTTTATAG AAAGTATAAT ATTCTAAAAT
AAGATATCAA ACACAGTATA ATATTTAATT TTAAAGAAGA TACTATTTTG
CGTTTAATGT TTTCATCGAA TATAATTTCT TATTCCGCTA ACTCAAATGT
TTATTATTTT TAACATCAAA ATGTTTCTAA TACTAAAAAG TTTAATAAAT
AAAAAAAATCT CTCTATAAAT AGATAAATTA TATCGTATAA TGTTCAAAAC
AATTCCCACA CTATCTTTCC TCCACATTAA AGTAAAGTAT CTCTCTCTTT
TTTCTCCTAC GTACTCCATA GTGATGGCTT CATCGCTTCT GACATCTTCC
GTTATGATCC CTACCACCGG TTCCACCGTG GTTGGCCGGT CAGTGTTACC
CTTTCAATCT TCCCTGCACT CTCTCCGCCT GACCCATTCG TACAAGAACC
CCGCATTGTT CATCTCATGT TGCTCTTCTG TGTCCAAAAA TGCGGCAACT
AGTTCTACTG ATCTCAAACC CGTTGTGGAA CGGTGGCCGG AGTACATACC
GAACAAGCTT CCCGACGGAA ACTATGTGCG TGTATTCGAC ACGACGCTCC
GTGACGGTGA ACAATCTCCT GGTGGATCCC TCACTCCGCC GCAGAAGCTA
GAGATTGCCC GACAGCTCGC TAAACTCCGA GTAGACATCA TGGAAGTCGG
TTTTCCGGGA TCATCTGAAG AAGAGTTAGA ACCATTAAG ACCATCGCCA
AGACTGTGGG GAATGAGGTT TTTTCTTTAT TTCCTTCACT TAAATGATTA
TGTACATATT TTAACACACA AAAAAAAACT TGATATAATT TTATGTTCAA
ACTATATATA TATAGTTGAT AAATTGCACA TGACCCTTAT AGTTGAGGCC
GAAATAAAGA AAACAAATTA TGTGTTTAGA ATTTTTTCAA AAACGGCTGA
TGAATACATT AGGACTATTT GTCTTAATTT ATAAACTGTA TTAGTATTTA
AATTTTACTA CTAATTTTGC GGTCCTTATT TATTTTATT TTAATCCGTT
TGTTGTAGCC TGCTGCTTTT TTTGTTTTCC TTCACTTGGA TGTAGTTTTA
TTCGTGTTTT TTTTTCCTAC CATCTATTCT TCTAGTTATA GTGTTATTTA
TAATTAGCCA AGTTCTAACG GGTTAGAGAA AGCACATGCA CATGATTAGT
TAGAGCCGGT CGTATAGTTA AGATTTTTTT TTTGTGACAT ATATATGACA
AAATTATGTG TAAAAGTGTA AGAATCCCAT ATATATCAGA AATACAATTC

Fig. 16B

TAGCATATAC AATATATGAG TTAATATTAT ATAGTCATTA CTAGTTGGTT
TTGTGTTGAA ACTCATGAAT GCTCCCAAAT GGAGCGAGTA ACGGTCAAAG
TTGACAACAA CGAACATTAA TTACTATATT GTTGTTTTGC TTAGGTGGAT
GAGGAAACAG GTTACGTCCC TGTGATATGC GCCATAGCTC GATGCAAACA
TAGAGACATT GAGGCGACTT GGGAGGCGCT GAAGTACGCG AAGAGGCCAA
GGATACTCGT ATTCACATCT ACTAGTGACA TTCACATGAA ATATAAGTTG
AAAAAGACTC AAGAAGAAGT GATTGAGATG GCCGTGAGTA GTATTAGGTT
TGCTAAAAGC TTGGGCTTCA ATGACATCCA GTTTGGGTGC GAAGATGGCG
GCAGGTCCAA ATCTTTAAAC CTTTATATAT CTCAATTGTT TCTCTGCGTT
TTTGGTTTAG TTTTATTTAT GCTTAGTTTG TATTACCAAA CTATTTTTGT
TAGTAACTTA TGTTTGCGTT GACATTTGGG TATATTTTTG GCAAGAATAA
TTCACAAACA AAAGGCATGA ATGATTGTGA GTTTTTTTGT TTTTTTTTAT
ATAGTTTTTG GTTTCTGGAT TTTAGAATTT GGTTTTTGGA TTTTGCAAAA
ATAGAAAATA GATAAGTGGG GAAAAAATGT TATGTTAAGA ATTTGTTCAG
GAAAAGTGAA GAACTCAAAT AAGATGGTTT TTAGATTGTC ACTAAAACAT
TGTTAAGATC TTTCAAACAC TAGATTTCTA GATCATAATA GAAAAGGCGG
TTTTAGCTGT TACTAGATAT GTTATGGATT TTGTGCGAAT TTTACATATA
TGATCATGTC ATATATATAT ATATATATTT GATTTTAAAA TATAGTGTGA
TTCAGGTCGG ACAAGGATTT CCTATGCAAG ATTCTAGGAG AAGCCATAAA
AGCCGGTGTT ACGGTGGTGA CCATCGGTGA TACGGTAGGG ATCAACATGC
CACATGAATA CGGGGAACTC GTGACTTATC TCAAAGCAAA CACCCCTGGA
ATTGACGATG TTGTCGTCGC TGTTCATTGT CACAACGACC TTGGTCTTGC
AACCGCCAAC TCAATCGCCG TACGGAACTA ACTCTTTTTT TGTGTGTGTG
TGTTAGATAT ATTTTCATAT ATATATTTAC TAATATAGAT TCTCAATGTG
ACAAAAATAT GAACATATAA AACAACGAAT TTACATGATA TATATATAGG
GTATACGTGC GGGAGCAAGA CAGGTCGAAG TAACTATCAA CGGAATTGGT
GAAAGAAGTG GCAATGCGTC GCTTGAGGAG GTATCATCAT TTTTGTTACC
ATAATCTCAT CACTACCATG ATCATGATCA TGATCATCAT TATCAACATG
ACCATTTAAA TGGTATGTAG GTCGTGATGG CTTTGAAATG TCGAGGGGCA
TATGTGATCA ATGGGGTTTA CACAAAATA GACACACGCC AAATCATGGC
TACCAGCAAG ATGGTATATA TTCACACATG CCATATATAT ACATATATAT
ATATATATAT ATAATTAATT AACAAAAATT TATGTAAACT CTTGAGCAGG
TTCAAGAGTA CACGGGCTTG TATGTTCAAG CACATAAGCC CATAGTTGGA
GCGAACTGTT TTGTTCATGA GAGCGGCATT CATCAGGTTC GTAATTGGTG
GTAAACACGG ATATTAAGAA ATTATATAAA CTATTTTAGA TTTTTGTTTT
TAAAATCCCT TTAACCAACA CTAATCGAAT ATTCTAGATG TACACTATAA
CTAAAATAAA CATTTACATT ATATATGTGA TAATAAAAAT ACATACGAGA
TTAAATTGAT TTATATGATG TTTGTTCCAA TATTTTTCAG GATGGAATAT
TGAAAAATAG GAGTACTTAT GAGATCTTAT CACCAGAAGA TATTGGGATT
GTAAAATCTC AAAATTCCGG CCTTGTTCTT GGAAAGCTTA GGTTAATATT
CTATTTAGTG ATACTTTTAC CTACGAACAA TTGTTTTATT TGTCTTCTTA

Fig. 16C

TATATTAATT TTAACAACAA TGGAAATGTG CAGTGGACGT CACGCTGTGA
AAGATCGGCT GAAAGAGGTA TTCCTTGTGA CAATTGTACC TACCTACTAG
ATTACACTTC CTAGAGATAA ATATTAGATG ATTCATATAC TTACTTATGT
GTATATTTTC TATTTTCAGT TGGGATATGA ACTCGATGAT GAGAAATTGA
ACGCTGTCTT CTCACTATTC AGAGATTTAA CCAAGAATAA AAAGGTTTTC
AATTTCTATA TATTTTGTAT CTCCTCGTGC ACATGCATGC AATACGGTTT
AACTAACAAA TTTAATCATA TATGGTATAA GAATGTAAGA AACGAACTGA
TTTTAAAGTT TTAGAAAAGA AAATCTCAAA CTTTTATTTT GAAAAAATAT
CTCGAACTTA ATGTGTTTTC ATTTGTCAAA ATTTTCAGAG AATCACGGAT
GCTGATTTGA AGGCATTAGT AACATCTAGC GATGAAATCT CTTTGGAGAA
ATTAAACGGC GCTAACGGTT TAAAGTCTAA CGGCTATATA CCAGTTCCTC
AGGTTTCATC GAATGTGTAA

Fig. 17
Isopropylmalate synthase
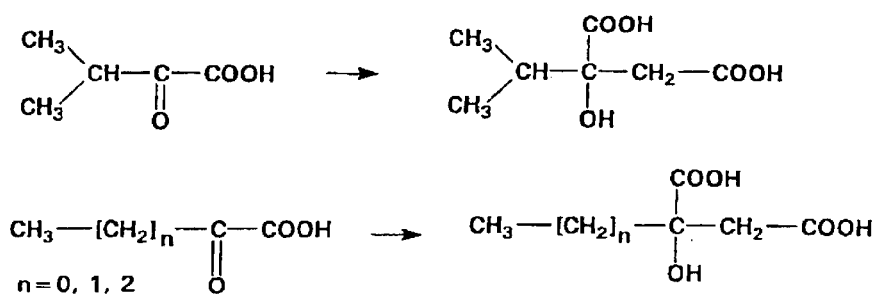
Homocitrate synthase
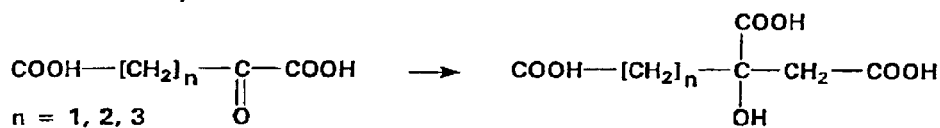
GSL-ELONG alleles (methylthioalkylmalate synthase)
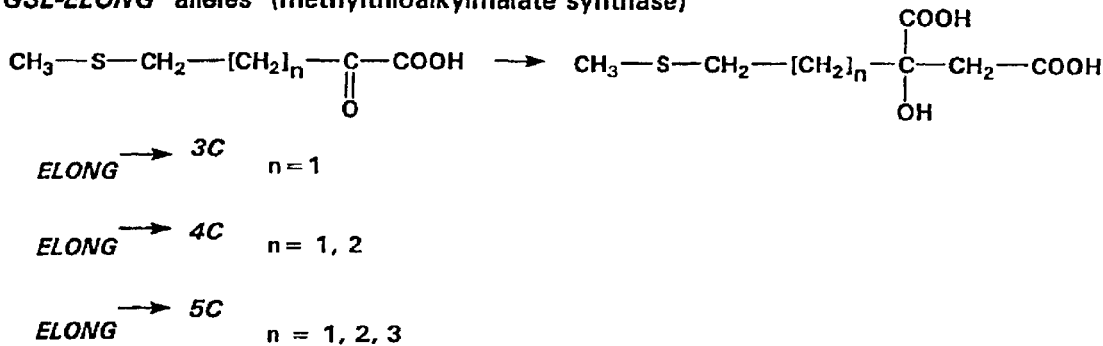

SEQUENCE LISTING

<160> NUMBER OF SEQ ID NOS: 24

<210> SEQ ID NO 1
<211> LENGTH: 485
<212> TYPE: PRT
<213> ORGANISM: Arabidopsis thaliana

<400> SEQUENCE: 1

```
Met Val Leu Arg Ser Gly Leu Pro Ile Gly Ser Ser Phe Pro Ser Leu
 1               5                  10                  15

Arg Leu Thr Arg Pro Tyr Asp Lys Ala Thr Leu Phe Val Ser Cys Cys
                20                  25                  30

Ser Ala Glu Ser Lys Lys Val Ala Thr Ser Ala Thr Asp Leu Lys Pro
            35                  40                  45

Ile Met Glu Arg Arg Pro Glu Tyr Ile Pro Asn Lys Leu Pro His Lys
        50                  55                  60

Asn Tyr Val Arg Val Leu Asp Thr Thr Leu Arg Asp Gly Glu Gln Ser
 65                  70                  75                  80

Pro Gly Ala Ala Leu Thr Pro Pro Gln Lys Leu Glu Ile Ala Arg Gln
                85                  90                  95

Leu Ala Lys Leu Arg Val Asp Ile Met Glu Val Gly Phe Pro Val Ser
            100                 105                 110

Ser Glu Glu Glu Phe Glu Ala Ile Lys Thr Ile Ala Lys Thr Val Gly
        115                 120                 125

Asn Glu Val Asp Glu Glu Thr Gly Tyr Val Pro Val Ile Cys Gly Ile
    130                 135                 140

Ala Arg Cys Lys Lys Arg Asp Ile Glu Ala Thr Trp Glu Ala Leu Lys
145                 150                 155                 160

Tyr Ala Lys Arg Pro Arg Val Met Leu Phe Thr Ser Thr Ser Glu Ile
                165                 170                 175

His Met Lys Tyr Lys Leu Lys Lys Thr Lys Glu Glu Val Ile Glu Met
            180                 185                 190

Ala Val Asn Ser Val Lys Tyr Ala Lys Ser Leu Gly Phe Lys Asp Ile
        195                 200                 205

Gln Phe Gly Cys Glu Asp Gly Gly Arg Thr Glu Lys Asp Phe Ile Cys
    210                 215                 220

Lys Ile Leu Gly Glu Ser Ile Lys Ala Gly Ala Thr Thr Val Gly Phe
225                 230                 235                 240

Ala Asp Thr Val Gly Ile Asn Met Pro Gln Glu Phe Gly Glu Leu Val
                245                 250                 255

Ala Tyr Val Ile Glu Asn Thr Pro Gly Ala Asp Asp Ile Val Phe Ala
            260                 265                 270

Ile His Cys His Asn Asp Leu Gly Val Ala Thr Ala Asn Thr Ile Ser
        275                 280                 285

Gly Ile Cys Ala Gly Ala Arg Gln Val Glu Val Thr Ile Asn Gly Ile
    290                 295                 300

Gly Glu Arg Ser Gly Asn Ala Pro Leu Glu Val Val Met Ala Leu
305                 310                 315                 320

Lys Cys Arg Gly Glu Ser Leu Met Asp Gly Val Tyr Thr Lys Ile Asp
                325                 330                 335

Ser Arg Gln Ile Met Ala Thr Ser Lys Met Val Gln Glu His Thr Gly
            340                 345                 350

Met Tyr Val Gln Pro His Lys Pro Ile Val Gly Asp Asn Cys Phe Val
```

```
                355              360              365
His Glu Ser Gly Ile His Gln Asp Gly Ile Leu Lys Asn Arg Ser Thr
        370              375              380

Tyr Glu Ile Leu Ser Pro Glu Asp Val Gly Ile Val Lys Ser Glu Asn
385              390              395              400

Ser Gly Ile Val Leu Gly Lys Leu Ser Gly Arg His Ala Val Lys Asp
            405              410              415

Arg Leu Lys Glu Leu Gly Tyr Glu Ile Ser Asp Glu Lys Phe Asn Asp
            420              425              430

Ile Phe Ser Arg Tyr Arg Glu Leu Thr Lys Asp Lys Lys Arg Ile Thr
            435              440              445

Asp Ala Asp Leu Lys Ala Leu Val Val Asn Gly Ala Glu Ile Ser Ser
        450              455              460

Glu Lys Leu Asn Ser Lys Gly Ile Asn Asp Leu Met Ser Ser Pro Gln
465              470              475              480

Ile Ser Ala Val Val
            485

<210> SEQ ID NO 2
<211> LENGTH: 4875
<212> TYPE: DNA
<213> ORGANISM: Arabidopsis thaliana

<400> SEQUENCE: 2
gctgagtttc aatggttttt gataatgtga tgagagttta gaactggaag aagttatact      60
tactctcata agaataatga ttaggattac ataggtttat atagtaaaga gatttcataa     120
actagatgaa tacaaatatg taaaatatct tatatcataa ctatacaata tttgattata     180
tattgagaat cttctagata cttccatacc cttctatagt tttaactcaa aaatcaattg     240
gcaattggat ttaaagaata taatgtggga ttccattaca cttacgatgg atttgctcaa     300
aaaaagaaaa aagaaagaaa gattccatta catttaggat gtgagattcg taacacgatt     360
caaaataata gctaagacct tttatcttac cgaattccct tttaaaactg caatataccc     420
tacttggatc accctaaact aaagtctaaa ctatcatttt atggttataa acttaattaa     480
aaccaactga caatgaattg aaaaaataat gtgagattcc aaacattatt taattttggg     540
ttgtaaaatc ccaaaaggta tatttaccgc ctttaaaaaa aactaatgaa agcaatttaa     600 attgttctg tgtattctca tcatttcccg tcacttttgt aacaattcca acgttagaac     660
gatcattcac tcgcgtaaat tgttttattt ttattttaaa gcgttttaaa ccataacata     720
aaaaagttta aggatattat aatttttttat caaaaattaa tgatattagg ttatcaagtg     780
gtcgagtaaa tcatctggtt atataaaatt ggagaaaaag attttctacc tatataaata     840
tagatatcat ctgtacatgc actccacctc attgcaaaac aatttcccca ctatctatcc     900
tccataatat agtattcttc ttttctctcc tactttctct atagtaatgg cttcgttact     960
tctcacatcg tcgagtatga taaccactag ctgtcgctcc atggttctcc ggtcagggtt    1020
acccatcgga tcttcttttc cctctcttcg cctgacccgt ccatacgaca aggcgactct    1080
gttcgtctca tgttgctccg ctgagtccaa aaaggtggca actagtgcta ctgatctcaa    1140
acctatcatg gaacggaggc cggagtacat tccgaacaag cttccccaca gaactatgt     1200 gcgtgtatta gacacgacgc ttcgtgacgg tgaacaatct cccggtgcag cacttactcc    1260
accgcagaag ttagagattg ccaggcagct agctaaactc cgagtagaca tcatggaagt    1320
tggttttccg gtgtcgtctg aggaagaatt cgaagctatt aaaaccatcg ccaagaccgt    1380
```

```
ggggaacgag gttagtttct ttatttccct cacttcaaga aaataatata atgatttatg    1440
ttcaaactat atatagatat aataaaatta gatgtgcaaa gtgttagtta aagaatctca    1500
cattagaaat aagaagtaat aatctatact agcatttaaa aaatatgggc caatctactc    1560
actaataaat gatttttttt taacttggaa gctcatgaat gcttacagaa aattacaaac    1620
acatatttag taattgtcca aaattgacag gaacgaaaat aaactactat atattgctgt    1680
tttccttagg tggatgagga aaccggttac gttcctgtga tatgcggcat tgcacgatgc    1740
aaaaagagag acatcgaggc aacttgggag gcactgaagt atgcgaagag gccgagggta    1800
atgctattca catctactag tgaaattcac atgaaatata agttgaaaaa gactaaagaa    1860
gaagtgatcg agatggccgt gaacagtgtt aagtacgcta aaagcttggg cttcaaagac    1920
atccaatttg ggtgcgaaga tggcggcagg tatcttgaaa cttagtataa ctcgattgtt    1980
ctttttttcc ggccactagg tttaacgtta caaaatcttt gttagtaaac ttactttttt    2040
tttttaatta cgtacgttta tcttttacaa gaatattgaa aatgttttga ttaatttttt    2100
tttgttttat aaaacaatat ttacatgcaa acacaaaagc ataaattcaa cgctgaaata    2160
atatatctca taatctaaaa cgcttttagc tgatttgttt tgtgaaattt aaaattttgt    2220
tttttgaaag ttgttttttat ataaggtatg agaatgaaaa ataaagggt gtgccttata    2280 cagttatctg gcccagtttt gatcatgtca tatatagatt ttatagtata ctagtttgtg    2340
attcaggacg gagaaagatt ttatatgtaa gattctagga gaatcgataa aagcgggtgc    2400
aaccacggtg gggtttgcgg acacggtcgg gatcaacatg ccgcaagaat tcggagaact    2460
cgtggcctat gtcatagaaa acactccagg ggctgatgat attgtcttcg ccattcattg    2520
tcataacgac cttggtgttg ctaccgccaa cacaatatcc gtacgtaatt gctctcccctt   2580 tgtctgagtt agattaatca acaaaaattc cgaacaaatt taaattatcg aggtgacaag    2640
attataaata taaacaatg atatgtatag ggtatatgtg cgggagcaag acaagtcgaa    2700
gtgacgatca acggaattgg tgaaagaagt gggaatgcgc cgcttgaaga ggtaagatcg    2760
tcgtcgtgag tatttcttg gtatgtgtcg gcagggtatg gtaaagcaaa aaatttagaa    2820
gtgtggtctt acacttctct actaattttta tcataattta aaagactaaa aaaagttgt    2880 cgtaaaacta aagtaaaacc acataaacgg tacggctagc tagtaaaatta tttaatagta    2940 acgccataaa agtataaata taataattta acattacaat aagaccaaca ttacaatcta    3000
gaagcgttta tgtgttaaaa aaaaaaaaaa aaaaattaca atctagaagt aggctacaat    3060
ggaattgaca tcaggaaaga gaggaattgg aatcgaatgc ttcacgtaac ccttacatta    3120
agtatttcaa acgatagcca ccaaaaagtt atgtaatgtg accccctaaat tgcgtattta    3180 aattgtggac tagacgtaca tgcttcatgt gctttatgaa aagactggtt ctgtgattgt    3240
atgtaggtcg tgatggcttt gaaatgtcga ggagaatctc tgatggatgg tgtttacaca    3300
aaaatagact cacgccaaat tatggctaca agcaagatgg tacgtaacaa actagatatt    3360
gaaatttcga tatttatatg aaaacaatga tgctaatatt tggccttttat atataataat    3420 tgactaaaac gtaaattctt gcgcaggttc aagagcatac cggcatgtat gttcaaccac    3480
ataagccaat agtggagac aactgttttg ttcatgagag cggcattcac caggttccat    3540
atatatatat atatatatat tacttatgaa aattgtatat gagattgttg cgttgtatgt    3600
gtataattgt ccaaacattt tgcaggatgg aatattgaaa aatcgaagta catatgagat    3660
cttatcacca gaagatgttg ggatcgtaaa atctgaaaat tctggcattg ttcttggaaa    3720
```

```
gcttaggtaa ttattctatt aagttatgtt tcttggtttt agataactat aagtctaaaa    3780
ctatgtacca tcgtctgata aatttatttc aacaactatg aaaatatgca gcggacgtca    3840
tgctgtaaaa gaccggctta aagaggtacc acacacacac acagtatata ttagtgactt    3900
cgtactattt ttagtcttta cttataataa tcacacacac acatatatat gggaccatgg    3960
cacaatagag actttataga gataaatatt tgattagtca tatgttttttt ttttttttt    4020 gtaatctcaa gttgggatat gaaatcagtg atgagaaatt caacgacatc ttctcacgat    4080
acagagaatt aacgaaggac aaaaaggttt tcatattata ttttgtatct tctcatttac    4140
atatgcgtca aatttgaaat atttagttat acataaaata cgaatagatt tataaaattc    4200
taccaaacat ataaaccccc atacttactt gatttcaatt tgttaaactc cacagagaat    4260
cacagacgct gatctgaagg cattagtggt gaacggtgct gaaatctcat cagaaaaatt    4320
aaacagtaaa ggaattaacg accttatgtc aagccctcag atttccgctg ttgtataagt    4380
ttgggaagac attgtgtaat tttgtactac gatggtatta agtcactttt gttttactgt    4440
gttttgtgta ctatatatac gtaccttttg gtttttatgt tatcgttgta atgaataaaa    4500
cagtattaat agggagtgtt tttattctat aattaaactc tcttttttat aatgattttc    4560
accaaagtat tggaaattta aacaaacatt accatattcc attgaagatt caacaaagta    4620
ttgttcattt tcagttgtga tcattattct tcctcacact actgcattaa attgttaatc    4680
aaatgctccc gtcatgacaa ctactataat ttactgttaa ctaagcatta ataaaatttt    4740
gatcatctac cgttaaaatt ataaaacatg aattgcctca tcatagtaag agtcgtattt    4800
ttctttcagg ggtggttgat agctatattg tcgttctata tgtgggacat gttaccctaa    4860
acggaaaagt atttg                                                    4875
```

<210> SEQ ID NO 3
<211> LENGTH: 503
<212> TYPE: PRT
<213> ORGANISM: Arabidopsis thaliana

<400> SEQUENCE: 3

```
Met Ala Ser Leu Leu Thr Ser Ser Ser Met Ile Thr Thr Ser Cys
 1               5                  10                  15

Pro Ser Met Val Leu Arg Ser Gly Leu Pro Ile Gly Ser Ser Phe Pro
                20                  25                  30

Ser Leu Arg Leu Thr Arg Pro Tyr Asp Lys Ala Thr Leu Phe Val Ser
            35                  40                  45

Cys Cys Ser Ala Glu Ser Lys Lys Val Ala Thr Ser Ala Thr Asp Leu
        50                  55                  60

Lys Pro Ile Met Glu Arg Arg Pro Glu Tyr Ile Pro Asn Lys Leu Pro
    65                  70                  75                  80

His Lys Asn Tyr Val Arg Val Leu Asp Thr Thr Leu Arg Asp Gly Glu
                85                  90                  95

Gln Ser Pro Gly Ala Ala Leu Thr Pro Gln Lys Leu Glu Ile Ala
            100                 105                 110

Arg Gln Leu Ala Lys Leu Arg Val Asp Ile Met Glu Val Gly Phe Pro
        115                 120                 125

Val Ser Ser Glu Glu Glu Phe Glu Ala Ile Lys Thr Ile Ala Lys Thr
    130                 135                 140

Val Gly Asn Glu Val Asp Glu Glu Thr Gly Tyr Val Pro Val Ile Cys
145                 150                 155                 160

Gly Ile Ala Arg Cys Lys Lys Arg Asp Ile Glu Ala Thr Trp Glu Ala
```

-continued

```
                165                 170                 175
Leu Lys Tyr Ala Lys Arg Pro Arg Val Met Leu Phe Thr Ser Thr Ser
            180                 185                 190
Glu Ile His Met Lys Tyr Lys Leu Lys Lys Thr Lys Glu Glu Val Ile
        195                 200                 205
Glu Met Ala Val Asn Ser Val Lys Tyr Ala Lys Ser Leu Gly Phe Lys
    210                 215                 220
Asp Ile Gln Phe Gly Cys Glu Asp Gly Gly Arg Thr Glu Lys Asp Phe
225                 230                 235                 240
Ile Cys Lys Ile Leu Gly Glu Ser Ile Lys Ala Gly Ala Thr Thr Val
                245                 250                 255
Gly Phe Ala Asp Thr Val Gly Ile Asn Met Pro Gln Glu Phe Gly Glu
            260                 265                 270
Leu Val Ala Tyr Val Ile Glu Asn Thr Pro Gly Ala Asp Asp Ile Val
        275                 280                 285
Phe Ala Ile His Cys His Asn Asp Leu Gly Val Ala Thr Ala Asn Thr
    290                 295                 300
Ile Ser Gly Ile Cys Ala Gly Ala Arg Gln Val Glu Val Thr Ile Asn
305                 310                 315                 320
Gly Ile Gly Glu Arg Ser Gly Asn Ala Pro Leu Glu Glu Val Val Met
                325                 330                 335
Ala Leu Lys Cys Arg Gly Glu Ser Leu Met Asp Gly Val Tyr Thr Lys
            340                 345                 350
Ile Asp Ser Arg Gln Ile Met Ala Thr Ser Lys Met Val Gln Glu His
        355                 360                 365
Thr Gly Met Tyr Val Gln Pro His Lys Pro Ile Val Gly Asp Asn Cys
    370                 375                 380
Phe Val His Glu Ser Gly Ile His Gln Asp Gly Ile Leu Lys Asn Arg
385                 390                 395                 400
Ser Thr Tyr Glu Ile Leu Ser Pro Glu Asp Val Gly Ile Val Lys Ser
                405                 410                 415
Glu Asn Ser Gly Ile Val Leu Gly Lys Leu Ser Gly Arg His Ala Val
            420                 425                 430
Lys Asp Arg Leu Lys Glu Leu Gly Tyr Glu Ile Ser Asp Glu Lys Phe
        435                 440                 445
Asn Asp Ile Phe Ser Arg Tyr Arg Glu Leu Thr Lys Asp Lys Lys Arg
    450                 455                 460
Ile Thr Asp Ala Asp Leu Lys Ala Leu Val Val Asn Gly Ala Glu Ile
465                 470                 475                 480
Ser Ser Glu Lys Leu Asn Ser Lys Gly Ile Asn Asp Leu Met Ser Ser
                485                 490                 495
Pro Gln Ile Ser Ala Val Val
            500

<210> SEQ ID NO 4
<211> LENGTH: 504
<212> TYPE: PRT
<213> ORGANISM: Arabidopsis thaliana

<400> SEQUENCE: 4

Met Ala Ser Ser Leu Leu Thr Ser Ser Val Met Ile Pro Thr Thr Gly
  1               5                  10                  15
Ser Thr Val Val Gly Arg Ser Val Leu Pro Phe Gln Ser Ser Leu His
             20                  25                  30
```

```
Ser Leu Arg Leu Thr His Ser Tyr Lys Asn Pro Ala Leu Phe Ile Ser
        35                  40                  45

Cys Cys Ser Ser Val Ser Lys Asn Ala Ala Thr Ser Ser Thr Asp Leu
    50                  55                  60

Lys Pro Val Val Glu Arg Trp Pro Glu Tyr Ile Pro Asn Lys Leu Pro
 65                  70                  75                  80

Asp Gly Asn Tyr Val Arg Val Phe Asp Thr Thr Leu Arg Asp Gly Glu
                85                  90                  95

Gln Ser Pro Gly Gly Ser Leu Thr Pro Pro Gln Lys Leu Glu Ile Ala
            100                 105                 110

Arg Gln Leu Ala Lys Leu Arg Val Asp Ile Met Glu Val Gly Phe Pro
        115                 120                 125

Gly Ser Glu Glu Glu Leu Glu Thr Ile Lys Thr Ile Ala Lys Thr
        130                 135                 140

Val Gly Asn Glu Val Asp Glu Glu Thr Gly Tyr Val Pro Val Ile Cys
145                 150                 155                 160

Ala Ile Ala Arg Cys Lys His Arg Asp Ile Glu Ala Thr Trp Glu Ala
                165                 170                 175

Leu Lys Tyr Ala Lys Arg Pro Arg Ile Leu Val Phe Thr Ser Thr Ser
            180                 185                 190

Asp Ile His Met Lys Tyr Lys Leu Lys Lys Thr Gln Glu Glu Val Ile
        195                 200                 205

Glu Met Ala Val Ser Ser Ile Arg Phe Ala Lys Ser Leu Gly Phe Asn
    210                 215                 220

Asp Ile Gln Phe Gly Cys Glu Asp Gly Gly Arg Ser Asp Lys Asp Phe
225                 230                 235                 240

Leu Cys Lys Ile Leu Gly Glu Ala Ile Lys Ala Gly Val Thr Val Val
                245                 250                 255

Thr Ile Gly Asp Thr Val Gly Ile Asn Met Pro His Glu Tyr Gly Glu
            260                 265                 270

Leu Val Thr Tyr Leu Lys Ala Asn Thr Pro Gly Ile Asp Asp Val Val
        275                 280                 285

Val Ala Val His Cys His Asn Asp Leu Gly Leu Ala Thr Ala Asn Ser
    290                 295                 300

Ile Ala Gly Ile Arg Ala Gly Ala Arg Gln Val Glu Val Thr Ile Asn
305                 310                 315                 320

Gly Ile Gly Glu Arg Ser Gly Asn Ala Ser Leu Glu Glu Val Val Met
                325                 330                 335

Ala Leu Lys Cys Arg Gly Ala Tyr Val Ile Asn Gly Val Tyr Thr Lys
            340                 345                 350

Ile Asp Thr Arg Gln Ile Met Ala Thr Ser Lys Met Val Gln Glu Tyr
        355                 360                 365

Thr Gly Leu Tyr Val Gln Ala His Lys Pro Ile Val Gly Ala Asn Cys
    370                 375                 380

Phe Val His Glu Ser Gly Ile His Gln Val Arg Asn Trp Trp Ser Thr
385                 390                 395                 400

Tyr Glu Ile Leu Ser Pro Glu Asp Ile Gly Ile Val Lys Ser Gln Asn
                405                 410                 415

Ser Gly Leu Val Leu Gly Lys Leu Ser Gly Arg His Ala Val Lys Asp
            420                 425                 430

Arg Leu Lys Glu Leu Gly Tyr Glu Leu Asp Asp Glu Lys Leu Asn Ala
        435                 440                 445

Val Phe Ser Leu Phe Arg Asp Leu Thr Lys Asn Lys Lys Arg Ile Thr
```

```
                450             455             460
Asp Ala Asp Leu Lys Ala Leu Val Thr Ser Ser Asp Glu Ile Ser Leu
465                 470                 475                 480

Glu Lys Leu Asn Gly Ala Asn Gly Leu Lys Ser Asn Gly Tyr Ile Pro
                485                 490                 495

Val Pro Gln Val Ser Ser Asn Val
            500

<210> SEQ ID NO 5
<211> LENGTH: 1455
<212> TYPE: DNA
<213> ORGANISM: Arabidopsis thaliana

<400> SEQUENCE: 5
```

| | | | | | |
|---|---|---|---|---|---|
| atggttctcc | ggtcagggtt | acccatcgga | tcttcttttc | cctctcttcg | cctgacccgt | 60 |
| ccatacgaca | aggcgactct | gttcgtctca | tgttgctccg | ctgagtccaa | aaaggtggca | 120 |
| actagtgcta | ctgatctcaa | acctatcatg | gaacggaggc | cggagtacat | tccgaacaag | 180 |
| cttccccaca | agaactatgt | gcgtgtatta | gacacgacgc | ttcgtgacgg | tgaacaatct | 240 |
| cccggtgcag | cacttactcc | accgcagaag | ttagagattg | ccaggcagct | agctaaactc | 300 |
| cgagtagaca | tcatggaagt | tggttttccg | gtgtcgtctg | aggaagaatt | cgaagctatt | 360 |
| aaaaccatcg | ccaagaccgt | ggggaacgag | gtggatgagg | aaaccggtta | cgttcctgtg | 420 |
| atatgcggca | ttgcacgatg | caaaaagaga | gacatcgagg | caacttggga | ggcactgaag | 480 |
| tatgcgaaga | ggccgagggt | aatgctattc | acatctacta | gtgaaattca | catgaaatat | 540 |
| aagttgaaaa | agactaaaga | agaagtgatc | gagatggccg | tgaacagtgt | taagtacgct | 600 |
| aaaagcttgg | gcttcaaaga | catccaattt | gggtgcgaag | atggcggcag | gacggagaaa | 660 |
| gattttatat | gtaagattct | aggagaatcg | ataaaagcgg | gtgcaaccac | ggtggggttt | 720 |
| gcggacacgt | cgggatcaa | catgccgcaa | gaattcggaa | actcgtggc | ctatgtcata | 780 |
| gaaaacactc | caggggctga | tgatattgtc | ttcgccattc | attgtcataa | cgaccttggt | 840 |
| gttgctaccg | ccaacacaat | atccggtata | tgtgcgggag | caagacaagt | cgaagtgacg | 900 |
| atcaacggaa | ttggtgaaag | aagtgggaat | gcgccgcttg | aagaggtcgt | gatggctttg | 960 |
| aaatgtcgag | gagaatctct | gatggatggt | gtttacacaa | aaatagactc | acgccaaatt | 1020 |
| atggctacaa | gcaagatggt | tcaagagcat | accggcatgt | atgttcaacc | acataagcca | 1080 |
| atagttggag | acaactgttt | tgttcatgag | agcggcattc | accaggatgg | aatattgaaa | 1140 |
| aatcgaagta | catatgagat | cttatcacca | gaagatgttg | ggatcgtaaa | atctgaaaat | 1200 |
| tctggcattt | tccttggaaa | gcttagcgga | cgtcatgctg | taaagaccg | gcttaaagag | 1260 |
| ttgggatatg | aaatcagtga | tgagaaattc | aacgacatct | tctcacgata | cagagaatta | 1320 |
| acgaaggaca | aaaagagaat | cacagacgct | gatctgaagg | cattagtggt | gaacggtgct | 1380 |
| gaaatctcat | cagaaaaatt | aaacagtaaa | ggaattaacg | accttatgtc | aagccctcag | 1440 |
| atttccgctg | ttgta | | | | | 1455 |

```
<210> SEQ ID NO 6
<211> LENGTH: 1590
<212> TYPE: DNA
<213> ORGANISM: Arabidopsis thaliana

<400> SEQUENCE: 6
```

| | | | | | |
|---|---|---|---|---|---|
| acctcattgc | aaagcaattt | ccccactatc | tatcctccat | aatatagtat | tcctcttttc | 60 |

-continued

```
tctcctacgt tctctatagt aatggcttcg ttacttctca catcttccag tatgataacc      120
actagctgtc cctccatggt tctccggtca gggttaccca tcggatcttc ttttccctct      180
cttcgcctga cccgtccata cgacaaggcg actctgttcg tctcatgttg ctccgctgag      240
tccaaaaagg tggcaactag tgctactgat ctcaaaccta tcatggaacg gaggccggag      300
tacattccga acaagcttcc ccacaagaac tatgtgcgtg tattagacac gacgcttcgt      360
gacggtgaac aatctcccgg tgcagcactt actccaccgc agaagttaga gattgccagg      420
cagctagcta aactccgagt agacatcatg gaagttggtt ttccggtgtc gtctgaggaa      480
gaattcgaag ctattaaaac catcgccaag accgtgggga acgaggtgga tgaggaaacc      540
ggttacgttc ctgtgatatg cggcattgca cgatgcaaaa agagagacat cgaggcaact      600
tgggaggcac tgaagtatgc gaagaggccg agggtaatgc tattcacatc tactagtgaa      660
attcacatga aatataagtt gaaaagact  aagaagaag tgatcgagat ggccgtgaac      720
agtgttaagt acgctaaaag cttgggcttc aaagacatcc aatttgggtg cgaagatggc      780
ggcaggacgg agaaagattt tatatgtaag attctaggag aatcgataaa gcgggtgca       840 accacggtgg ggtttgcgga cacggtcggg atcaacatgc cgcaagaatt cggagaactc      900
gtggcctatg tcatagaaaa cactccaggg gctgatgata ttgtcttcgc cattcattgt      960
cataacgacc ttggtgttgc taccgccaac acaatatccg gtatatgtgc gggagcaaga     1020
caagtcgaag tgacgatcaa cggaattggt gaaagaagtg ggaatgcgcc gcttgaagag     1080
gtcgtgatgc ctttgaaatg tcgaggagaa tctctgatgg atggtgttta cacaaaaata     1140
gactcacgcc aaattatggc tacaagcaag atggttcaag agcataccgg catgtatgtt     1200
caaccacata agccaatagt tggagacaac tgttttgttc atgagagcgg cattcaccag     1260
gatggaatat tgaaaaatcg aagtacatat gagatcttat caccagaaga tgttgggatc     1320
gtaaaatctg aaaattctgg cattgttctt ggaaagctta gcggacgtca tgctgtaaaa     1380
gaccggctta aagagttggg atatgaaatc agtgatgaga aattcaacga catcttctca     1440
cgatacagag aattaacgaa ggacaaaaag agaatcacag acgctgatct gaaggcatta     1500
gtggtgaacg gtgctgaaat tcatcagaa aaattaaaca gtaaaggaat taacgacctt     1560
atgtcaagcc ctcagatttc cgctgttgta                                      1590
```

<210> SEQ ID NO 7
<211> LENGTH: 3513
<212> TYPE: DNA
<213> ORGANISM: Arabidopsis thaliana

<400> SEQUENCE: 7

```
acctcattgc aaaacaattt ccccactatc tatcctccat aatatagtat tcctcttttc       60
tctcctacgt tctctatagt aatggcttcg ttacttctca catcttccag tatgataacc      120
actagctgtc cctccatggt tctccggtca gggttaccca tcggatcttc ttttccctct      180
cttcgcctga cccgtccata cgacaaggcg actctgttcg tctcatgttg ctccgctgag      240
tccaaaaagg tggcaactag tgctactgat ctcaaaccta tcatggaacg gaggccggag      300
tacattccga acaagcttcc ccacaagaac tatgtgcgtg tattagacac gacgcttcgt      360
gacggtgaac aatctcccgg tgcagcactt actccaccgc agaagttaga gattgccagg      420
cagctagcta aactccgagt agacatcatg gaagttggtt ttccggtgtc gtctgaggaa      480
gaattcgaag ctattaaaac catcgccaag accgtgggga acgaggttag tttctttatt      540
tccctcactt caagaaaata atataatgat ttatgttcaa actatatata gatataataa      600
```

-continued

```
aattagatgt gcaaagtgtt agttaaagaa tctcacatta gaaataagaa gtaataatct      660
atactagcat ttaaaaaata tgggccaatc tactcactaa taaatgattt tttttttaact     720 tggaagctca tgaatgctta cagaaaatta caaacacata tttagtaatt gtccaaaatt      780
gacaggaacg aaaataaact actatatatt gctgttttcc ttaggtggat gaggaaaccg      840
gttacgttcc tgtgatatgc ggcattgcac gatgcaaaaa gagagacatc gaggcaactt      900
gggaggcact gaagtatgcg aagaggccga gggtaatgct attcacatct actagtgaaa      960
ttcacatgaa atataagttg aaaaagacta aagaagaagt gatcgagatg gccgtgaaca      1020
gtgttaagta cgctaaaagc ttgggcttca aagacatcca atttgggtgc gaagatggcg      1080
gcaggtatct tgaaacttag tataactcga ttgttctttt tttccggcca ctaggtttaa      1140
cgttacaaaa tctttgttag taaacttact tttttttttt aattacgtac gtttatcttt      1200
tacaagaata ttgaaaatgt tttgattaat ttttttttgt tttataaaac aatatttaca      1260
tgcaaacaca aaagcataaa ttcaacgctg aaataatata tctcataatc taaaacgctt      1320
ttagctgatt tgttttgtga aatttaaaat tttgttttt gaaagttgtt tttatataag       1380
gtatgagaat gaaaaatata agggtgtgcc ttatacagtt atctggccca gttttgatca      1440
tgtcatatat agattttata gtatactagt ttgtgattca ggacggagaa agattttata      1500
tgtaagattc taggagaatc gataaaagcg ggtgcaacca cggtgggtt tgcggacacg       1560 gtcgggatca acatgccgca agaattcgga gaactcgtgg cctatgtcat agaaaacact      1620 ccagggctg atgatattgt cttcgccatt cattgtcata acgaccttgg tgttgctacc       1680
gccaacacaa tatccgtacg taattgctct ccctttgtct gagttagatt aatcaacaaa      1740
aattccgaac aaatttaaat tatcgaggtg acaagattaa aaatataaaa caatgatatg      1800
tatagggtat atgtgcggga gcaagacaag tcgaagtgac gatcaacgga attggtgaaa      1860
gaagtgggaa tgcgccgctt gaagaggtaa gatcgtcgtc gtgagtattt ctttggtatg      1920
tgtcggcagg gtatggtaaa gcaaaaaatt tagaagtgtg gtcttacact tctctactaa      1980
ttttatcata atttaaaaga ctaaaaaaaa gttgtcgtaa aactaaagta aaaccacata      2040
aacggtacgg ctagctagta aattatttaa tagtaacgcc ataaaagtat aaatataata      2100
atttaacatt acaataagac caacattaca atctagaagc gtttatgtgt taaaaaaaaa      2160
aaaaaaaaaa ttacaatcta gaagtaggct acaatggaat tgacatcagg aaagagagga      2220
attggaatcg aatgcttcac gtaaccctta cattaagtat ttcaaacgat agccaccaaa      2280
aagttatgta atgtgacccc taaattgcgt atttaaattg tggactagac gtacatgctt      2340
catgtgcttt atgaaaagac tggttctgtg attgtatgta ggtcgtgatg gctttgaaat      2400
gtcgaggaga atctctgatg gatggtgttt acacaaaaat agactcacgc caaattatgg      2460
ctacaagcaa gatggtacgt aacaaactag atattgaaat ttcgatattt atatgaaaac      2520
aatgatgcta atatttggcc tttatatata ataattgact aaaacgtaaa ttcttgcgca      2580
ggttcaagag catccggca tgtatgttca accacataag ccaatagttg gagacaactg       2640
ttttgttcat gagagcggca ttcaccaggt tccatatata tatatatata tatattactt      2700
atgaaaattg tatatgagat tgttgcgttg tatgtgtata attgtccaaa cattttgcag      2760
gatggaatat tgaaaaatcg aagtacatat gagatcttat caccagaaga tgttgggatc      2820
gtaaaatctg aaaattctgg cattgttctt ggaaagctta ggtaattatt ctattaagtt      2880
atgtttcttg gttttagata actataagtc taaaactatg taccatcgtc tgataaattt      2940
```

-continued

| | |
|---|---|
| atttcaacaa ctatgaaaat atgcagcgga cgtcatgctg taaaagaccg gcttaaagag | 3000 |
| gtaccacaca cacacacagt atatattagt gacttcgtac tatttttagt ctttacttat | 3060 |
| aataatcaca cacacacata tatatgggac catggcacaa tagagacttt atagagataa | 3120 |
| atatttgatt agtcatatgt tttttttttt tttttgtaat ctcaagttgg gatatgaaat | 3180 |
| cagtgatgag aaattcaacg acatcttctc acgatacaga gaattaacga aggacaaaaa | 3240 |
| ggttttcata ttatattttg tatcttctca tttacatatg cgtcaaattt gaaatattta | 3300 |
| gttatacata aaatacgaat agatttataa aattctacca aacatataaa cccccatact | 3360 |
| tacttgattt caatttgtta aactccacag agaatcacac acgctgatct gaaggcatta | 3420 |
| gtggtgaacg gtgctgaaat ctcatcagaa aaattaaaca gtaaaggaat taacgacctt | 3480 |
| atgtcaagcc ctcagatttc cgctgttgta taa | 3513 |

<210> SEQ ID NO 8
<211> LENGTH: 1586
<212> TYPE: DNA
<213> ORGANISM: Arabidopsis thaliana

<400> SEQUENCE: 8

| | |
|---|---|
| caattcccac actatctttc ctccacatta aagtaaagta tctctctctt ttttctccta | 60 |
| cgtactccat agtgatggct tcatcgcttc tgacatcttc cgttatgatc cctaccaccg | 120 |
| gttccaccgt ggttggccgg tcagtgttac cctttcaatc ttccctgcac tctctccgcc | 180 |
| tgacccattc gtacaagaac cccgcattgt tcatctcatg ttgctcttct gtgtccaaaa | 240 |
| atgcggcaac tagttctact gatctcaaac ccgttgtgga acggtggccg gagtacatac | 300 |
| cgaacaagct tcccgacgga aactatgtgc gtgtattcga cacgacgctc cgtgacggtg | 360 |
| aacaatctcc tggtggatcc ctcactccgc cgcagaagct agagattgcc cgacagctcg | 420 |
| ctaaactccg agtagacatc atggaagtcg gttttccggg atcatctgaa gaagagttag | 480 |
| aaaccattaa gaccatcgcc aagactgtgg ggaatgaggt ggatgaggaa acaggttacg | 540 |
| tccctgtgat atgcgccata gctcgatgca acatagaga cattgaggcg acttgggagg | 600 |
| cgctgaagta cgcgaagagg ccaaggatac tcgtattcac atctactagt gacattcaca | 660 |
| tgaaatataa gttgaaaaag actcaagaag aagtgattga gatggccgtg agtagtatta | 720 |
| ggtttgctaa aagcttgggc ttcaatgaca tccagtttgg gtgcgaagat ggcggcaggt | 780 |
| cggacaagga tttcctatgc aagattctag gagaagccat aaaagccggt gttacggtgg | 840 |
| tgaccatcgg tgatacggta gggatcaaca tgccacatga atacggggaa ctcgtgactt | 900 |
| atctcaaagc aaacacccct ggaattgacg atgttgtcgt cgctgttcat tgtcacaacg | 960 |
| accttggtct tgcaaccgcc aactcaatcg ccggtatacg tgcgggagca agacaggtcg | 1020 |
| aagtaactat caacggaatt ggtgaaagaa gtggcaatgc gtcgcttgag gaggtcgtga | 1080 |
| tggctttgaa atgtcgaggg gcatatgtga tcaatggggt ttacacaaaa atagacacac | 1140 |
| gccaaatcat ggctaccagc aagatggttc aagagtacac gggcttgtat gttcaagcac | 1200 |
| ataagcccat agttggagcg aactgttttg ttcatgagag cggcattcat caggttcgta | 1260 |
| attggtggag tacttatgag atcttatcac cagaagatat tgggattgta aaatctcaaa | 1320 |
| attccggcct tgttcttgga aagcttagtg gacgtcacgc tgtgaaagat cggctgaaag | 1380 |
| agttggggata tgaactcgat gatgagaaat tgaacgctgt cttctcacta ttcagagatt | 1440 |
| taaccaagaa taaaaagaga atcacggatg ctgatttgaa ggcattagta acatctagcg | 1500 |
| atgaaatctc tttggagaaa ttaaacggcg ctaacggttt aaagtctaac ggctatatac | 1560 | cagttcctca ggtttcatcg aatgtg                                           1586

<210> SEQ ID NO 9
<211> LENGTH: 4670
<212> TYPE: DNA
<213> ORGANISM: Arabidopsis thaliana

<400> SEQUENCE: 9

| | | | | | |
|---|---|---|---|---|---|
| tactagaaat | taaaattagt | aagactgact | aattacaaat | atcccaagtc | tgtgtttatt |   60 |
| ctaagacaac | tactagaaaa | cttaactata | ttagactacc | aactaggcaa | caaatatcac |  120 |
| aaagaatatc | gtatgtcacc | tacctggagg | tgcataccac | gtgattttat | ccccatttta |  180 |
| gatatggtca | tatcgattag | ttattgtata | taaaaaaaaa | attcttacag | gctataaact |  240 |
| attatgctac | aaattttggt | aaaaacctat | tacttgttat | tccgtttcca | aaacatatta |  300 |
| tggctatatt | aaagtgtgta | taaatgagtt | aaaacatttt | taacaacaaa | taaatgtaaa |  360 |
| aaaaatgagt | ttaacatcgt | tgtaagtaaa | cttaggattt | gtttgttacc | tcaaacttaa |  420 |
| atattattcc | ctctgtttct | aactaagtgt | agtttaaagg | ttttttattt | ttttcagtat |  480 |
| aagtattgtt | ttcactttc | gatgcaaaca | ttaaatgtat | ttaatagttt | ttaaccaatt |  540 |
| atattttaca | tcatatttt | tattggttgg | attagttgta | attggtgata | ttttttttaa |  600 |
| aaaagataa | atcaaatgag | atttatatat | tttcttaatt | tgcgtgcaaa | aactttaaat |  660 |
| taaaatatt | aagaaacaga | gagagtatct | tttctataca | taggtatatc | acttatatat |  720 |
| atatatatgt | atacagctaa | atatttatgt | aaaaatgtaa | acatacgaaa | ctgtttatag |  780 |
| aaagtatat | attctaaat | aagatatcaa | acacagtata | atatttaatt | ttaaagaaga |  840 |
| tactattttg | cgtttaatgt | tttcatcgaa | tataatttct | tattccgcta | actcaaatgt |  900 |
| ttattattt | taacatcaaa | atgtttctaa | tactaaaaag | tttaataaat | aaaaaaatct |  960 |
| ctctataaat | agataaatta | tatcgtataa | tgttcaaaac | aattcccaca | ctatctttcc | 1020 |
| tccacattaa | agtaaagtat | ctctctcttt | tttctcctac | gtactccata | gtgatggctt | 1080 |
| catcgcttct | gacatcttcc | gttatgatcc | ctaccaccgg | ttccaccgtg | gttggccggt | 1140 |
| cagtgttacc | ctttcaatct | tccctgcact | ctctccgcct | gacccattcg | tacaagaacc | 1200 |
| ccgcattgtt | catctcatgt | tgctcttctg | tgtccaaaaa | tgcggcaact | agttctactg | 1260 |
| atctcaaacc | cgttgtggaa | cggtggccgg | agtacatacc | gaacaagctt | cccgacggaa | 1320 |
| actatgtgcg | tgtattcgac | acgacgctcc | gtgacggtga | acaatctcct | ggtggatccc | 1380 |
| tcactccgcc | gcagaagcta | gagattgccc | gacagctcgc | taaactccga | gtagacatca | 1440 |
| tggaagtcgg | ttttccggga | tcatctgaag | aagagttaga | aaccattaag | accatcgcca | 1500 |
| agactgtggg | gaatgaggtt | ttttctttat | ttccttcact | taaatgatta | tgtacatatt | 1560 |
| ttaacacaca | aaaaaaaact | tgatataatt | ttatgttcaa | actatatata | tatagttgat | 1620 |
| aaattgcaca | tgacccttat | agttgaggcc | gaaataaaga | aaacaaatta | tgtgtttaga | 1680 |
| attttttcaa | aaacggctga | tgaatacatt | aggactattt | gtcttaattt | ataaactgta | 1740 |
| ttagtatta | aattttacta | ctaattttgc | ggtccttatt | tatttttatt | ttaatccgtt | 1800 |
| tgttgtagcc | tgctgctttt | tttgttttcc | ttcacttgga | tgtagtttta | ttcgtgtttt | 1860 |
| tttttcctac | catctattct | tctagttata | gtgttattta | taattagcca | agttctaacg | 1920 |
| ggttagagaa | agcacatgca | catgattagt | tagagccggt | cgtatagtta | agattttttt | 1980 |
| tttgtgacat | atatatgaca | aaattatgtg | taaaagtgta | agaatcccat | atatatcaga | 2040 |

```
aatacaattc tagcatatac aatatatgag ttaatattat atagtcatta ctagttggtt    2100
ttgtgttgaa actcatgaat gctcccaaat ggagcgagta acggtcaaag ttgacaacaa    2160
cgaacattaa ttactatatt gttgttttgc ttaggtggat gaggaaacag gttacgtccc    2220
tgtgatatgc gccatagctc gatgcaaaca tagagacatt gaggcgactt gggaggcgct    2280
gaagtacgcg aagaggccaa ggatactcgt attcacatct actagtgaca ttcacatgaa    2340
atataagttg aaaaagactc aagaagaagt gattgagatg gccgtgagta gtattaggtt    2400
tgctaaaagc ttgggcttca atgacatcca gtttgggtgc gaagatggcg gcaggtccaa    2460
atctttaaac ctttatatat ctcaattgtt tctctgcgtt tttggtttag ttttatttat    2520
gcttagtttg tattaccaaa ctattttgt tagtaactta tgtttgcgtt gacatttggg     2580 tatattttg gcaagaataa ttcacaaaca aaggcatga atgattgtga gttttttgt       2640 tttttttat atagttttg gtttctggat tttagaattt ggttttgga tttgcaaaa        2700 atagaaaata gataagtggg gaaaaatgt tatgttaaga atttgttcag gaaagtgaa      2760 gaactcaaat aagatggttt ttagattgtc actaaaacat tgttaagatc tttcaaacac    2820
tagatttcta gatcataata gaaaaggcgg ttttagctgt tactagatat gttatggatt    2880
ttgtgcgaat tttacatata tgatcatgtc atatatatat atatatattt gattttaaaa    2940
tatagtgtga ttcaggtcgg acaaggattt cctatgcaag attctaggag aagccataaa    3000
agccggtgtt acggtggtga ccatcggtga tacggtaggg atcaacatgc cacatgaata    3060
cggggaactc gtgacttatc tcaaagcaaa caccccctgga attgacgatg ttgtcgtcgc   3120
tgttcattgt cacaacgacc ttggtcttgc aaccgccaac tcaatcgccg tacggaacta    3180
actctttttt tgtgtgtgtg tgttagatat atttttcatat atatattttac taatatagat  3240 tctcaatgtg acaaaaatat gaacatataa aacaacgaat ttacatgata tatatatagg    3300
gtatacgtgc gggagcaaga caggtcgaag taactatcaa cggaattggt gaaagaagtg    3360
gcaatgcgtc gcttgaggag gtatcatcat ttttgttacc ataatctcat cactaccatg    3420
atcatgatca tgatcatcat tatcaacatg accatttaaa tggtatgtag gtcgtgatgg    3480 cttttgaaatg tcgagggca tatgtgatca atggggttta cacaaaaata gacacacgcc    3540
aaatcatggc taccagcaag atggtatata ttcacacatg ccatatatat acatatatat    3600
atatatatat ataattaatt aacaaaaatt tatgtaaact cttgagcagg ttcaagagta    3660
cacgggcttg tatgttcaag cacataagcc catagttgga gcgaactgtt ttgttcatga    3720
gagcggcatt catcaggttc gtaattggtg gtaaacacgg atattaagaa attatataaa    3780 ctatttaga ttttgttttt aaaatccct ttaaccaaca ctaatcgaat attctagatg      3840
tacactataa ctaaaataaa catttacatt atatatgtga taataaaaat acatacgaga    3900
ttaaattgat ttatatgatg tttgttccaa tattttttcag gatggaatat tgaaaaatag   3960
gagtacttat gagatcttat caccagaaga tattgggatt gtaaaatctc aaaattccgg    4020
ccttgttctt ggaaagctta ggttaatatt ctatttagtg atacttttac ctacgaacaa    4080 ttgtttatt tgtcttctta tatattaatt ttaacaacaa tggaaatgtg cagtggacgt     4140
cacgctgtga aagatcggct gaaagaggta ttccttgtga caattgtacc tacctactag    4200
attacacttc ctagagataa atattagatg attcatatac ttacttatgt gtatattttc    4260
tattttcagt tgggatatga actcgatgat gagaaattga acgctgtctt ctcactattc    4320
agagatttaa ccaagaataa aaaggttttc aatttctata tattttgtat ctcctcgtgc    4380
acatgcatgc aatacggttt aactaacaaa tttaatcata tatggtataa gaatgtaaga    4440
```

-continued

```
aacgaactga ttttaaagtt ttagaaaaga aaatctcaaa cttttatttt gaaaaaatat    4500
ctcgaactta atgtgttttc atttgtcaaa attttcagag aatcacggat gctgatttga    4560
aggcattagt aacatctagc gatgaaatct ctttggagaa attaaacggc gctaacggtt    4620
taaagtctaa cggctatata ccagttcctc aggtttcatc gaatgtgtaa                4670
```

<210> SEQ ID NO 10
<211> LENGTH: 516
<212> TYPE: PRT
<213> ORGANISM: Lycopersicon pennellii

<400> SEQUENCE: 10

```
Met Ala Ser Ile Thr Ala Asn His Pro Ile Ser Gly Lys Pro Leu Ile
 1               5                  10                  15

Ser Phe Arg Pro Lys Asn Pro Leu Leu Gln Thr Gln Thr Leu Phe Asn
            20                  25                  30

Phe Lys Pro Ser Ile Ser Lys His Ser Asn Ser Ser Phe Ser Ile Pro
        35                  40                  45

Val Val Arg Cys Ser Ile Arg Arg Ile Pro Glu Tyr Thr Pro Ser His
    50                  55                  60

Ile Pro Asp Pro Asn Tyr Val Arg Ile Phe Asp Thr Thr Leu Arg Asp
65                  70                  75                  80

Gly Glu Gln Ser Pro Gly Ala Thr Met Thr Thr Lys Glu Lys Leu Asp
                85                  90                  95

Val Ala Arg Gln Ser Ala Lys Leu Gly Val Asp Ile Ile Glu Ala Gly
            100                 105                 110

Phe Pro Ala Ser Ser Glu Ala Asp Leu Glu Ala Val Lys Leu Ile Ala
        115                 120                 125

Lys Glu Val Gly Asn Gly Val Tyr Glu Glu Glu Tyr Val Pro Val Ile
    130                 135                 140

Cys Gly Leu Ala Arg Cys Asn Lys Lys Asp Ile Asp Lys Ala Trp Glu
145                 150                 155                 160

Ala Val Lys Tyr Ala Lys Lys Pro Arg Ile His Thr Phe Ile Ala Thr
                165                 170                 175

Ser Glu Val His Met Asn Tyr Lys Leu Lys Met Ser Arg Asp Gln Val
            180                 185                 190

Val Glu Lys Ala Arg Ser Met Val Ala Tyr Ala Arg Ser Ile Gly Cys
        195                 200                 205

Glu Asp Val Glu Phe Ser Pro Glu Asp Ala Gly Arg Ser Asp Pro Glu
    210                 215                 220

Phe Leu Tyr His Ile Leu Gly Glu Val Ile Lys Ala Gly Ala Thr Thr
225                 230                 235                 240

Leu Asn Ile Pro Asp Thr Val Gly Tyr Thr Val Pro Glu Glu Phe Gly
                245                 250                 255

Gln Leu Ile Ala Lys Ile Lys Ala Asn Thr Pro Gly Val Glu Asp Val
            260                 265                 270

Ile Ile Ser Thr His Cys Gln Asn Asp Leu Gly Leu Ser Thr Ala Asn
        275                 280                 285

Thr Leu Ala Gly Ala Cys Ala Gly Ala Arg Gln Leu Glu Val Thr Ile
    290                 295                 300

Asn Gly Ile Gly Glu Arg Ala Gly Asn Ala Ser Leu Glu Glu Val Val
305                 310                 315                 320

Met Ala Leu Lys Cys Arg Gly Glu Gln Val Leu Gly Gly Leu Tyr Thr
                325                 330                 335
```

```
Gly Ile Asn Thr Gln His Ile Leu Met Ser Ser Lys Met Val Glu Gly
                340                 345                 350

Ile Ser Gly Leu His Val Gln Pro His Lys Ala Ile Val Gly Ala Asn
            355                 360                 365

Ala Phe Val His Glu Ser Gly Ile His Gln Asp Gly Met Leu Lys His
        370                 375                 380

Lys Asp Thr Tyr Glu Ile Ile Ser Pro Glu Asp Ile Gly Leu Asn Arg
385                 390                 395                 400

Ala Asn Glu Ser Gly Ile Val Phe Gly Lys Leu Ser Gly Val Met Leu
                405                 410                 415

Cys Lys Pro Lys Met Leu Glu Leu Gly Tyr Glu Ile Glu Gly Lys Glu
                420                 425                 430

Leu Asp Leu Phe Trp Arg Phe Lys Ser Val Ala Glu Lys Lys Lys
        435                 440                 445

Lys Ile Thr Asp Asp Asp Leu Val Ala Leu Met Ser Asp Glu Val Phe
450                 455                 460

Gln Pro Gln Phe Val Trp Gln Leu Gln Asn Val Gln Val Thr Cys Gly
465                 470                 475                 480

Ser Leu Gly Leu Ser Thr Ala Thr Val Lys Leu Ile Asp Ala Asp Gly
                485                 490                 495

Arg Glu His Ile Ser Cys Ser Val Gly Thr Gly Pro Val Asp Ala Ala
                500                 505                 510

Tyr Lys Ala Val
        515

<210> SEQ ID NO 11
<211> LENGTH: 478
<212> TYPE: PRT
<213> ORGANISM: Glycine max

<400> SEQUENCE: 11

Met Pro Thr Lys Thr Ser Thr Pro Ser Ser Gln Ser Pro Lys Leu Ser
1               5                   10                  15

His Leu Arg Pro Gln Tyr Ile Pro Asn His Ile Pro Asp Ser Ser Tyr
            20                  25                  30

Val Arg Ile Leu Asp Thr Thr Leu Arg Asp Gly Glu Gln Ser Pro Gly
        35                  40                  45

Ala Thr Met Thr Ala Lys Glu Lys Leu Asp Ile Ala Arg Gln Leu Val
    50                  55                  60

Lys Leu Gly Val Asp Ile Ile Gln Pro Gly Phe Pro Ser Ala Ser Asn
65                  70                  75                  80

Ser Asp Phe Met Ala Val Lys Met Ile Ala Gln Glu Val Gly Asn Ala
                85                  90                  95

Val Asp Asp Asp Gly Tyr Val Pro Val Ile Gly Phe Cys Arg Cys
            100                 105                 110

Val Glu Lys Asp Ile Ser Thr Ala Trp Glu Ala Val Lys Tyr Ala Lys
        115                 120                 125

Arg Pro Arg Leu Cys Thr Ser Ile Ala Thr Ser Pro Ile His Met Glu
    130                 135                 140

His Lys Leu Arg Lys Ser Lys Asp Gln Val Ile Gln Ile Ala Arg Asp
145                 150                 155                 160

Met Val Lys Phe Ala Arg Ser Leu Gly Cys Asn Asp Ile Gln Phe Gly
                165                 170                 175

Ala Glu Asp Ala Thr Arg Ser Asp Arg Glu Phe Leu Tyr Glu Ile Leu
```

```
                    180                 185                 190
Gly Val Val Ile Glu Ala Gly Ala Thr Thr Val Asn Ile Ala Asp Thr
                195                 200                 205

Val Gly Ile Val Met Pro Leu Glu Leu Gly Lys Leu Ile Val Asp Ile
            210                 215                 220

Lys Asp Asn Thr Pro Gly Ile Ala Asn Val Ile Ile Ser Thr His Cys
225                 230                 235                 240

His Asn Asp Leu Gly Leu Ala Thr Ala Asn Thr Ile Glu Gly Ala Arg
                245                 250                 255

Thr Gly Ala Arg Gln Leu Glu Val Thr Ile Asn Gly Ile Gly Glu Arg
            260                 265                 270

Ala Gly Asn Ala Ser Leu Glu Glu Val Val Met Ala Leu Ala Ser Lys
                275                 280                 285

Gly Asp His Ala Leu Asn Gly Leu Tyr Thr Arg Ile Asn Thr Arg His
            290                 295                 300

Ile Leu Glu Thr Ser Lys Met Val Glu Glu Tyr Ser Gly Met His Leu
305                 310                 315                 320

Gln Pro His Lys Pro Leu Val Gly Ala Asn Ala Phe Val His Ala Ser
                325                 330                 335

Gly Ile His Gln Asp Gly Met Leu Lys His Lys Gly Thr Tyr Glu Thr
            340                 345                 350

Ile Ser Pro Glu Glu Ile Gly His Lys Arg Thr Thr Arg Ile Gly Ile
            355                 360                 365

Val Leu Gly Lys Leu Ser Gly Ser Gln Ala Leu Arg Lys Arg Leu Glu
            370                 375                 380

Glu Leu Gly Tyr Asp Leu Lys Glu Asp Glu Val Asp Ser Val Phe Trp
385                 390                 395                 400

Gln Phe Lys Ala Met Ala Glu Lys Lys Val Val Thr Asp Val Asp
                405                 410                 415

Leu Lys Ala Leu Val Ser Tyr Lys Ala Phe His Ala Glu Ser Ile Trp
            420                 425                 430

Lys Leu Gly Asp Leu Gln Val Thr Cys Gly Thr Ile Gly Leu Ser Thr
            435                 440                 445

Ala Thr Val Lys Leu Val Asn Ile Asp Gly Ser Thr His Val Ala Cys
450                 455                 460

Ser Ile Gly Ile Gly Ala Val Asp Ser Thr Tyr Lys Ala Ile
465                 470                 475

<210> SEQ ID NO 12
<211> LENGTH: 390
<212> TYPE: PRT
<213> ORGANISM: Rhodobacter sphaeroides

<400> SEQUENCE: 12

Met Ser Arg Gln Gln Pro Arg Ser Phe Leu Pro Glu Ser Pro Leu Ala
1               5                   10                  15

Pro Val Ala Leu Cys Asp Thr Thr Leu Arg Asp Gly Glu Gln Thr Ala
            20                  25                  30

Gly Val Ala Phe Thr Arg Ala Glu Lys Arg Ala Ile Ala Glu Ala Leu
        35                  40                  45

Gln Ala Ala Gly Val Ala Val Glu Val Gly Val Pro Ala Met Gly
    50                  55                  60

Glu Glu Glu Arg Ala Asp Ile Arg Ala Val Ala Ala Val Leu Lys Thr
65                  70                  75                  80
```

-continued

```
Ala Ala Pro Val Val Trp Cys Arg Leu Arg Ala Glu Asp Leu Ala Ala
             85                  90                  95

Ala Gln Arg Thr Gly Val Val Arg Leu His Ile Gly Val Pro Val Ser
            100                 105                 110

Glu Arg Gln Ile Ser Ala Lys Leu Gly Lys Asp Ala Ala Trp Val Arg
        115                 120                 125

Asp Lys Val Glu Lys Leu Val Arg Ala Ala Ser Trp Ala Gly His Lys
    130                 135                 140

Val Ser Val Gly Ala Glu Asp Ala Ser Arg Ala Asp Pro Phe Phe Leu
145                 150                 155                 160

Ala Glu Ile Ala His Val Ala Ala Glu Ala Gly Ala Ile Arg Phe Arg
                165                 170                 175

Ile Ser Asp Thr Leu Gly Val Leu Asp Pro Phe Ala Ala His Glu Leu
            180                 185                 190

Val Gly Arg Val Val Thr Arg Cys Pro Leu Pro Val Glu Phe His Gly
        195                 200                 205

His Asn Asp Leu Gly Met Ala Thr Ala Asn Ser Leu Ala Ala Ala Arg
    210                 215                 220

Ala Gly Ala Ser His Leu Ser Val Thr Val Asn Gly Leu Gly Glu Arg
225                 230                 235                 240

Ala Gly Asn Ala Ala Leu Glu Glu Val Ala Ala Leu Glu Ala Ala
                245                 250                 255

Gly Arg Ala Thr Gly Val Ala Leu Gly Gln Leu Cys Ala Leu Ser Glu
                260                 265                 270

Leu Val Ala Arg Ala Ser Gly Arg Pro Leu Ser Pro Gln Lys Pro Ile
            275                 280                 285

Val Gly Glu Gly Val Phe Thr His Glu Cys Gly Ile His Val Asp Gly
        290                 295                 300

Leu Met Lys Asp Arg Ala Thr Tyr Glu Ser Ala Asp Leu Arg Pro Glu
305                 310                 315                 320

Arg Phe Gly Arg Ser His Arg Ile Ala Ile Gly Lys His Ser Ser Ala
                325                 330                 335

Ala Gly Leu Ala Arg Ala Leu Ala Glu Ala Gly Leu Pro Ala Asp Ala
            340                 345                 350

Ala Thr Leu Ala Ala Leu Met Pro Ala Leu Arg Asp Trp Ala Ala Ile
        355                 360                 365

Thr Lys Arg Ala Ala Ala Pro Glu Asp Leu Ala Ala Leu Leu Ala Ala
    370                 375                 380

Gln Thr Glu Thr Ala Arg
385                 390
```

<210> SEQ ID NO 13
<211> LENGTH: 612
<212> TYPE: PRT
<213> ORGANISM: Lycopersicon pennellii

<400> SEQUENCE: 13

```
Met Ala Ser Ile Thr Ala Asn His Pro Ile Ser Gly Lys Pro Leu Ile
  1               5                  10                  15

Ser Phe Arg Pro Lys Asn Pro Leu Leu Gln Thr Gln Thr Leu Phe Asn
             20                  25                  30

Phe Lys Pro Ser Ile Ser Lys His Ser Asn Ser Ser Phe Ser Ile Pro
         35                  40                  45

Val Val Arg Cys Ser Ile Arg Arg Ile Pro Glu Tyr Thr Pro Ser His
     50                  55                  60
```

-continued

```
Ile Pro Asp Pro Asn Tyr Val Arg Ile Phe Asp Thr Thr Leu Arg Asp
 65                  70                  75                  80

Gly Glu Gln Ser Pro Gly Ala Thr Met Thr Thr Lys Glu Lys Leu Asp
                 85                  90                  95

Val Ala Arg Gln Ser Ala Lys Leu Gly Val Asp Ile Ile Glu Ala Gly
            100                 105                 110

Phe Pro Ala Ser Ser Glu Ala Asp Leu Glu Ala Val Lys Leu Ile Ala
        115                 120                 125

Lys Glu Val Gly Asn Gly Val Tyr Glu Glu Tyr Val Pro Val Ile
    130                 135                 140

Cys Gly Leu Ala Arg Cys Asn Lys Lys Asp Ile Asp Lys Ala Trp Glu
145                 150                 155                 160

Ala Val Lys Tyr Ala Lys Lys Pro Arg Ile His Thr Phe Ile Ala Thr
                165                 170                 175

Ser Glu Val His Met Asn Tyr Lys Leu Lys Met Ser Arg Asp Gln Val
            180                 185                 190

Val Glu Lys Ala Arg Ser Met Val Ala Tyr Ala Arg Ser Ile Gly Cys
        195                 200                 205

Glu Asp Val Glu Phe Ser Pro Glu Asp Ala Gly Arg Ser Asp Pro Glu
    210                 215                 220

Phe Leu Tyr His Ile Leu Gly Glu Val Ile Lys Ala Gly Ala Thr Thr
225                 230                 235                 240

Leu Asn Ile Pro Asp Thr Val Gly Tyr Thr Val Pro Glu Glu Phe Gly
                245                 250                 255

Gln Leu Ile Ala Lys Ile Lys Ala Asn Thr Pro Gly Val Glu Asp Val
            260                 265                 270

Ile Ile Ser Thr His Cys Gln Asn Asp Leu Gly Leu Ser Thr Ala Asn
        275                 280                 285

Thr Leu Ala Gly Ala Cys Ala Gly Ala Arg Gln Leu Glu Val Thr Ile
    290                 295                 300

Asn Gly Ile Gly Glu Arg Ala Gly Asn Ala Ser Leu Glu Glu Val Val
305                 310                 315                 320

Met Ala Leu Lys Cys Arg Gly Glu Gln Val Leu Gly Gly Leu Tyr Thr
                325                 330                 335

Gly Ile Asn Thr Gln His Ile Leu Met Ser Ser Lys Met Val Glu Gly
            340                 345                 350

Ile Ser Gly Leu His Val Gln Pro His Lys Ala Ile Val Gly Ala Asn
        355                 360                 365

Ala Phe Val His Glu Ser Gly Ile His Gln Asp Gly Met Leu Lys His
    370                 375                 380

Lys Asp Thr Tyr Glu Ile Ile Ser Pro Glu Asp Ile Gly Leu Asn Arg
385                 390                 395                 400

Ala Asn Glu Ser Gly Ile Val Phe Gly Lys Leu Ser Gly Val Met Leu
                405                 410                 415

Cys Lys Pro Lys Met Leu Glu Leu Gly Tyr Glu Ile Glu Gly Lys Glu
            420                 425                 430

Leu Asp Asp Leu Phe Trp Arg Phe Lys Ser Val Ala Glu Lys Lys Lys
    435                 440                 445

Lys Ile Thr Asp Asp Leu Val Ala Leu Met Ser Asp Glu Val Phe
450                 455                 460

Gln Pro Gln Phe Val Trp Gln Leu Gln Asn Val Gln Val Thr Cys Gly
465                 470                 475                 480
```

```
Ser Leu Gly Leu Ser Thr Ala Thr Val Lys Leu Ile Asp Ala Asp Gly
            485                 490                 495

Arg Glu His Ile Ser Cys Ser Val Gly Thr Gly Pro Val Asp Ala Ala
            500                 505                 510

Tyr Lys Ala Val Asp Leu Ile Val Lys Val Pro Val Thr Leu Leu Glu
            515                 520                 525

Tyr Ser Met Asn Ala Val Thr Gln Gly Ile Asp Ala Ile Ala Ser Thr
            530                 535                 540

Arg Val Leu Ile Arg Gly Glu Asn Gly His Thr Ser Thr His Ala Leu
545                 550                 555                 560

Thr Gly Glu Thr Val His Arg Thr Phe Ser Gly Thr Gly Ala Asp Met
            565                 570                 575

Asp Ile Val Ile Ser Ser Val Arg Ala Tyr Val Gly Ala Leu Asn Lys
            580                 585                 590

Met Met Ser Phe Arg Lys Leu Met Ala Lys Asn Asn Lys Pro Glu Ser
            595                 600                 605

Ser Ala Val Ile
            610

<210> SEQ ID NO 14
<211> LENGTH: 565
<212> TYPE: PRT
<213> ORGANISM: Glycine max

<400> SEQUENCE: 14

Met Pro Thr Lys Thr Ser Thr Pro Ser Ser Gln Ser Pro Lys Leu Ser
1               5                   10                  15

His Leu Arg Pro Gln Tyr Ile Pro Asn His Ile Pro Asp Ser Ser Tyr
            20                  25                  30

Val Arg Ile Leu Asp Thr Thr Leu Arg Asp Gly Glu Gln Ser Pro Gly
            35                  40                  45

Ala Thr Met Thr Ala Lys Glu Lys Leu Asp Ile Ala Arg Gln Leu Val
        50                  55                  60

Lys Leu Gly Val Asp Ile Ile Gln Pro Gly Phe Pro Ser Ala Ser Asn
65                  70                  75                  80

Ser Asp Phe Met Ala Val Lys Met Ile Ala Gln Glu Val Gly Asn Ala
            85                  90                  95

Val Asp Asp Asp Gly Tyr Val Pro Val Ile Ala Gly Phe Cys Arg Cys
            100                 105                 110

Val Glu Lys Asp Ile Ser Thr Ala Trp Glu Ala Val Lys Tyr Ala Lys
            115                 120                 125

Arg Pro Arg Leu Cys Thr Ser Ile Ala Thr Ser Pro Ile His Met Glu
        130                 135                 140

His Lys Leu Arg Lys Ser Lys Asp Gln Val Ile Gln Ile Ala Arg Asp
145                 150                 155                 160

Met Val Lys Phe Ala Arg Ser Leu Gly Cys Asn Asp Ile Gln Phe Gly
            165                 170                 175

Ala Glu Asp Ala Thr Arg Ser Asp Arg Glu Phe Leu Tyr Glu Ile Leu
            180                 185                 190

Gly Val Val Ile Glu Ala Gly Ala Thr Thr Val Asn Ile Ala Asp Thr
            195                 200                 205

Val Gly Ile Val Met Pro Leu Glu Leu Gly Lys Leu Ile Val Asp Ile
        210                 215                 220

Lys Asp Asn Thr Pro Gly Ile Ala Asn Val Ile Ile Ser Thr His Cys
225                 230                 235                 240
```

```
His Asn Asp Leu Gly Leu Ala Thr Ala Asn Thr Ile Glu Gly Ala Arg
            245                 250                 255

Thr Gly Ala Arg Gln Leu Glu Val Thr Ile Asn Gly Ile Gly Glu Arg
        260                 265                 270

Ala Gly Asn Ala Ser Leu Glu Glu Val Val Met Ala Leu Ala Ser Lys
        275                 280                 285

Gly Asp His Ala Leu Asn Gly Leu Tyr Thr Arg Ile Asn Thr Arg His
        290                 295                 300

Ile Leu Glu Thr Ser Lys Met Val Glu Tyr Ser Gly Met His Leu
305                 310                 315                 320

Gln Pro His Lys Pro Leu Val Gly Ala Asn Ala Phe Val His Ala Ser
                325                 330                 335

Gly Ile His Gln Asp Gly Met Leu Lys His Lys Gly Thr Tyr Glu Thr
        340                 345                 350

Ile Ser Pro Glu Glu Ile Gly His Lys Arg Thr Thr Arg Ile Gly Ile
        355                 360                 365

Val Leu Gly Lys Leu Ser Gly Ser Gln Ala Leu Arg Lys Arg Leu Glu
    370                 375                 380

Glu Leu Gly Tyr Asp Leu Lys Glu Asp Glu Val Asp Ser Val Phe Trp
385                 390                 395                 400

Gln Phe Lys Ala Met Ala Glu Lys Lys Val Val Thr Asp Val Asp
                405                 410                 415

Leu Lys Ala Leu Val Ser Tyr Lys Ala Phe His Ala Glu Ser Ile Trp
            420                 425                 430

Lys Leu Gly Asp Leu Gln Val Thr Cys Gly Thr Ile Gly Leu Ser Thr
        435                 440                 445

Ala Thr Val Lys Leu Val Asn Ile Asp Gly Ser Thr His Val Ala Cys
        450                 455                 460

Ser Ile Gly Ile Gly Ala Val Asp Ser Thr Tyr Lys Ala Ile Asn Leu
465                 470                 475                 480

Ile Val Lys Glu Pro Thr Lys Leu Leu Asp Tyr Ser Leu Asn Ser Val
                485                 490                 495

Thr Glu Gly Ile Gly Val Asn Val Thr Ala Arg Val Ile Cys Arg
            500                 505                 510

Glu Asn Asn His Thr Ser Thr Tyr Ala Phe Thr Glu Asp Ala Asn Tyr
            515                 520                 525

Pro Thr Phe Ser Gly Ile Ala Ala Glu Met Asp Val Val Ser Thr
        530                 535                 540

Val Lys Ala Tyr Leu Val Ala Leu Asn Lys Leu Leu Arg Trp Lys Glu
545                 550                 555                 560

Ser Phe Arg Cys Ala
            565

<210> SEQ ID NO 15
<211> LENGTH: 391
<212> TYPE: PRT
<213> ORGANISM: Rhodobacter sphaeroides

<400> SEQUENCE: 15

Met Ser Arg Gln Gln Pro Arg Ala Ser Phe Leu Pro Glu Ser Pro Leu
  1               5                  10                  15

Ala Pro Val Ala Leu Cys Asp Thr Thr Leu Arg Asp Gly Glu Gln Thr
            20                  25                  30

Ala Gly Val Ala Phe Thr Arg Ala Glu Lys Arg Ala Ile Ala Glu Ala
```

```
            35                  40                  45
Leu Gln Ala Ala Gly Val Ala Glu Val Glu Val Gly Val Pro Ala Met
 50                  55                  60
Gly Glu Glu Arg Ala Asp Ile Arg Ala Val Ala Ala Val Leu Lys
 65                  70                  75                  80
Thr Ala Ala Pro Val Val Trp Cys Arg Leu Arg Ala Glu Asp Leu Ala
                 85                  90                  95
Ala Ala Gln Arg Thr Gly Val Val Arg Leu His Ile Gly Val Pro Val
                100                 105                 110
Ser Glu Arg Gln Ile Ser Ala Lys Leu Gly Lys Asp Ala Ala Trp Val
                115                 120                 125
Arg Asp Lys Val Glu Lys Leu Val Arg Ala Ala Ser Trp Ala Gly His
130                 135                 140
Lys Val Ser Val Gly Ala Glu Asp Ala Ser Arg Ala Asp Pro Phe Phe
145                 150                 155                 160
Leu Ala Glu Ile Ala His Val Ala Glu Ala Gly Ala Ile Arg Phe
                165                 170                 175
Arg Ile Ser Asp Thr Leu Gly Val Leu Asp Pro Phe Ala Ala His Glu
                180                 185                 190
Leu Val Gly Arg Val Val Thr Arg Cys Pro Leu Pro Val Glu Phe His
                195                 200                 205
Gly His Asn Asp Leu Gly Met Ala Thr Ala Asn Ser Leu Ala Ala Ala
                210                 215                 220
Arg Ala Gly Ala Ser His Leu Ser Val Thr Val Asn Gly Leu Gly Glu
225                 230                 235                 240
Arg Ala Gly Asn Ala Ala Leu Glu Glu Val Ala Ala Ala Leu Glu Ala
                245                 250                 255
Ala Gly Arg Ala Thr Gly Val Ala Leu Gly Gln Leu Cys Ala Leu Ser
                260                 265                 270
Glu Leu Val Ala Arg Ala Ser Gly Arg Pro Leu Ser Pro Gln Lys Pro
                275                 280                 285
Ile Val Gly Glu Gly Val Phe Thr His Glu Cys Gly Ile His Val Asp
                290                 295                 300
Gly Leu Met Lys Asp Arg Ala Thr Tyr Glu Ser Ala Asp Leu Arg Pro
305                 310                 315                 320
Glu Arg Phe Gly Arg Ser His Arg Ile Ala Ile Gly Lys His Ser Ser
                325                 330                 335
Ala Ala Gly Leu Ala Arg Ala Leu Ala Glu Ala Gly Leu Pro Ala Asp
                340                 345                 350
Ala Ala Thr Leu Ala Ala Leu Met Pro Ala Leu Arg Asp Trp Ala Ala
                355                 360                 365
Ile Thr Lys Arg Ala Ala Pro Glu Asp Leu Ala Ala Leu Leu Ala
                370                 375                 380
Ala Gln Thr Glu Thr Ala Arg
385                 390

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 16
atggttctcc ggtcagggtt a                                              21
```

```
<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 17
cacggtcttg gcgatggttt t                                        21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 18
aaaaccatcg ccaagaccgt g                                        21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 19
tcttcgcacc caaattggat g                                        21

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 20
acagcccaac aatggcg                                             17

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 21
cagtgatgag aaattcaacg ac                                       22

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 22
tacaacagcg gaaatctgag                                          20

<210> SEQ ID NO 23
<211> LENGTH: 520
<212> TYPE: PRT
<213> ORGANISM: Artificial Sequence
<220> FEATURE:
```

-continued

```
<221> NAME/KEY: SITE
<222> LOCATION: 1..37, 39..43, 45..57, 59, 61, 63..65, 67..69, 73..76
<223> OTHER INFORMATION: Xaa is uncertain
<220> FEATURE:
<221> NAME/KEY: SITE
<222> LOCATION: 90..91, 93..94, 98, 104, 111, 113, 117..118, 121..124
<223> OTHER INFORMATION: Xaa is uncertain
<220> FEATURE:
<221> NAME/KEY: SITE
<222> LOCATION: 126, 128, 131..132, 136, 138..142, 148, 150..151,
<223> OTHER INFORMATION: Xaa is uncertain
<220> FEATURE:
<221> NAME/KEY: SITE
<222> LOCATION: 154..156, 159..160, 165, 170, 173..178, 182, 185..186
<223> OTHER INFORMATION: Xaa is uncertain
<220> FEATURE:
<221> NAME/KEY: SITE
<222> LOCATION: 189, 191..194, 196..198, 200..202, 204..205, 207, 209
<223> OTHER INFORMATION: Xaa is uncertain
<220> FEATURE:
<221> NAME/KEY: SITE
<222> LOCATION: 211..212, 214..215, 218, 222, 224, 226..227, 230..231
<223> OTHER INFORMATION: Xaa is uncertain
<220> FEATURE:
<221> NAME/KEY: SITE
<222> LOCATION: 235..236, 238, 244..245, 247, 252..254, 256, 258, 260
<223> OTHER INFORMATION: Xaa is uncertain
<220> FEATURE:
<221> NAME/KEY: SITE
<222> LOCATION: 262..267, 272..279, 287, 293..294, 297, 318, 327..329
<223> OTHER INFORMATION: Xaa is uncertain
<220> FEATURE:
<221> NAME/KEY: SITE
<222> LOCATION: 331..335, 337, 340, 342..345, 347..349, 354..356
<223> OTHER INFORMATION: Xaa is uncertain
<220> FEATURE:
<221> NAME/KEY: SITE
<222> LOCATION: 359..361, 370, 372, 384, 387..389, 393..394, 398..399
<223> OTHER INFORMATION: Xaa is uncertain
<220> FEATURE:
<221> NAME/KEY: SITE
<222> LOCATION: 401..402, 404..407, 411, 417..423, 425, 430..439
<223> OTHER INFORMATION: Xaa is uncertain
<220> FEATURE:
<221> NAME/KEY: SITE
<222> LOCATION: 441..446, 448..450, 453..454, 457, 460, 463..499
<223> OTHER INFORMATION: Xaa is uncertain
<220> FEATURE:
<221> NAME/KEY: SITE
<222> LOCATION: 501..506, 508..512, 514..520
<223> OTHER INFORMATION: Xaa is uncertain
<220> FEATURE:
<223> OTHER INFORMATION: Description of Artificial Sequence: Consensus

<400> SEQUENCE: 23

Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Ser Xaa Xaa Xaa Xaa Ser Xaa Xaa Xaa Xaa
         35                  40                  45

Xaa Xaa Xaa Xaa Xaa Xaa Xaa Xaa Pro Xaa Tyr Xaa Pro Xaa Xaa
     50                  55                  60

Xaa Pro Xaa Xaa Xaa Tyr Val Arg Xaa Xaa Xaa Asp Thr Thr Leu
 65                  70                  75                  80

Arg Asp Gly Glu Gln Ser Pro Gly Ala Xaa Xaa Thr Xaa Xaa Glu Lys
                 85                  90                  95

Leu Xaa Ile Ala Arg Gln Leu Xaa Lys Leu Gly Val Asp Ile Xaa Glu
             100                 105                 110

Xaa Gly Phe Pro Xaa Xaa Ser Glu Xaa Xaa Xaa Xaa Ala Xaa Lys Xaa
         115                 120                 125
```

-continued

```
Ile Ala Xaa Xaa Val Gly Asn Xaa Val Xaa Xaa Xaa Xaa Tyr Val
    130                 135                 140

Pro Val Ile Xaa Gly Xaa Xaa Arg Cys Xaa Xaa Xaa Asp Ile Xaa Xaa
145             150                 155                 160

Ala Trp Glu Ala Xaa Lys Tyr Ala Lys Xaa Pro Arg Xaa Xaa Xaa Xaa
                165             170                 175

Xaa Xaa Thr Ser Glu Xaa His Met Xaa Xaa Lys Leu Xaa Lys Xaa Xaa
            180             185                 190

Xaa Xaa Val Xaa Xaa Xaa Ala Xaa Xaa Xaa Val Xaa Xaa Ala Xaa Ser
            195             200             205

Xaa Gly Xaa Xaa Asp Xaa Xaa Phe Gly Xaa Glu Asp Ala Xaa Arg Xaa
    210             215             220

Asp Xaa Xaa Phe Leu Xaa Xaa Ile Leu Gly Xaa Xaa Ile Xaa Ala Gly
225             230             235                 240

Ala Thr Thr Xaa Xaa Ile Xaa Asp Thr Val Gly Xaa Xaa Xaa Pro Xaa
                245             250             255

Glu Xaa Gly Xaa Leu Xaa Xaa Xaa Xaa Xaa Xaa Asn Thr Pro Gly Xaa
        260             265             270

Xaa Xaa Xaa Xaa Xaa Xaa Xaa His Cys His Asn Asp Leu Gly Xaa Ala
            275             280             285

Thr Ala Asn Thr Xaa Xaa Gly Ala Xaa Ala Gly Ala Arg Gln Leu Glu
    290             295             300

Val Thr Ile Asn Gly Ile Gly Glu Arg Ala Gly Asn Ala Xaa Leu Glu
305             310             315                 320

Glu Val Val Met Ala Leu Xaa Xaa Xaa Gly Xaa Xaa Xaa Xaa Xaa Gly
                325             330             335

Xaa Tyr Thr Xaa Ile Xaa Xaa Xaa Xaa Ile Xaa Xaa Xaa Ser Lys Met
            340             345             350

Val Xaa Xaa Xaa Ser Gly Xaa Xaa Xaa Gln Pro His Lys Pro Ile Val
        355             360             365

Gly Xaa Asn Xaa Phe Val His Glu Ser Gly Ile His Gln Asp Gly Xaa
    370             375             380

Leu Lys Xaa Xaa Xaa Thr Tyr Glu Xaa Xaa Ser Pro Glu Xaa Xaa Gly
385             390             395                 400

Xaa Xaa Arg Xaa Xaa Xaa Xaa Gly Ile Val Xaa Gly Lys Leu Ser Gly
            405             410             415

Xaa Xaa Xaa Xaa Xaa Xaa Xaa Leu Xaa Glu Leu Gly Tyr Xaa Xaa Xaa
            420             425             430

Xaa Xaa Xaa Xaa Xaa Xaa Xaa Phe Xaa Xaa Xaa Xaa Xaa Xaa Ala Xaa
            435             440             445

Xaa Xaa Lys Lys Xaa Xaa Thr Asp Xaa Asp Leu Xaa Ala Leu Xaa Xaa
    450             455             460

Xaa Xaa Xaa Xaa Xaa Xaa Xaa Xaa Xaa Xaa Xaa Xaa Xaa Xaa Xaa Xaa
465             470             475                 480

Xaa Xaa Xaa Xaa Xaa Xaa Xaa Xaa Xaa Xaa Xaa Xaa Xaa Xaa Xaa Xaa
            485             490             495

Xaa Xaa Xaa Gly Xaa Xaa Xaa Xaa Xaa Ser Xaa Xaa Xaa Xaa Xaa Xaa
            500             505             510

Val Xaa Xaa Xaa Xaa Xaa Xaa Xaa
            515             520
```

<210> SEQ ID NO 24
<211> LENGTH: 630

-continued

```
<212> TYPE: PRT
<213> ORGANISM: Artificial Sequence
<220> FEATURE:
<221> NAME/KEY: SITE
<222> LOCATION: 4, 10, 13, 15..19, 21, 24, 27, 32, 38, 41..44, 47, 53,
      56
<223> OTHER INFORMATION: Xaa is uncertain
<220> FEATURE:
<221> NAME/KEY: SITE
<222> LOCATION: 61..63, 67, 69..70, 80..81, 89..90, 104..105, 108, 112
<223> OTHER INFORMATION: Xaa is uncertain
<220> FEATURE:
<221> NAME/KEY: SITE
<222> LOCATION: 125, 137, 146, 150, 173, 175, 179, 187, 191..192, 205
<223> OTHER INFORMATION: Xaa is uncertain
<220> FEATURE:
<221> NAME/KEY: SITE
<222> LOCATION: 207..208, 212, 214, 216, 218..219, 221, 225, 232, 240..
      241
<223> OTHER INFORMATION: Xaa is uncertain
<220> FEATURE:
<221> NAME/KEY: SITE
<222> LOCATION: 244..245, 250, 270, 279, 290..292, 346, 351, 354, 356,
      361
<223> OTHER INFORMATION: Xaa is uncertain
<220> FEATURE:
<221> NAME/KEY: SITE
<222> LOCATION: 368, 373..374, 386, 402, 408, 419..420, 434, 445, 449,
      451..453
<223> OTHER INFORMATION: Xaa is uncertain
<220> FEATURE:
<221> NAME/KEY: SITE
<222> LOCATION: 455, 462, 479..481, 483, 485..487, 489, 491..496, 498,
      501
<223> OTHER INFORMATION: Xaa is uncertain
<220> FEATURE:
<221> NAME/KEY: SITE
<222> LOCATION: 512, 517..518, 524, 526, 529..530, 534..535, 540, 542..
      543
<223> OTHER INFORMATION: Xaa is uncertain
<220> FEATURE:
<221> NAME/KEY: SITE
<222> LOCATION: 546, 549, 551, 554, 557..562, 565, 567..568, 571, 576
<223> OTHER INFORMATION: Xaa is uncertain
<220> FEATURE:
<221> NAME/KEY: SITE
<222> LOCATION: 578, 580..585, 590..591, 593, 596, 598, 600, 602, 605..
      606
<223> OTHER INFORMATION: Xaa is uncertain
<220> FEATURE:
<221> NAME/KEY: SITE
<222> LOCATION: 611..621
<223> OTHER INFORMATION: Xaa is uncertain
<220> FEATURE:
<223> OTHER INFORMATION: Description of Artificial Sequence: Consensus

<400> SEQUENCE: 24

Met Ala Ser Xaa Leu Leu Thr Ser Ser Xaa Met Ile Xaa Thr Xaa Xaa
 1               5                  10                  15

Xaa Xaa Xaa Val Xaa Arg Ser Xaa Leu Pro Xaa Gly Ser Ser Leu Xaa
                20                  25                  30

Ser Leu Arg Leu Thr Xaa Pro Tyr Xaa Xaa Xaa Xaa Leu Phe Xaa Ser
            35                  40                  45

Cys Cys Ser Ser Xaa Ser Lys Xaa Ser Ala Thr Ser Xaa Xaa Xaa Thr
50                  55                  60

Asp Leu Xaa Pro Xaa Xaa Glu Arg Arg Pro Glu Tyr Ile Pro Asn Xaa
65                  70                  75                  80

Xaa Pro Asp Pro Asn Tyr Val Arg Xaa Xaa Asp Thr Thr Leu Arg Asp
                85                  90                  95

Gly Glu Gln Ser Pro Gly Ala Xaa Xaa Thr Pro Xaa Glu Lys Leu Xaa
            100                 105                 110
```

-continued

```
Ile Ala Arg Gln Leu Ala Lys Leu Gly Val Asp Ile Xaa Glu Val Gly
        115                 120                 125

Phe Pro Ala Ser Ser Glu Glu Glu Xaa Glu Ala Ile Lys Thr Ile Ala
    130                 135                 140

Lys Xaa Val Gly Asn Xaa Val Asp Glu Glu Thr Gly Tyr Val Pro Val
145                 150                 155                 160

Ile Cys Gly Ile Ala Arg Cys Lys Lys Arg Asp Ile Xaa Ala Xaa Trp
                165                 170                 175

Glu Ala Xaa Lys Tyr Ala Lys Arg Pro Arg Xaa His Thr Phe Xaa Xaa
            180                 185                 190

Thr Ser Glu Ile His Met Lys Tyr Lys Leu Lys Lys Xaa Lys Xaa Xaa
        195                 200                 205

Val Ile Glu Xaa Ala Xaa Ser Xaa Val Xaa Xaa Ala Xaa Ser Leu Gly
    210                 215                 220

Xaa Asn Asp Ile Gln Phe Gly Xaa Glu Asp Ala Gly Arg Ser Asp Xaa
225                 230                 235                 240

Xaa Phe Leu Xaa Xaa Ile Leu Gly Glu Xaa Ile Lys Ala Gly Ala Thr
                245                 250                 255

Thr Val Asn Ile Ala Asp Thr Val Gly Ile Asn Met Pro Xaa Glu Phe
            260                 265                 270

Gly Glu Leu Val Ala Tyr Xaa Lys Ala Asn Thr Pro Gly Ile Asp Asp
        275                 280                 285

Val Xaa Xaa Xaa Thr His Cys His Asn Asp Leu Gly Leu Ala Thr Ala
    290                 295                 300

Asn Thr Ile Ala Gly Ala Arg Ala Gly Ala Arg Gln Leu Glu Val Thr
305                 310                 315                 320

Ile Asn Gly Ile Gly Glu Arg Ala Gly Asn Ala Ser Leu Glu Glu Val
                325                 330                 335

Val Met Ala Leu Lys Cys Arg Gly Glu Xaa Val Leu Asn Gly Xaa Tyr
            340                 345                 350

Thr Xaa Ile Xaa Thr Arg Gln Ile Xaa Ala Thr Ser Lys Met Val Xaa
        355                 360                 365

Glu Tyr Ser Gly Xaa Xaa Val Gln Pro His Lys Pro Ile Val Gly Ala
    370                 375                 380

Asn Xaa Phe Val His Glu Ser Gly Ile His Gln Asp Gly Met Leu Lys
385                 390                 395                 400

His Xaa Ser Thr Tyr Glu Ile Xaa Ser Pro Glu Asp Ile Gly Ile Val
                405                 410                 415

Arg Ser Xaa Xaa Ser Gly Ile Val Leu Gly Lys Leu Ser Gly Arg His
            420                 425                 430

Ala Xaa Lys Asp Arg Leu Lys Glu Leu Gly Tyr Glu Xaa Asp Asp Glu
        435                 440                 445

Xaa Leu Xaa Xaa Xaa Phe Xaa Arg Phe Arg Asp Leu Ala Xaa Lys Lys
    450                 455                 460

Lys Arg Ile Thr Asp Pro Ala Asp Leu Lys Ala Leu Val Ser Xaa Xaa
465                 470                 475                 480

Xaa Phe Xaa Ala Xaa Xaa Xaa Trp Xaa Leu Xaa Xaa Xaa Xaa Xaa Xaa
                485                 490                 495

Cys Xaa Lys Leu Xaa Leu Ser Thr Ala Thr Val Lys Leu Asn Asp Xaa
            500                 505                 510

Asp Gly Ser Pro Xaa Xaa Ser Cys Ser Val Gly Xaa Gly Xaa Val Asp
        515                 520                 525

Xaa Xaa Tyr Lys Ala Xaa Xaa Leu Ile Val Lys Xaa Pro Xaa Xaa Leu
```

-continued

```
              530                 535                 540
Leu Xaa Tyr Ser Xaa Asn Xaa Val Thr Xaa Gly Ile Xaa Xaa Xaa Xaa
545                     550                 555                 560

Xaa Xaa Arg Val Xaa Ile Xaa Xaa Glu Asn Xaa His Thr Ser Thr Xaa
                565                 570                 575

Ala Xaa Thr Xaa Xaa Xaa Xaa Xaa Thr Phe Ser Gly Xaa Xaa Ala
            580                 585                 590

Xaa Met Asp Xaa Val Xaa Ser Xaa Val Xaa Ala Tyr Xaa Xaa Ala Leu
        595                 600                 605

Asn Lys Xaa Xaa Xaa Xaa Xaa Xaa Xaa Xaa Xaa Xaa Asn Lys Pro
        610                 615                 620

Glu Ser Ser Ala Val Ile
625                 630
```

METHODS AND MEANS FOR MODIFICATION OF GLUCOSINOLATES IN PLANTS

This application is a 371 of PCT/GB98/03525, filed Nov. 23, 1998, which claims priority from GB 9724691.2, filed Nov. 21, 1997.

The present invention relates generally to modification of glucosinolates in plants and has arisen on the basis of cloning of GSL-ELONGASE gene alleles of *Arabidopsis thaliana*, and identification of homologues in other species, especially Brassicas.

Experimental evidence provided herein demonstrates regulation of the length of aliphatic glucosinolate (GSL) side chains by a Mendelian gene which is coincident with the major QTL which regulates the level of aliphatic glucosinolates. Two genes are identified in *Arabidopsis* which have similar function in catalysing the condensation of methionine and the elongated form of methionine with acetyl CoA, this reaction being important for the elongation of aliphatic glucosinolates. Homologues are identified in Brassicas.

The present invention provides for reduction or increase in GSL levels in plants, and the ability to engineer novel glucosinolates (e.g. in *Brassica*) with long side chains.

This allows for production of better seed quality (e.g. in *Brassica napus*), increase of anticarcinogenic GSL's in horticultural Brassicas, and enhancement of herbivore and pathogen resistance in both horticultural and oilseed Brassicas.

Glucosinolates are important secondary metabolites which determine seed quality of oilseed crucifers anticarcinogenic activity and flavour of horticultural crucifers and herbivore and pathogen interaction with crucifers. The major class of glucosinolates in many crucifers are aliphatic glucosinolates derived from methionine.

The biosynthesis of aliphatic glucosinolates can be considered in three parts. Firstly, the initial entry of methionine into glucosinolate biosynthesis and the development of chain elongation homologues of methionine, secondly the synthesis of the glycone moiety, and thirdly side chain modifications (FIG. 1, FIG. 2 and FIG. 18).

The GSL-ELONGASE gene provided by the present invention may be used to modify biosynthesis of glusosinolates, preferably the first of these three parts of biosynthesis, namely the initial entry of methionine and subsequent chain elongation.

The first part of biosynthesis involves the development of a series of chain elongated homologues of methionine via the sequential addition of a methyl group. These side chain elongated amino acids form the precursors to aliphatic glucosinolates of varying side chain lengths.

The elongation process involves the conversion of the amino acid to an α-keto acid via a transaminase, condensation of the α-keto acid with acetyl coA, isomerization involving a shift of the hydroxy group and conversion of the elongated α-keto acid back to an amino acid. Sequential rounds of elongation may involve condensation of acetyl CoA to the elongated α-keto acid without conversion back to an amino acid during each round of elongation.

Evidence of this pathway was provided by Chisholm and Wetter (Can J Biochem (1964) 42 1033–1040) who fed a number of labelled compounds including labelled methionine and acetate to *Armoracia lapathifolia*. They showed that the thiohydoximate carbon of the 2-propenyl glucosinolate was derived from the methyl carbon of acetate, and the carbon in the 2-propenyl side chain was derived from methionine. This indicates that acetate (acetyl-CoA) is the donor of the methyl group for chain elongation. On the basis of these results, Chisholm and Wetter (1964) proposed that 2-propenyl glucosinolate arises from homomethionine formed from methionine and acetate via a chain lengthening pathway similar to the formation of leucine from valine and acetate (Strassman M and Ceci L (1963) J Biol Chem 238 2445–2452).

Further evidence for this pathway was provided by Chisholm and Wetter (Can J Biochem (1966) 44 1625–1632) and Matsuo M and Yamazaki M (Biochem Biophys Res Comm (1966) 24 786–791. Both groups reported that [2-$^{14}$C]homomethionine was incorporated with greater efficiency than [2-$^{14}$C]methionine into 2-propenyl glucosinolate, and that the activity from the higher homologue was specifically incorporated into the thiohydroxymate carbon. Chisholm and Wetter (Plant Physiol (1967) 42 1762–1730) also provided evidence that the longer side chain glucosinolates, 3-butenyl and 4-pentenyl glucosinolates were derived from 2-amino-6-methylthiohexanoic acid ('dihomomethionine') and 2-amino-7-methylthioheptanoic acid ('tri-homomethionine'). It was suggested that each of these amino acids arise from methionine by multiple chain extensions via condensation of their respective α-keto acids with the methyl carbon of acetate. Further support for this pathway comes from the studies of Lee and Sherif (Biochem Biophys Acta (1968) 165 569–571; Biochemistry (1970) 9 2068–2071) and Josefsson (Physiol Plant (1971) 24 161–175) who showed that 2-amino-6-methylthiohexanoic acid was the precursor of 3-butenyl glucosinolate.

Another class of chain elongated glucosinolates are those with aromatic side chains derived from phenylalanine, the most common of which is phenylethyl glucosinolate. Underhill et al (Can J Biochem Physiol (1964) 40 1505–1514; Can J Biochem (1965) 43 179–187) provided evidence from labelling studies that the chain elongation process follows a similar route to that of aliphatic glucosinolates.

Another class of glucosinolates which arise from a chain elongating process are branched chained glucosinolates, including isopropyl GSI, isobutyl GSL, sec butyl GSL, 2-methylbutyl GSL, 3-methylbutyl GSI, 2, ethylbutyl GSL and 2-methyloctyl GSL. These may be derived from the amino acids valine, leucine and isoleucine.

In different embodiments, the present invention provides for manipulation of total levels of glucosinolates in plants such as oilseeds and horticultural crucifers through modification of glucosinolate biosynthesis, e.g. by up or down regulating the initial entry of methionine into glucosinolate biosynthesis. The present invention also provides for modification of the extent of chain elongation through the use of gene alleles, mutants and variants. This enables modifications to be made to meal quality of oilseeds crucifers, anticarcinogenic activity and flavour of horticultural crucifers, and/or resistance to herbivores and pathogens.

The most important crops for modification of meal quality are oilseed forms of *B.napus, B.rapa* (syn *B.campestris*), *B.juncea, B.carinata, Eruca sativa.* For enhancement of flavour and anticarcinogenic properties the most important species are *B.oleracea*, horticultural forms of *B.napus* (e.g. swedes) and *B.rapa* (including both turnips and chinese cabbage), and horticultural forms of *Raphanus, Eruca, Rorripa* and other similar salad crops. Glucosinolates may also be modified in condiment mustard forms of *B.juncea*. All of these species are targets for enhancement of pest and disease resistance via glucosinolate modification. Modifications for enhanced disease and pest resistance includes modifications to leaf and root glucosinolates to enhance the biofumigation potential of crucifers when used as geen manures and as break crops in cereal rotations.

The present invention provides a nucleic acid isolate encoding a polypeptide including the amino acid sequence shown in FIG. 10 (SEQ ID NO:1) for *Arabidopsis* GSL-ELONGASE, which may include the coding sequence shown in FIG. 7 or FIG. 8 (SEQ ID NO:2) which are of the GSL-ELONGASE gene of *Arabidopsis thaliana*, genomic and cDNA sequences respectively.

Allelic forms of the GSL-ELONGASE gene have been identified. Two allelic forms have been termed GSL-ELONGASE NORTH and GSL-ELONGASE SOUTH. A polypeptide including the amino acid sequence shown in FIG. 10 (SEQ ID NO:1) is provided by one aspect of the invention, along with encoding nucleic acid as disclosed. Further aspects provide a polypeptide including the amino acid sequence shown in FIG. 11 (SEQ ID NO:3), including the amino acid sequence of FIG. 10 (SEQ ID NO:1) and additional N-terminal amino acids, and a polypeptide including the amino acid sequence shown in FIG. 14 (SEQ ID NO:4), also encoding nucleic acid such as including the respective coding sequences shown in FIGS. 8 (SEQ ID NO:2), 9 (SEQ ID NO:5), 12 (SEQ ID NO:6), 13 (SEQ ID NO:7), 15 (SEQ ID NO:8) and 16 (SEQ ID NO:9).

Nucleic acid according to the present invention may have the sequence of the GSL-ELONGASE gene of *Arabidopsis thaliana* as indicated in a figure herein, or be a mutant, variant, derivative or allele or a homologue of the sequence provided. Preferred mutants, variants, derivatives and alleles are those which encode a protein which retains a functional characteristic of the protein encoded by the wild-type gene, especially the ability to catalyse a condensation reaction of (n α-)keto acid with acetyl CoA, and/or modify glucosinolate biosynthesis in a plant, such as *Arabidopsis thaliana*.

A mutant, variant, derivative, allele or homologue in accordance with the present invention may have the ability to affect a physical characteristic of a plant, particularly glucosinolate biosynthesis and/or character as discussed.

Polynucleotides which are not 100% identical to the sequences shown herein but fall within the scope of the invention can be obtained in a number of ways.

Other *Arabidopsis* variants (for example allelic forms) of the gene described herein may be obtained for example by probing cDNA or genomic DNA libraries made from *Arabidopsis* plants or cells.

In addition, other plant, monocot or dicot, homologues of the gene may be obtained. Such sequences may be obtained by making or obtaining cDNA libraries made from dividing cells or tissues or genomic DNA libraries from other plant species, and probing such libraries with probes comprising all or part of a nucleic acid of the invention under conditions of medium to high stringency (for example for hybridization on a solid support (filter) overnight incubation at 42° C. in a solution containing 50% formamide, 5×SSC (750 mM NaCl, 75 mM sodium citrate), 50 mM sodium phosphate (pH7.6), 5× Denhardt's solution, 10% dextran sulphate and 20 µg/ml salmon sperm DNA, followed by washing in 0.03 M sodium chloride and 0.03 M sodium citrate (i.e. 0.2×SSC) at from about 50° C. to about 60° C.).

Thus the present invention provides an isolated nucleic acid which hybridizes to the nucleotide sequence shown in a figure herein under the above mentioned hybridization and washing conditions. Such a nucleic acid is suitable for use as a probe for detecting the GSL ELONG gene, for example in Southern blots or in metaphase spreads.

Suitable probe and primer sequences are disclosed herein.

Alternatively, polynucleotides of the invention may be obtained by site directed mutagenesis of the sequences of shown in the figures or allelic variants thereof. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides. Further changes may be desirable to represent particular coding changes which are required to provide, for example, conservative substitutions.

In the context of cloning, it may be necessary for one or more gene fragments to be ligated to generate a full-length coding sequence. Also, where a full-length encoding nucleic acid molecule has not been obtained, a smaller molecule representing part of the full molecule, may be used to obtain full-length clones. Inserts may be prepared from partial cDNA clones and used to screen cDNA libraries. The full-length clones isolated may be subcloned into expression vectors and activity assayed by transfection into suitable host cells, e.g. with a reporter plasmid.

The present invention also extends to nucleic acid comprising transcriptional control sequences for the GSL ELONG gene. Such control sequences will be found 5' to the open reading frame of the gene and are obtainable by probing a genomic DNA library with a nucleic acid of the invention, selecting a clone which hybridizes under conditions of medium to high stringency, and sequencing the clone 5' to the open reading frame of the gene. Where only a small amount of sequence is present in the 5' region, this sequence may be used to reprobe the library to genome walk further upstream. Analysis of the upstream region will reveal control regions for gene expression including control regions common to many genes (i.e TATA and CAAT boxes) and other control regions, usually located from 1 to 10,000, such as 1 to 1000 or 50 to 500 nucleotides upstream of the start of transcription.

To confirm that such regions are the control regions of the gene, they may be linked to a reported gene (such as β-galactosidase) and tested in any suitable in vitro or in vivo system. For example the construct of the control region (e.g. comprising 50 to 500 nucleotides upstream of the start of transcription) and the reporter gene may be used to produce a transgenic plant and the pattern of expression, both spatially and developmentally, may be compared with that of the GSL ELONGASE gene. Where substantially similar patterns of expression are found, this shows that the construct comprises substantially all of the control region of the wild type gene.

FIG. 16 shows the nucleotide sequence of the GSL ELONGASE SOUTH genomic region including promoter.

The control region may be mutated to identify specific subregions responsible for transcriptional control. This may be achieved by a number of techniques well known in the art as such, including DNase protection footprint assays, in which the control region is brought into contact with an extract from a cell in which the GSL ELONGASE gene is actively expressed, and the regions of the control region which bind factors in that extract is determined.

Isolated nucleic acid comprising such control regions obtainable by such a method form a further aspect of the present invention.

The present invention further extends to genomic DNA exon sequences found between the introns encoding a GSL ELONGASE gene in plant. Such exon sequences may be obtained in a manner analogous to that described above for the transcriptional control sequences, with the appropriate genome walking being conducted between the intron sequences. The locations of the exons may be determined by comparing genomic and cDNA sequences of the gene, observing where the sequences line up and diverge, and looking for consensus splice sequences which define intron/exon boundaries.

FIGS. 8 (SEQ ID NO:2), 13 (SEQ ID NO:7) and 16 (SEQ ID NO:9) show genomic sequences including exons of the invention.

As noted above, changes to a sequence, to produce a mutant, variant or derivative, may be by one or more of addition, insertion, deletion or substitution of one or more nucleotides in the nucleic acid, leading to the addition, insertion, deletion or substitution of one or more amino acids in the encoded polypeptide. Of course, changes to the nucleic acid which make no difference to the encoded amino acid sequence are included.

Preferred nucleic acid sequences according to the present invention are shown in the figures, for instance see FIG. 9 (SEQ ID NO:5) of which the predicted encoded amino acid sequence of a polypeptide according to the present invention is shown in FIG. 10 (SEQ ID NO:1).

A mutant, allele, variant or derivative amino acid sequence in accordance with the present invention may include within the sequence shown in FIG. 10 (SEQ ID NO:1), FIG. 11 (SEQ ID NO:3) or FIG. 14 (SEQ ID NO:4), a single amino acid change with respect to the sequence shown in the relevant figure, or 2, 3, 4, 5, 6, 7, 8, or 9 changes, about 10, 15, 20, 30, 40 or 50 changes, or greater than about 50, 60, 70, 80 or 90 changes. In addition to one or more changes within the amino acid sequence shown in the relevant figure, a mutant, allele, variant or derivative amino acid sequence may include additional amino acids at the C-terminus and/or N-terminus.

A sequence related to a sequence specifically disclosed herein shares homology with that sequence. Homology may be at the nucleotide sequence and/or amino acid sequence level.

Preferably, the nucleic acid and/or amino acid sequence shares homology with the coding sequence or the sequence encoded by a nucleotide sequence of a figure herein, for instance FIG. 9 (SEQ ID NO:5) or FIG. 8 (SEQ ID NO:2), preferably at least about 50%, or 60%, or 70%, or 80% homology, most preferably at least about 90%, 95%, 96%, 97%, 98% or 99% homology.

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) *J. Mol. Biol.* 215: 403–10, which is in standard use in the art, or, and this may be preferred, either of the standard programs BestFit and GAP, which are part of the Wisconsin Package, Version 8, September 1994, (Genetics Computer Group, 575 Science Drive, Madison, Wis., USA, Wisconsin 53711). BestFit makes an optimal alignment of the best segment of similarity between two sequences. Optimal alignments are found by inserting gaps to maximize the number of matches using the local homology algorithm of Smith and Waterman (Advances in Applied Mathematics (1981) 2, pp. 482–489). GAP uses the Needleman and Wunsch algorithm to align two complete sequences that maximizes the number of matches and minimizes the number of gaps. Generally, the default parameters are used, with a gap creation penalty=12 and gap extension penalty=4.

Homology is generally over the full-length of the relevant sequence shown herein, that is unless stated otherwise, or it may be over a contiguous sequence of about or greater than about 20, 25, 30, 33, 40, 50, 67, 133, 167, 200, 233, 267, 300, 333, 400, 450, 500, 550, 600 or more amino acids or codons, compared with the relevant amino acid sequence or nucleotide sequence as the case may be.

Nucleic acid according to the present invention may consist essentially of or consist of the relevant coding sequence. Nucleic acid according to the present invention may include a promoter or other regulatory sequence as discussed further elsewhere herein, and such regulatory sequence may be heterologous to the coding sequence, that is to say not naturally operably linked therewith. Nucleic acid according to the present invention may be cDNA or lacking one or more introns which occur naturally, or may be in any non-naturally occurring form. A coding sequence in accordance with the present invention may be included with a larger nucleic acid molecule of less than about 10,000 nucleotides, less than about 5,000 nucleotides or less than about 2,000 nucleotides.

Also provided by an aspect of the present invention is nucleic acid including or consisting essentially of a sequence of nucleotides complementary to a nucleotide sequence hybridisable with any encoding sequence provided herein. Another way of looking at this would be for nucleic acid according to this aspect to be hybridisable with a nucleotide sequence complementary to any encoding sequence provided herein. Of course, DNA is generally double-stranded and blotting techniques such as Southern hybridisation are often performed following separation of the strands without a distinction being drawn between which of the strands is hybridising. Preferably the hybridisable nucleic acid or its complement encode a product able to influence a physical characteristic of a plant, particularly glucosinolate content and/or nature, and/or catalyse a condensation reaction of (n α-)keto acid with acetyl CoA. Preferred conditions for hybridisation are familiar to those skilled in the art, but are generally stringent enough for there to be positive hybridisation between the sequences of interest to the exclusion of other sequences.

The nucleic acid, which may contain for example DNA encoding a polypeptide including the amino acid sequence of FIG. 10 (SEQ ID NO:1) or other polypeptide disclosed herein, as genomic or cDNA, may be in the form of a recombinant and preferably replicable vector, for example a plasmid, cosmid, phage or *Agrobacterium* binary vector. The nucleic acid may be under the control of an appropriate promoter or other regulatory elements for expression in a host cell such as a microbial, e.g. bacterial, or plant cell. In the case of genomic DNA, this may contain its own promoter or other regulatory elements and in the case of cDNA this may be under the control of an appropriate promoter or other regulatory elements for expression in the host cell.

A vector including nucleic acid according to the present invention need not include a promoter or other regulatory sequence, particularly if the vector is to be used to introduce the nucleic acid into cells for recombination into the genome.

Those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference. Specific procedures and vectors previously used with wide success upon plants are described by Bevan (Nucl. Acids Res. 12, 8711–8721 (1984)) and Guerineau and Mullineaux (1993) (Plant transformation and expression vectors. In: Plant Molecular Biology Labfax (Croy RRD ed) Oxford, BIOS Scientific Publishers, pp 121–148).

Selectable genetic markers may be used consisting of chimaeric genes that confer selectable phenotypes such as resistance to antibiotics such as kanamycin, hygromycin, phosphinotricin, chlorsulfuron, methotrexate, gentamycin, spectinomycin, imidazolinones and glyphosate.

Vector constructs according to the present invention may include the GSL-ELONG sense and antisense sequences included in the constructs illustrated schematically in FIG. 19. Representative or preferred embodiments of constructs according to the present invention are shown schematically in FIG. 19. The person skilled in the art will readily recognise that alternative promoters, terminators and other components may be substituted for any of those in any of the illustrated constructs.

Nucleic acid molecules and vectors according to the present invention may be provided isolated and/or purified from their natural environment, in substantially pure or homogeneous form, or free or substantially free of nucleic acid or genes of the species of interest or origin other than the sequence encoding a polypeptide with the required function. Nucleic acid according to the present invention may include cDNA, RNA, genomic DNA and may be wholly or partially synthetic. The term "isolate" encompasses all these possibilities. Where a DNA sequence is specified, e.g. with reference to a figure, unless context requires otherwise the RNA equivalent, with U substituted for T where it occurs, is encompassed.

When introducing a chosen gene construct into a cell, certain considerations must be taken into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material either will or will not occur. Finally, as far as plants are concerned the target cell type must be such that cells can be regenerated into whole plants.

Plants transformed with the DNA segment containing the sequence may be produced by standard techniques which are already known for the genetic manipulation of plants. DNA can be transformed into plant cells using any suitable technology, such as a disarmed Ti-plasmid vector carried by *Agrobacterium* exploiting its natural gene transfer ability (EP-A-270355, EP-A-0116718, NAR 12(22) 8711-87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, PNAS U.S.A. 87; 1228 (1990d) Physical methods for the transformation of plant cells are reviewed in Oard, 1991, Biotech. Adv. 9: 1–11.

*Agrobacterium* transformation is widely used by those skilled in the art to transform dicotyledonous species. There are various approaches used for the routine production of stable, fertile transgenic plants in almost all economically relevant monocot plants (Toriyama, et al. (1988) *Bio/Technology* 6, 1072–1074; Zhang, et al. (1988) *Plant Cell Rep.* 7, 379–384; Zhang, et al. (1988) *Theor Appl Genet* 76, 835–840; Shimamoto, et al. (1989) *Nature* 338, 274–276; Datta, et al. (1990) *Bio/Technology* 8, 736–740; Christou, et al. (1991) *Bio/Technology* 9, 957–962; Peng, et al. (1991) International Rice Research Institute, Manila, Philippines 563–574; Cao, et al. (1992) *Plant Cell Rep.* 11, 585–591; Li, et al. (1993) *Plant Cell Rep.* 12, 250–255; Rathore, et al. (1993) *Plant Molecular Biology* 21, 871–884; Fromm, et al. (1990) *Bio/Technology* 8, 833–839; Gordon-Kamm, et al. (1990) *Plant Cell* 2, 603–618; D'Halluin, et al. (1992) *Plant Cell* 4, 1495–1505; Walters, et al. (1992) *Plant Molecular Biology* 18, 189–200; Koziel, et al. (1993) *Biotechnology* 11, 194–200; Vasil, I. K. (1994) *Plant Molecular Biology* 25, 925–937; Weeks, et al. (1993) *Plant Physiology* 102, 1077–1084; Somers, et al. (1992) *Bio/Technology* 10, 1589–1594; WO92/14828). In particular, *Agrobacterium* mediated transformation is now emerging also as an highly efficient alternative transformation method in monocots (Hiei et al. (1994) *The Plant Journal* 6, 271–282).

The generation of fertile transgenic plants has been achieved in the cereals rice, maize, wheat, oat, and barley (reviewed in Shimamoto, K. (1994) *Current Opinion in Biotechnology* 5, 158–162.; Vasil, et al. (1992) *Bio/Technology* 10, 667–674; Vain et al., 1995, *Biotechnology Advances* 13 (4): 653–671; Vasil, 1996, *Nature Biotechnology* 14 page 702).

Microprojectile bombardment, electroporation and direct DNA uptake are preferred where *Agrobacterium* is inefficient or ineffective. Alternatively, a combination of different techniques may be employed to enhance the efficiency of the transformation process, eg bombardment with *Agrobacterium* coated microparticles (EP-A-486234) or microprojectile bombardment to induce wounding followed by co-cultivation with *Agrobacterium* (EP-A-486233).

Following transformation, a plant may be regenerated, e.g. from single cells, callus tissue or leaf discs, as is standard in the art. Almost any plant can be entirely regenerated from cells, tissues and organs of the plant.

Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

A GSL-ELONGASE gene and modified versions thereof (alleles, mutants, variants and derivatives thereof), and other nucleic acid provided herein, including species homologues, may be used to modify glucosinolate content and/or nature in a transgenic plant, and/or catalyse a condensation reaction of (n α-)keto acid with acetyl CoA. Nucleic acid such as a vector as described herein may be used for the production of a transgenic plant. Such a plant may possess an altered phenotype, particular in terms of glucosinolate content and/or nature compared with wild-type (that is to say a plant that is wild-type for GSL-ELONGASE or the relevant homologue thereof).

The invention further encompasses a host cell transformed with nucleic acid or a vector according to the present invention, especially a plant or a microbial cell. Thus, a host cell, such as a plant cell, including heterologous nucleic acid according to the present invention is provided. Within the cell, the nucleic acid may be incorporated within the chromosome. There may be more than one heterologous nucleotide sequence per haploid genome.

Also according to the invention there is provided a plant cell having incorporated into its genome nucleic acid, particularly heterologous nucleic acid, as provided by the present invention, under operative control of a regulatory sequence for control of expression. The coding sequence may be operably linked to one or more regulatory sequences which may be heterologous or foreign to the gene, such as not naturally associated with the gene for its expression. The nucleic acid according to the invention may be placed under the control of an externally inducible gene promoter to place expression under the control of the user.

A suitable inducible promoter is the GST-II-27 gene promoter which has been shown to be induced by certain chemical compounds which can be applied to growing plants. The promoter is functional in both monocotyledons and dicotyledons. It can therefore be used to control gene expression in a variety of genetically modified plants, including field crops such as canola, sunflower, tobacco, sugarbeet, cotton; cereals such as wheat, barley, rice, maize, sorghum; fruit such as tomatoes, mangoes, peaches, apples, pears, strawberries, bananas, and melons; and vegetables such as carrot, lettuce, cabbage and onion. The GST-II-27 promoter is also suitable for use in a variety of tissues, including roots, leaves, stems and reproductive tissues.

A further aspect of the present invention provides a method of making such a plant cell involving introduction of nucleic acid or a suitable vector including the sequence of nucleotides into a plant cell and causing or allowing recombination between the vector and the plant cell genome to introduce the sequence of nucleotides into the genome. The invention extends to plant cells containing nucleic acid according to the invention as a result of introduction of the nucleic acid into an ancestor cell.

The term "heterologous" may be used to indicate that the gene/sequence of nucleotides in question have been introduced into said cells of the plant or an ancestor thereof, using genetic engineering, ie by human intervention. A transgenic plant cell, i.e. transgenic for the nucleic acid in question, may be provided. The transgene may be on an extra-genomic vector or incorporated, preferably stably, into the genome. A heterologous gene may replace an endogenous equivalent gene, ie one which normally performs the same or a similar function, or the inserted sequence may be additional to the endogenous gene or other sequence. An advantage of introduction of a heterologous gene is the ability to place expression of a sequence under the control of a promoter of choice, in order to be able to influence expression according to preference. Furthermore, mutants, variants and derivatives of the wild-type gene, e.g. with higher or lower activity than wild-type, may be used in place of the endogenous gene. Nucleic acid heterologous, or exogenous or foreign, to a plant cell may be non-naturally occuring in cells of that type, variety or species. Thus, nucleic acid may include a coding sequence of or derived from a particular type of plant cell or species or variety of plant, placed within the context of a plant cell of a different type or species or variety of plant. A further possibility is for a nucleic acid sequence to be placed within a cell in which it or a homologue is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression. A sequence within a plant or other host cell may be identifiably heterologous, exogenous or foreign.

Plants which include a plant cell according to the invention are also provided, along with any part or propagule thereof, seed, selfed or hybrid progeny and descendants. A plant according to the present invention may be one which does not breed true in one or more properties. Plant varieties may be excluded, particularly registrable plant varieties according to Plant Breeders' Rights. It is noted that a plant need not be considered a "plant variety" simply because it contains stably within its genome a transgene, introduced into a cell of the plant or an ancestor thereof.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, offspring, clone or descendant.

The invention further provides a method of influencing or affecting a physical characteristic of a plant, particularly glucosinolate content and/or nature, including causing or allowing expression of a heterologous nucleic acid sequence as discussed within cells of the plant.

The invention further provides a method of including expression from nucleic acid encoding a polypeptide including the amino acid sequence of FIG. 10 (SEQ ID NO:1), or a mutant, variant, allele or derivative of the sequence, or a homologue, according to the disclosure herein, within cells of a plant (thereby producing the encoded polypeptide), following an earlier step of introduction of the nucleic acid into a cell of the plant or an ancestor thereof. Such a method may influence or affect a characteristic of the plant, such as glucosinolate content and/or nature. This may be used in combination with any other gene, such as transgenes involved in glucosinolate biosynthesis or other phenotypic trait or desirable property.

The present invention also encompasses the expression product of any of the nucleic acid sequences disclosed and methods of making the expression product by expression from encoding nucleic acid therefore under suitable conditions, which may be in suitable host cells. Following expression, the product may be isolated from the expression system and may be used as desired, for instance in formulation of a composition including at least one additional component.

The present invention also provides for the production and use of fragments of the full-length polypeptides disclosed herein, especially active portions thereof. An "active portion" of a polypeptide means a peptide which is less than said full length polypeptide, but which retains its essential biological activity. In particular, the active portion retains the ability to catalyse a condensation reaction of (n α-)keto acid with acetyl CoA, and/or modify glucosinolate biosynthesis in a plant, such as *Arabidopsis thaliana*.

A "fragment" of a polypeptide means a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids. Fragments of the polypeptides may include one or more epitopes useful for raising antibodies to a portion of any of the amino acid sequences disclosed herein. Preferred epitopes are those to which antibodies are able to bind specifically, which may be taken to be binding a polypeptide or fragment thereof of the invention with an affinity which is at least about 1000× that of other polypeptides.

Purified protein according to the present invention, or a fragment, mutant, derivative or variant thereof, e.g. produced recombinantly by expression from encoding nucleic acid therefor, may be used to raise antibodies employing techniques which are standard in the art. Antibodies and polypeptides comprising antigen-binding fragments of antibodies may be used in identifying homologues from other species as discussed further below.

Methods of producing antibodies include immunising a mammal (e.g. human, mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, Nature 357: 80–82). Antibodies may be polyclonal or monoclonal.

As an alternative or supplement to immunising a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibodies raised to a polypeptide or peptide can be used in the identification and/or isolation of homologous polypeptides, and then the encoding genes. Thus, the present invention provides a method of identifying or isolating a polypeptide with the desired function (in accordance with embodiments disclosed herein), comprising screening candidate polypeptides with a polypeptide comprising the antigen-binding domain of an antibody (for example whole antibody or a suitable fragment thereof, e.g. scFv, Fab) which is able to bind a polypeptide or fragment, variant or derivative thereof according to the present invention or preferably has binding specificity for such a polypeptide. Specific binding members such as antibodies and polypeptides comprising antigen binding domains of antibodies that bind and are preferably specific for a polypeptide or mutant, variant or derivative thereof according to the invention represent further aspects of the present invention, particularly in isolated and/or purified form, as do their use and methods which employ them.

Candidate polypeptides for screening may for instance be the products of an expression library created using nucleic acid derived from an plant of interest, or may be the product of a purification process from a natural source. A polypeptide found to bind the antibody may be isolated and then may be subject to amino acid sequencing. Any suitable technique may be used to sequence the polypeptide either wholly or partially (for instance a fragment of the polypeptide may be sequenced). Amino acid sequence information may be used in obtaining nucleic acid encoding the polypeptide, for instance by designing one or more oligonucleotides (e.g. a degenerate pool of oligonucleotides) for use as probes or primers in hybridization to candidate nucleic acid, or by searching computer sequence databases, as discussed further below.

A further aspect of the present invention provides a method of identifying and cloning GSL-ELONGASE homologues from plant species other than *Arabidopsis thaliana* which method employs a nucleotide sequence derived from that shown in FIG. 8 (SEQ ID NO:2), FIG. 9 (SEQ ID NO:5), FIG. 12 (SEQ ID NO:6), FIG. 13 (SEQ ID NO:7), FIG. 15 (SEQ ID NO:8) or FIG. 16 (SEQ ID NO:9). As discussed above, sequences derived from these may themselves be used in identifying and in cloning other sequences. The nucleotide sequence information provided herein, or any part thereof, may be used in a data-base search to find homologous sequences, expression products of which can be tested for ability to influence a plant characteristic. These may have ability to catalyse a condensation reaction of (n α-)keto acid with acetyl CoA, and/or modify glucosinolate biosynthesis in a plant, altering glucosinolate content and/or nature. Alternatively, nucleic acid libraries may be screened using techniques well known to those skilled in the art and homologous sequences thereby identified then tested.

The present invention also extends to nucleic acid encoding an GSL-ELONGASE homologue obtained using a nucleotide sequence derived from that shown in FIG. 8 (SEQ ID NO:2), FIG. 9 (SEQ ID NO:5), FIG. 12 (SEQ ID NO:6), FIG. 13 (SEQ ID NO:7), FIG. 15 (SEQ ID NO:8) or FIG. 16 (SEQ ID NO:9). In certain embodiments, nucleic acid according to the present invention encodes a polypeptide which has homology with all or part of the GSL-ELONGASE amino acid sequence shown in FIG. 10 (SEQ ID NO:1), in the terms discussed already above (e.g. for length), which homology is greater over the length of the relevant part (i.e. fragment) than the homology shared between a respective part of the GSL-ELONGASE amino acid sequence of FIG. 10 (SEQ ID NO:1), also shown in FIG. 5, and the other sequences shown in FIG. 5, and may be greater than about 5% greater, more preferably greater than about 10% greater, more preferably greater than about 20% greater, and more preferably greater than about 30% greater. Thus, to exemplify with reference to one embodiment, nucleic acid encoding an amino acid mutant, variant or derivative of the amino acid sequence shown in FIG. 10 (SEQ ID NO:1) may be provided wherein the encoded amino acid sequence includes a contiguous sequence of about 100 amino acids which has greater homology with a contiguous sequence of 100 amino acids within the GSL-ELONGASE amino acid sequence of FIG. 10 (SEQ ID NO:1) (also shown in FIG. 5) than any contiguous sequence of 100 amino acids within another sequence shown in FIG. 5, preferably greater than about 5% greater homology, and so on.

Similarly, nucleic acid according to certain embodiments of the present invention may have homology with all or part of the nucleotide sequence shown in FIG. 8 (SEQ ID NO:2) or FIG. 9 (SEQ ID NO:5), in the terms discussed already above (e.g. for length), which homology is greater over the length of the relevant part (i.e. fragment) than the homology shared with a respective part of the coding nucleotide sequence for the other amino acid sequences shown in FIG. 5 and referenced herein, and may be greater than about 5% greater, more preferably greater than about 10% greater, more preferably greater than about 20% greater, and more preferably greater than about 30% greater. Thus, to exemplify with reference to one embodiment, nucleic acid may be provided in accordance with the present invention wherein the nucleotide sequence includes a contiguous sequence of about 300 nucleotides (or 100 codons) which has greater homology with a contiguous sequence of 300 nucleotides within the nucleotide sequence of FIG. 8 (SEQ ID NO:2) or FIG. 9 (SEQ ID NO:5) than any contiguous sequence of 100 nucleotides within the relevant sequence, preferably greater than about 5% greater homology, and so on.

The provision of sequence information for the GSL-ELONGASE gene of *Arabidopsis thaliana* enables the obtention of homologous sequences from other plant species. In particular, homologues may be easily isolated from related, commercially important Crucifer species (e.g. *Brassica nigra, Brassica napus, Brassica oleraceae, Brassica rapa, Brassica carinata, Brassica juncea*).

Thus, included within the scope of the present invention are nucleic acid molecules which encode amino acid sequences which are homologues of GSL-ELONGASE of *Arabidopsis thaliana*. Homology may be at the nucleotide sequence and/or amino acid sequence level, as has already been discussed above. A homologue from a species other than *Arabidopsis thaliana* encodes a product which causes a phenotype similar to that caused by the *Arabidopsis thaliana* GSL-ELONGASE gene, generally including ability to catalyse a condensation reaction of (n α-)keto acid with acetyl CoA, and/or affect glucosinolate biosynthesis to alter glucosinolate content and/or nature in a plant, such as in *Arabidopsis thaliana*. In addition, mutants, derivatives or alleles of these genes may have altered, e.g. increased or decreased, enzymatic activity or substrate specificity compared with wild-type.

GSL-ELONGASE gene homologues may also be identified from economically important monocotyledonous crop plants such as rice and maize. Although genes encoding the same protein in monocotyledonous and dicotyledonous plants show relatively little homology at the nucleotide level, amino acid sequences are conserved. Therefore it is possible to use public sequence databases to identify *Arabidopsis*, rice or maize cDNA clone sequences that were obtained in random sequencing programmes and share homology to the gene of interest, as has been done for other genes isolated from *Arabidopsis* (e.g CO; WO 96/14414). Of course, mutants, derivatives and alleles of these sequences are included within the scope of the present invention in the same terms as discussed above for the *Arabidopsis thaliana* GSL-ELONGASE gene.

According to a further aspect, the present invention provides a method of identifying or a method of cloning a GSL-ELONGASE homologue, e.g. from a species other than *Arabidopsis thaliana* the method employing a nucleotide sequence derived from that shown in FIG. 8 (SEQ ID NO:2) or FIG. 9 (SEQ ID NO:5), FIG. 12 (SEQ ID NO:6), FIG. 13 (SEQ ID NO:7), FIG. 15 (SEQ ID NO:8) or FIG. 16 (SEQ ID NO:9). For instance, such a method may employ an oligonucleotide or oligonucleotides which comprises or consists of a sequence or sequences conserved between or encoding a sequence or sequences conserved between the sequences shown in or encoding the sequences shown in FIG. 5 or FIG. 6 to search for homologues. Thus, a method of obtaining nucleic acid is provided, comprising hybridisation of an oligonucleotide or a nucleic acid molecule comprising such an oligonucleotide to target/candidate nucleic acid. Target or candidate nucleic acid may, for example, comprise a genomic or cDNA library obtainable from an organism known to contain or suspected of containing such nucleic acid, either monocotyledonous or dicotyledonous. Successful hybridisation may be identified and target/candidate nucleic acid isolated for further investigation and/or use.

Hybridisation may involve probing nucleic acid and identifying positive hybridisation under suitably stringent conditions (in accordance with known techniques) and/or use of oligonucleotides as primers in a method of nucleic acid amplification, such as PCR. For probing, preferred conditions are those which are stringent enough for there to be a simple pattern with a small number of hybridisations identified as positive which can be investigated further. It is well known in the art to increase stringency of hybridisation gradually until only a few positive clones remain.

For instance, screening may initially be carried out under conditions, which comprise a temperature of about 37° C. or more, a formamide concentration of less than about 50%, and a moderate to low salt (e.g. Standard Saline Citrate ('SSC')=0.15 M sodium chloride; 0.15 M sodium citrate; pH 7) concentration.

Alternatively, a temperature of about 50° C. or more and a high salt (e.g. 'SSPE'=0.180 mM sodium chloride; 9 mM disodium hydrogen phosphate; 9 mM sodium dihydrogen phosphate; 1 mM sodium EDTA; pH 7.4). Preferably the screening is carried out at about 37° C., a formamide concentration of about 20%, and a salt concentration of about 5×SSC, or a temperature of about 50° C. and a salt concentration of about 2×SSPE. These conditions will allow the identification of sequences which have a substantial degree of homology (similarity, identity) with the probe sequence, without requiring the perfect homology for the identification of a stable hybrid.

Suitable conditions include, e.g. for detection of sequences that are about 80–90% identical, hybridization overnight at 42° C. in 0.25 M Na$_2$HPO$_4$, pH 7.2, 6.5% SDS, 10% dextran sulfate and a final wash at 55° C. in 0.1X SSC, 0.1% SDS. For detection of sequences that are greater than about 90% identical, suitable conditions include hybridization overnight at 65° C. in 0.25 M Na$_2$HPO$_4$, pH 7.2, 6.5% SDS, 10% dextran sulfate and a final wash at 60° C. in 0.1×SSC, 0.1% SDS.

The present invention extends to nucleic acid selectively hybridisable under high stringency with nucleic acid identified herein.

As an alternative to probing, though still employing nucleic acid hybridisation, oligonucleotides designed to amplify DNA sequences may be used in PCR reactions or other methods involving amplification of nucleic acid, using routine procedures. See for instance "PCR protocols; A Guide to Methods and Applications", Eds. Innis et al, 1990, Academic Press, New York.

Preferred amino acid sequences suitable for use in the design of probes or PCR primers for some purposes are sequences conserved (completely, substantially or partly) between the GSL-ELONGASE sequence and at least one other of the sequences shown in FIG. 5 or FIG. 6.

Preferred primers for amplification of conserved regions of GSL-ELONGASE for use as probes to obtain genomic or cDNA clones may include the following:
Primer Pair 1
ATGGTTCTCCGGTCAGGGTTA (SEQ ID NO:16)
CACGGTCTTGGCGATGGTTTT (SEQ ID NO:17)
These primers will amplify nucleotides 1001 to 1381. This region will include exon 1 and conserved region 1.
Primer Pair 2
AAAACCATCGCCAAGACCGTG (SEQ ID NO:18)
TCTTCGCACCCAAATTGGATG (SEQ ID NO:19)

These primers will amplify nucleotides between 1361 and 1940. This region will include intron 1 and exon 2, containing conserved region 2.

Primer Pair 3
ATGGTTCTCCGGTCAGGGTTA (SEQ ID NO:16)
TCTTCGCACCCAAATTGGATG (SEQ ID NO:19)

These primers will amplify nucleotides between 1001 and 1940. This region will contain conserved regions 1 and 2.

On the basis of amino acid sequence information oligonucleotide probes or primers may be designed, taking into account the degeneracy of the genetic code, and, where appropriate, codon usage of the organism from the candidate nucleic acid is derived.

Preferably an oligonucleotide in accordance with certain embodiments of the invention, e.g. for use in nucleic acid amplification, is up to about 50 nucleotides, or about 40 nucleotides or about 30 or fewer nucleotides in length (e.g. 18, 21 or 24).

Assessment of whether or not such a PCR product corresponds to a homologue gene may be conducted in various ways. A PCR band from such a reaction might contain a complex mix of products. Individual products may be cloned and each one individually screened. It may be analysed by transformation to assess function on introduction into a plant of interest.

As noted, nucleic acid according to the present invention is obtainable using oligonucleotides, designed on the basis of sequence information provided herein, as probes or primers. Nucleic acid isolated and/or purified from one or more cells of a plant (see above), or a nucleic acid library derived from nucleic acid isolated and/or purified from the plant (e.g. a cDNA library derived from mRNA isolated from the plant), may be probed under conditions for selective hybridisation and/or subjected to a specific nucleic acid amplification reaction such as the polymerase chain reaction (PCR). The nucleic acid probed or used as template in the amplification reaction may be genomic DNA, cDNA or RNA. If necessary, one or more gene fragments may be ligated to generate a full-length coding sequence.

PCR primers derived from the GSL-ELONGASE sequences disclosed herein may readily be tested for their specificity for amplifying nucleic acid according to the present invention, using both genomic DNA and RT-PCR templates.

Cloning and subsequent sequencing of PCR products may be used to indicate amplification of the expected derived gene fragment. Full length cDNA clones can be obtained as described by 5' and 3' RACE technology if RT-PCR products are used as templates.

Various aspects of the present invention include the obtainable nucleic acid, methods of screening material, e.g. cell lysate, nucleic acid preparations, for the presence of nucleic acid of interest, methods of obtaining the nucleic acid, and suitable primers and primer combinations.

The sequence information provided herein also allows the design of diagnostic tests for determination of the presence of a specific gene or allele thereof in any given plant, cultivar, variety, population, landrace, part of a family or other selection in a breeding programme or other such genotype. A diagnostic test may be based on determination of the presence or absence of a particular allele by means of nucleic acid or polypeptide determination.

At the nucleic acid level, this may involve hybridisation of a suitable oligo- or poly-nucleotide, such as a fragment of the gene or a homologue thereof, including any homologue disclosed herein, or any particular allele, such as an allele which gives a desirable phenotype, such as any such allele disclosed herein. The hybridisation may involve PCR designed to amplify a product from a given allelic version of the gene, with subsequent detection of an amplified product by any of a number of possible methods including but not limited to gel electrophoresis, capillary electrophoresis, direct hybridisation of nucleotide sequence probes and so on. A diagnostic test may be based on PCR designed to amplify various alleles or any allele from the relevant locus, with a test to distinguish the different possible alleles by any of a number of possible methods, including DNA fragment size, restriction site variation (e.g. CAPS—cleaved amplified polymorphic sites) and so on. A diagnostic test may also be based on a great number of possible variants of nucleic acid analysis that will be apparent to those skilled in the art, such as use of a synthetic sequence as a hybridisation probe.

Broadly, the methods divide into those screening for the presence of nucleic acid sequences and those that rely on detecting the presence or absence of a polypeptide. The methods may make use of biological samples from one or more plants or cells that are suspected to contain the nucleic acid sequences or polypeptide.

Exemplary approaches for detecting nucleic acid or polypeptides include analysing a sample from the plant or plant cell by:

(a) comparing the sequence of nucleic acid in the sample with all or part of the nucleotide sequence shown in FIG. 8 (SEQ ID NO:2) or FIG. 9 (SEQ ID NO:5), FIG. 12 (SEQ ID NO:6), FIG. 13 (SEQ ID NO:7), FIG. 15 (SEQ ID NO:8) or member including nucleic acid hybridisable with the sequence of FIG. 8 or FIG. 9, or FIG. 12, FIG. 13, FIG. 15 or FIG. 16, or a polypeptide including a binding domain with specificity for nucleic acid including the sequence of FIG. 8 or FIG. 9, or FIG. 12, FIG. 13, FIG. 15 or FIG. 16, or the polypeptide encoded by it, or a mutated form thereof, and determining binding of the specific binding member;

(e) performing PCR involving one or more primers based on the nucleotide sequence shown in FIG. 8 or FIG. 9, or FIG. 12, FIG. 13, FIG. 15 or FIG. 16, to screen the sample for nucleic acid including the nucleotide sequence of FIG. 8 or FIG. 9, or FIG. 12, FIG. 13, FIG. 15 or FIG. 16, or a mutant, allele or variant thereof.

When screening for a GSL-ELONGASE allele nucleic acid, the nucleic acid in the sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

ID NO:2) or FIG. 9 (SEQ ID NO:5), or FIG. 12 (SEQ ID NO:6), FIG. 13 (SEQ ID NO:7), FIG. 15 (SEQ ID NO:8) or FIG. 16 (SEQ ID NO:9), or a polypeptide including a binding domain with specificity for nucleic acid including the sequence of FIG. 8 (SEQ ID NO:2) or FIG. 9 (SEQ ID NO:5), or FIG. 12 (SEQ ID NO:6), FIG. 13 (SEQ ID NO:7), FIG. 15 (SEQ ID NO:8) or FIG. 16 (SEQ ID NO:9), or the polypeptide encoded by it, or a mutated form thereof, and determining binding of the specific binding member;

(e) performing PCR involving one or more primers based on the nucleotide sequence shown in FIG. 8 (SEQ ID NO:2) or FIG. 9 (SEQ ID NO:5), or FIG. 12 (SEQ ID. NO:6), FIG. 13 (SEQ ID NO:7), FIG. 15 (SEQ ID NO:8) or FIG. 16 (SEQ ID NO:9), to screen the sample for nucleic acid including the nucleotide sequence of FIG. 8 (SEQ ID NO:2) or FIG. 9 (SEQ ID NO:5), or FIG. 12 (SEQ ID NO:6), FIG. 13 (SEQ ID NO:7), FIG. 15 (SEQ ID NO:8) or FIG. 16 (SEQ ID NO:9), or a mutant, allele or variant thereof.

When screening for a GSL-ELONGASE allele nucleic acid, the nucleic acid in the sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

A variant form of the gene may contain one or more insertions, deletions, substitutions and/or additions of one or more nucleotides compared with the wild-type sequence which may or may not disrupt or alter the gene function. Differences at the nucleic acid level are not necessarily reflected by a difference in the amino acid sequence of the encoded polypeptide. However, a mutation or other difference in a gene may result in a frame-shift or stop codon, which could seriously affect the nature of the polypeptide produced (if any), or a point mutation or gross mutational change to the encoded polypeptide, including insertion, deletion, substitution and/or addition of one or more amino acids or regions in the polypeptide. A mutation in a promoter sequence or other regulatory region may prevent or reduce expression from the gene or affect the processing or stability of the mRNA transcript.

Tests may be carried out on preparations containing genomic DNA, cDNA and/or mRNA. Testing cDNA or mRNA has the advantage of the complexity of the nucleic acid being reduced by the absence of intron sequences, but the possible disadvantage of extra time and effort being required in making the preparations. RNA is more difficult to manipulate than DNA because of the wide-spread occurrence of RN'ases.

Nucleic acid in a test sample may be sequenced and the sequence compared with the sequence shown in FIG. 8 (SEQ ID NO:2) or FIG. 9 (SEQ ID NO:5), or other figure herein, to determine whether or not a difference is present. If so, the difference can be compared with known alleles to determine whether the test nucleic acid contains one or more of the variations indicated, or the difference can be investigated for association with a desired phenotype.

The amplified nucleic acid may then be sequenced as above, and/or tested in any other way to determine the presence or absence of a particular feature. Nucleic acid for testing may be prepared from nucleic acid removed from cells or in a library using a variety of other techniques such as restriction enzyme digest and electrophoresis.

Nucleic acid may be screened using a variant- or allele-specific probe. Such a probe corresponds in sequence to a region of the gene, or its complement, containing a sequence alteration known to be associated with alteration of catalytic activity and/or ability to affect glucosinolate biosynthesis. Under suitably stringent conditions, specific hybridisation of such a probe to test nucleic acid is indicative of the presence of the sequence alteration in the test nucleic acid. For efficient screening purposes, more than one probe may be used on the same test sample. Allele- or variant-specific oligonucleotides may similarly be used in FCR to specifically amplify particular sequences if present in a test sample. Assessment of whether a PCR band contains a gene variant may be carried out in a number of ways familiar to those skilled in the art. The PCR product may for instance be treated in a way that enables one to display the mutation or polymorphism on a denaturing polyacrylamide DNA sequencing gel, with specific bands that are linked to the gene variants being selected.

An alternative or supplement to looking for the presence of variant sequences in a test sample is to look for the presence of the normal sequence, e.g. using a suitably specific oligonucleotide probe or primer.

Approaches which rely on hybridisation between a probe and test nucleic acid and subsequent detection of a mismatch may be employed. Under appropriate conditions (temperature, pH etc.), an oligonucleotide probe will hybridise with a sequence which is not entirely complementary. The degree of base-pairing between the two molecules will be sufficient for them to anneal despite a mis-match. Various approaches are well known in the art for detecting the presence of a mis-match between two annealing nucleic acid molecules.

For instance, RN'ase A cleaves at the site of a mis-match. Cleavage can be detected by electrophoresing test nucleic acid to which the relevant probe or probe has annealed and looking for smaller molecules (i.e. molecules with higher electrophoretic mobility) than the full length probe/test hybrid. Other approaches rely on the use of enzymes such as resolvases or endonucleases.

Thus, an oligonucleotide probe that has the sequence of a region of the normal gene (either sense or anti-sense strand) in which mutations associated with particular phenotypes are known to occur may be annealed to test nucleic acid and the presence or absence of a mis-match determined. Detection of the presence of a mis-match may indicate the presence in the test nucleic acid of a mutation. On the other hand, an oligonucleotide probe that has the sequence of a region of the gene including a mutation may be annealed to test nucleic acid and the presence or absence of a mis-match determined. The presence of a mis-match may indicate that the nucleic acid in the test sample has the normal sequence, or a different mutant or allele sequence. In either case, a battery of probes to different regions of the gene may be employed.

The presence of differences in sequence of nucleic acid molecules may be detected by means of restriction enzyme digestion, such as in a method of DNA fingerprinting where the restriction pattern produced when one or more restriction enzymes are used to cut a sample of nucleic acid is compared with the pattern obtained when a sample containing the normal gene or a variant or allele is digested with the same enzyme or enzymes.

The presence of absence of a lesion in a promoter or other regulatory sequence may also be assessed by determining the level of mRNA production by transcription or the level of polypeptide production by translation from the mRNA.

Nucleic acid isolated and/or purified from one or more cells of a plant or a nucleic acid library derived from nucleic acid isolated and/or purified from cells (e.g. a cDNA library derived from mRNA isolated from the cells), may be probed under conditions for selective hybridisation and/or subjected to a specific nucleic acid amplification reaction such as the polymerase chain reaction (PCR).

A method may include hybridisation of one or more (e.g. two) probes or primers to target nucleic acid. Where the nucleic acid is double-stranded DNA, hybridisation will generally be preceded by denaturation to produce single-stranded DNA. The hybridisation may be as part of a PCR procedure, or as part of a probing procedure not involving PCR. An example procedure would be a combination of PCR and low stringency hybridisation. A screening procedure, chosen from the many available to those skilled in the art, is used to identify successful hybridisation events and isolate hybridised nucleic acid.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RNAase cleavage and allele specific oligonucleotide probing.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells.

Preliminary experiments may be performed by hybridising under low stringency conditions various probes to Southern blots of DNA digested with restriction enzymes. Suitable conditions would be achieved when a large number of hybridising fragments were obtained while the background hybridisation was low. Using these conditions nucleic acid libraries, e.g. cDNA libraries representative of expressed sequences, may be searched.

As noted, those skilled in the art are well able to employ suitable conditions of the desired stringency for selective hybridisation, taking into account factors such as oligonucleotide length and base composition, temperature and so on.

In some preferred embodiments of diagnostic assays according to the present invention, oligonucleotides according to the present invention that are fragments of any of the sequences shown in FIG. 8 (SEQ ID NO:2) or FIG. 9 (SEQ ID NO:5), or any allele associated with a desired phenotype are at least about 10 nucleotides in length, more preferably at least about 15 nucleotides in length, more preferably at least about 20 nucleotides in length, more preferably about 30 nucleotides in length. Such fragments themselves individually represent aspects of the present invention.

Fragments and other oligonucleotides may be used as primers or probes as discussed but may also be generated (e.g. by PCR) in methods concerned with determining the presence in a test sample of a sequence indicative of a desired phenotype.

There are various methods for determining the presence or absence in a test sample of a particular polypeptide, such as a polypeptide including the amino acid sequence shown in FIG. 10 (SEQ ID NO:1), or FIG. 11 (SEQ ID NO:3) or FIG. 12 (SEQ ID NO:6), or an amino acid sequence mutant, variant or allele thereof.

A sample may be tested for the presence of a binding partner for a specific binding member such as an antibody (or mixture of antibodies), specific for one or more particular variants of the polypeptide shown in FIG. 10 (SEQ ID NO:1) or FIG. 11 (SEQ ID NO:3) or FIG. 12 (SEQ ID NO:6).

In such cases, the sample may be tested by being contacted with a specific binding member such as an antibody under appropriate conditions for specific binding, before binding is determined, for instance using a reporter system as discussed. Where a panel of antibodies is used, different reporting labels may be employed for each antibody so that binding of each can be determined.

A specific binding member such as an antibody may be used to isolate and/or purify its binding partner polypeptide from a test sample, to allow for sequence and/or biochemical analysis of the polypeptide to determine whether it has the sequence and/or properties of the wild-type polypeptide or a particular mutant, variant or allele thereof. Amino acid sequence is routine in the art using automated sequencing machines.

The use of diagnostic tests for alleles allows the researcher or plant breeder to establish, with full confidence and independent from time consuming biochemical tests, whether or not a desired allele is present in the plant of interest (or a cell thereof), whether the plant is a representative of a collection of other genetically identical plants (e.g. an inbred variety or cultivar) or one individual in a sample of related (e.g. breeders' selection) or unrelated plants.

In a breeding scheme based on selection and selfing of desirable individuals, nucleic acid or polypeptide diagnostics for the desirable allele or alleles in high throughput, low cost assays as provided by this invention, reliable selection for the can be made at early generations and on more material than would otherwise be possible. This gain in reliability of selection plus the time saving by being able to test material earlier and without costly phenotype screening is of considerable value in plant breeding.

Nucleic acid-based determination of the presence or absence of one or more desirable alleles may be combined with determination of the genotype of the flanking linked genomic DNA and other unlinked genomic DNA using established sets of markers such as RFLPs, microsatellites or SSRs, AFLPs, RAPDs etc. This enables the researcher or plant breeder to select for not only the presence of the desirable allele but also for individual plant or families of plants which have the most desirable combinations of linked and unlinked genetic background. Such recombinations of desirable material may occur only rarely within a given segregating breeding population or backcross progeny. Direct assay of the locus as afforded by the present invention allows the researcher to make a stepwise approach to fixing (making homozygous) the desired combination of flanking markers and alleles, by first identifying individuals fixed for one flanking marker and then identifying progeny fixed on the other side of the locus all the time knowing with confidence that the desirable allele is still present.

The present disclosure provides sufficient information for a person skilled in the art to obtain genomic DNA sequence for any given new or existing allele and devise a suitable nucleic acid- and/or polypeptide-based diagnostic assay. In designing a nucleic acid assay account is taken of the distinctive variation in sequence that characterises the particular variant allele.

Nucleic acid according to the invention may include a nucleotide sequence encoding a product involved in glucosinolate biosynthesis, such as whose wild-type function is to catalyse a condensation reaction of (n α-)keto acid with acetyl CoA. Reducing or increasing the level of expression may be used to manipulate glucosinolate biosynthesis in a plant. This may involve use of anti-sense or sense regulation, discussed further below.

Nucleic acid according to the invention, such as an GSL-ELONGASE gene or homologue, may be placed under the control of an externally inducible gene promoter to place expression under the control of the user. An advantage of introduction of a heterologous gene into a plant cell, particularly when the cell is comprised in a plant, is the ability to place expression of the gene under the control of a promoter of choice, in order to be able to influence gene expression, and therefore glucosinolate biosynthesis, according to preference. Furthermore, mutants and derivatives of the wild-type gene, e.g. with higher or lower activity than wild-type, may be used in place of the endogenous gene.

In the present invention, over-expression may be achieved by introduction of the nucleotide sequence in a sense orientation. Thus, the present invention provides a method of influencing a physical characteristic of a plant, the method including causing or allowing expression of the product (polypeptide or nucleic acid transcript) encoded by heterologous nucleic acid according to the invention from that nucleic acid within cells of the plant.

Down-regulation of expression of a target gene may be achieved using anti-sense technology or "sense regulation" ("co-suppression").

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724–726; Zhang et al, (1992) *The Plant Cell* 4, 1575–1588, English et al., (1996) *The Plant Cell* 8, 179–188. Antisense technology is also reviewed in Bourque, (1995), *Plant Science* 105, 125–149, and Flavell, (1994) *PNAS USA* 91, 3490–3496.

An alternative is to use a copy of all or part of the target gene inserted in sense, that is the same, orientation as the target gene, to achieve reduction in expression of the target gene by co-suppression. See, for example, van der Krol et al., (1990) *The Plant Cell* 2, 291–299; Napoli et al., (1990) *The Plant Cell* 2, 279–289; Zhang et al., (1992) *The Plant Cell* 4, 1575–1588, and U.S. Pat. No. 5,231,020.

The complete sequence corresponding to the coding sequence (in reverse orientation for anti-sense) need not be used. For example fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A further possibility is to target a conserved sequence of a gene, e.g. a sequence that is characteristic of one or more genes, such as a regulatory sequence.

The sequence employed may be about 500 nucleotides or less, possibly about 400 nucleotides, about 300 nucleotides, about 200 nucleotides, or about 100 nucleotides. It may be possible to use oligonucleotides of much shorter lengths, 14–23 nucleotides, although longer fragments, and generally even longer than about 500 nucleotides are preferable where possible, such as longer than about 600 nucleotides, than about 700 nucleotides, than about 800 nucleotides, than about 1000 nucleotides or more.

It may be preferable that there is complete sequence identity in the sequence used for down-regulation of expression of a target sequence, and the target sequence, though total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a mutant, derivative, variant or allele, by way of insertion, addition, deletion or substitution of one or more nucleotides, of such a sequence. The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mismatch between the sequence used and the target gene.

Generally, the transcribed nucleic acid may represent a fragment of a gene, such as including a nucleotide sequence shown in FIG. 8 (SEQ ID NO:2) or FIG. 9 (SEQ ID NO:5), or FIG. 12 (SEQ ID NO:6), FIG. 13 (SEQ ID NO:7), FIG. 15 (SEQ ID NO:8) or FIG. 16 (SEQ ID NO:9), or the complement thereof, or may be a mutant, derivative, variant or allele thereof, in similar terms as discussed above in relation to alterations being made to a coding sequence and the homology of the altered sequence. The homology may be sufficient for the transcribed anti-sense RNA to hybridise with nucleic acid within cells of the plant, though irrespective of whether hybridisation takes place the desired effect is down-regulation of gene expression.

Thus, the present invention also provides a method of modifying, affecting, altering or modulating glucosinolate biosynthesis or production a plant, the method including causing or allowing anti-sense transcription from heterologous nucleic acid according to the invention within cells of the plant.

The present invention further provides the use of the nucleotide sequence of FIG. 8 (SEQ ID NO:2) or FIG. 9 (SEQ ID NO:5), or FIG. 12 (SEQ ID NO:6), FIG. 13 (SEQ ID NO:7), FIG. 15 (SEQ ID NO:8) or FIG. 16 (SEQ ID NO:9), or a fragment, mutant, derivative, allele, variant or homologue thereof for down-regulation of gene expression, particularly down-regulation of expression of a GSL-ELONGASE gene or homologue thereof, preferably in order to influence a physical characteristic of a plant, especially glucosinolate content and/or nature.

When additional copies of the target gene are inserted in sense, that is the same, orientation as the target gene, a range of phenotypes is produced which includes individuals where over-expression occurs and some where under-expression of protein from the target gene occurs. When the inserted gene is only part of the endogenous gene the number of under-expressing individuals in the transgenic population increases. The mechanism by which sense regulation occurs, particularly down-regulation, is not well-understood. However, this technique is also well-reported in scientific and patent literature and is used routinely for gene control. See, for example, van der Krol et al., (1990) *The Plant Cell* 2, 291–229; Napoli et al., (1990) *The Plant Cell* 2, 279–289; Zhang et al, 1992 The Plant Cell 4, 1575–1588.

Again, fragments, mutants and so on may be used in similar terms as described above for use in anti-sense regulation.

Thus, the present invention also provides a method of influencing glucosinolate content and/or nature of a plant, the method including causing or allowing expression from nucleic acid according to the invention within cells of the plant. This may be used to suppress activity of a product with ability to influence glucosinolate biosynthesis or production. Here the activity of the product is preferably suppressed as a result of under-expression within the plant cells.

Aspects and embodiments of the present invention will now be illustrated, by way of example, with reference to the accompanying figures. Further aspects and embodiments will be apparent to those skilled in the art. All documents mentioned in this text are incorporated herein by reference.

IN THE FIGURES

FIG. 1 shows a genetic model of glucosinolate biosynthesis in which QTLs and ELONG genes regulate the production of elongated forms of methionine. 2-k-4-mtb is 2-keto-4-methylthiobutanoic acid; 2-k-5-mtp is 2-keto-5-methylthiopentanoic acid; 2-k-6-mth is 2-keto-6-methylthiohexanic acid; 2-k-7-mth is 2-keto-7-methylthioheptanoic acid; 2-k-mp is 2-keto-3- methylpentanoic acid; 2-k-3-mh is 2-keto-3-methylhexanoic acid. The hashed arrow indicates that in the *B.oleracea* mapping population, an additional Mendelian gene regulate the quantitative expression of the GSL.

FIG. 2 shows a biochemical model of glucosinolate biosynthesis, with details of suggested pathway for amino acid chain elongation as supported by biochemical data. The highlighted reaction is the key regulatory step in glucosinolate biosynthesis disclosed herein.

FIG. 3:

Figure 4:
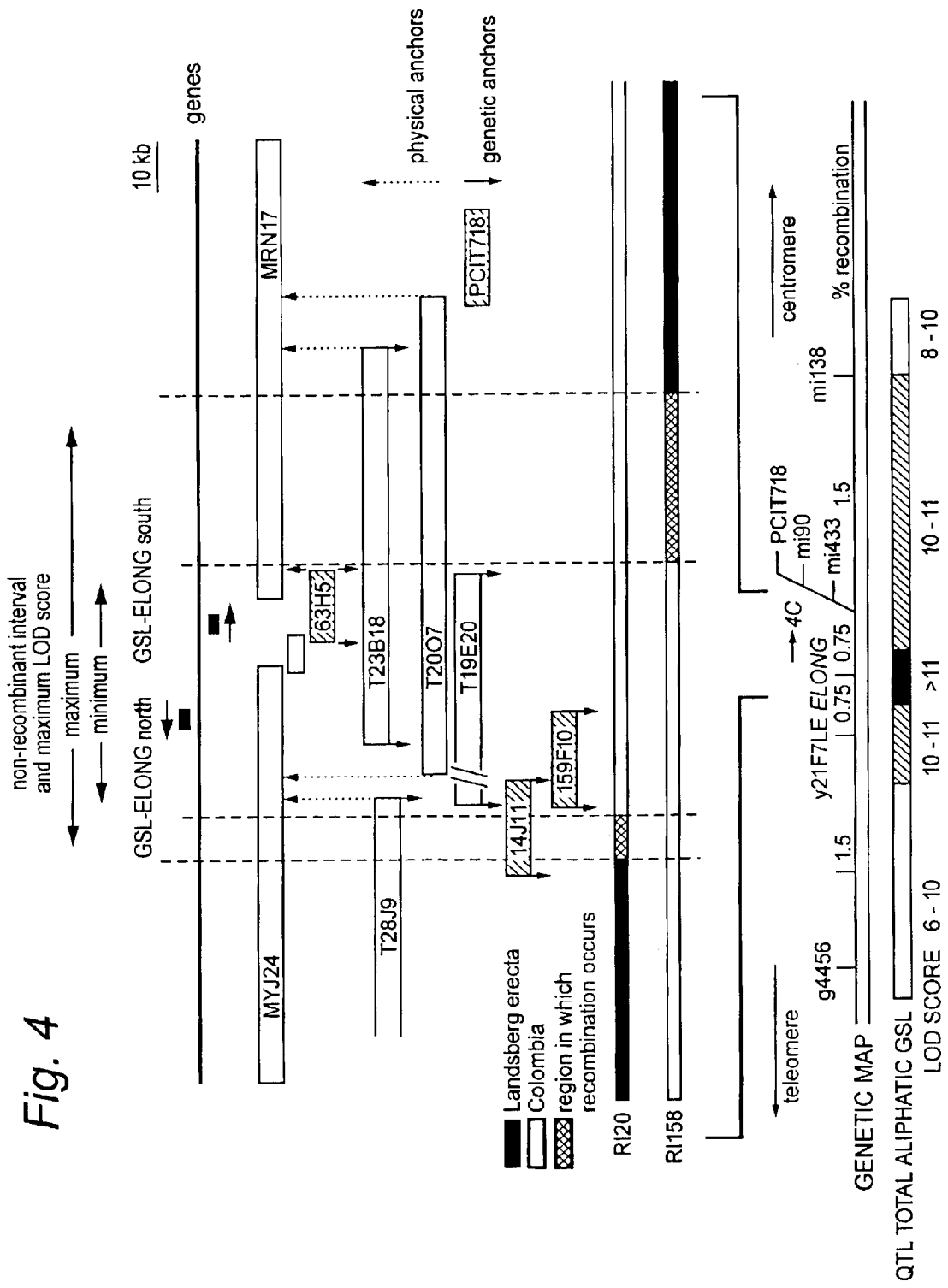

FIG. 4 shows physical mapping in *A.thaliana*. MYJ24 and MRN17 are two sequenced P1 clones. T28J9, T23B18, T2007 and T19E20 are BAC clones from the TAMU library. A, B and C are cosmid clones. The non recombinant region contains two putative genes with keto acid/acetyl CoA domains, one on MYJ24 and one on cosmid A. Both occur on T23B18, T2007 and T19E20.

FIG. 5 shows a comparison of amino acid sequences of soybean late nodulin (o04974) (SEQ ID NO:10), tomato isopropylmate synthetase (Q39891) (SEQ ID NO:11), GSL-ELONGASE NORTH (Aaseq) and *Azotobacter* vinelandii NifV (Q01181) (SEQ ID NO:12), and includes a consensus sequence.

FIG. 6 shows a sequence comparison between genes involved in keto acid/acetyl CoA binding: gsl-elong_s (GSL-ELONG SOUTH); aaseq (GSL-ELONG NORTH); o04974 (Isopropylmalate synthase from tomato) (SEQ ID NO:13); q3891 (Soybean late nodulin) (SEQ ID NO:14); q01181 (Rodobacter sphaeroides NIFV) (SEQ ID NO:15), and includes a consensus sequence.

Figure 7:
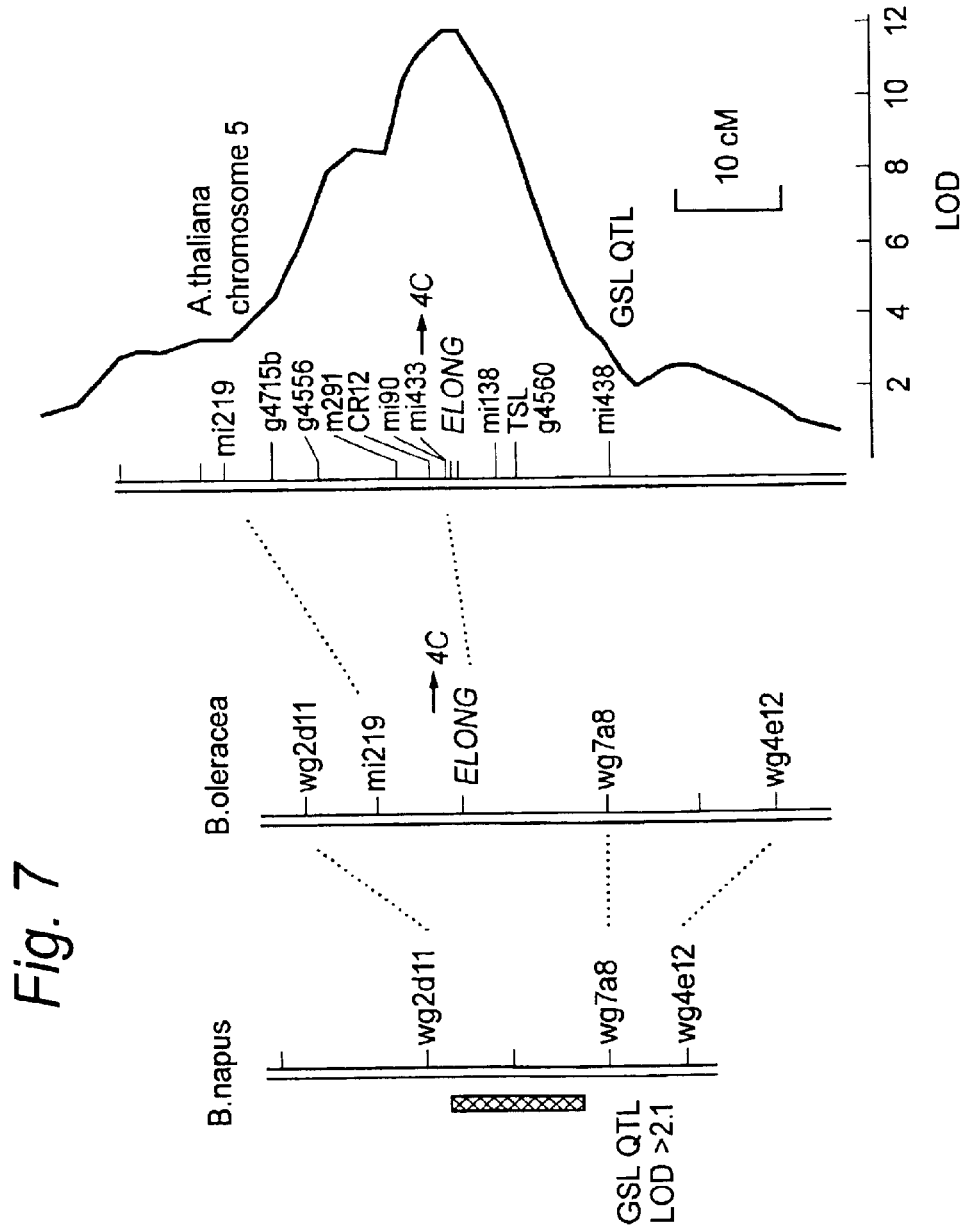

FIG. 7 shows results of comparative mapping between *B.napus*, *B.oleracea* and *A.thaliana*, illustrating synteny between *Arabidopsis* CHR5, *B. oleracea* G2 and *B. napus* G13 in region of GSL-ELONGASE genes.

FIG. 8 (SEQ ID NO:2) shows the identified *Arabidopsis* GSL-ELONGASE NORTH genomic sequence including coding sequence.

FIG. 9 (SEQ ID NO:5) shows predicted *Arabidopsis* GSL-ELONGASE NORTH cDNA sequence.

FIG. 10 (SEQ ID NO:1) shows *Arabidopsis* GSL-ELONGASE NORTH amino acid sequence, also shown in FIG. 5.

FIG. 11 (SEQ ID NO:3) shows *Arabidopsis* GSL-ELONGASE NORTH amino acid sequence, also shown in FIG. 6.

FIG. 12 (SEQ ID NO:6) shows a further *Arabidopsis* GSL-ELONGASE NORTH cDNA sequence, including untranslated leader and coding sequence for the amino acid sequence shown in FIG. 11 (SEQ ID NO:3).

FIG. 13 (SEQ ID NO:7) shows *Arabidopsis* GSL-ELONGASE NORTH genomic sequence, without promoter though including coding sequence for the amino acid sequence shown in FIG. 11 (SEQ ID NO:3).

FIG. 14 (SEQ ID NO:4) shows *Arabidopsis* GSL-ELONGASE SOUTH amino acid sequence, also shown in FIG. 6.

FIG. 15 (SEQ ID NO:8) shows *Arabidopsis* GSL-ELONGASE SOUTH cDNA sequence, including untranslated leader and coding sequence for the amino acid sequence shown in FIG. 14 (SEQ ID NO:4).

FIG. 16 (SEQ ID NO:9) shows *Arabidopsis* GSL-ELONGASE SOUTH genomic sequence, including promoter and coding sequence for the amino acid sequence shown in FIG. 14 (SEQ ID NO:4).

FIG. 17 illustrates enzymic activity of isopropylmalate synthase, homocitrate synthase and suggested activity of products from different ELONG alleles.

Figure 18:
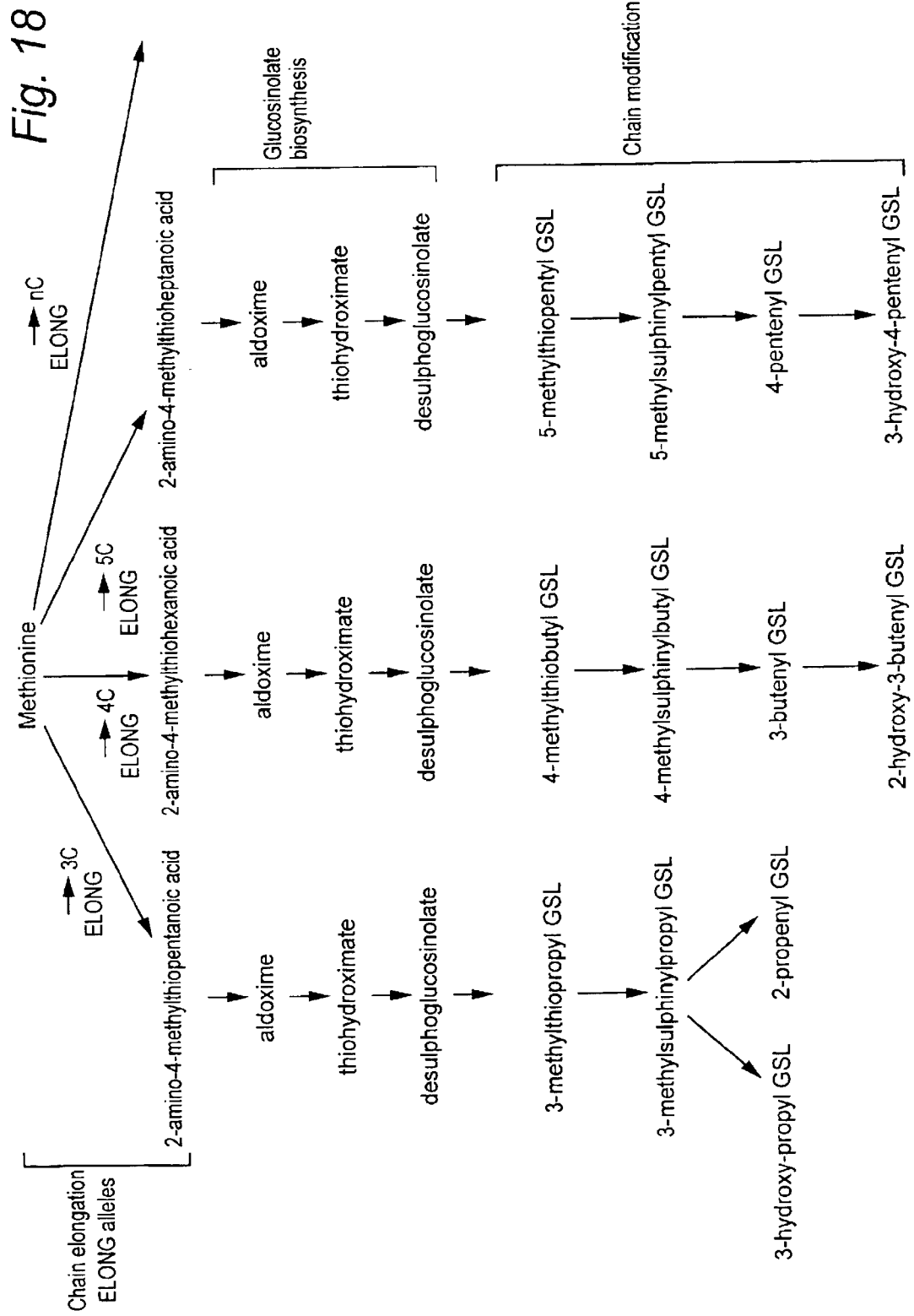

FIG. 18 shows a genetic model of glucosinolate biosynthesis.

Figure 19:
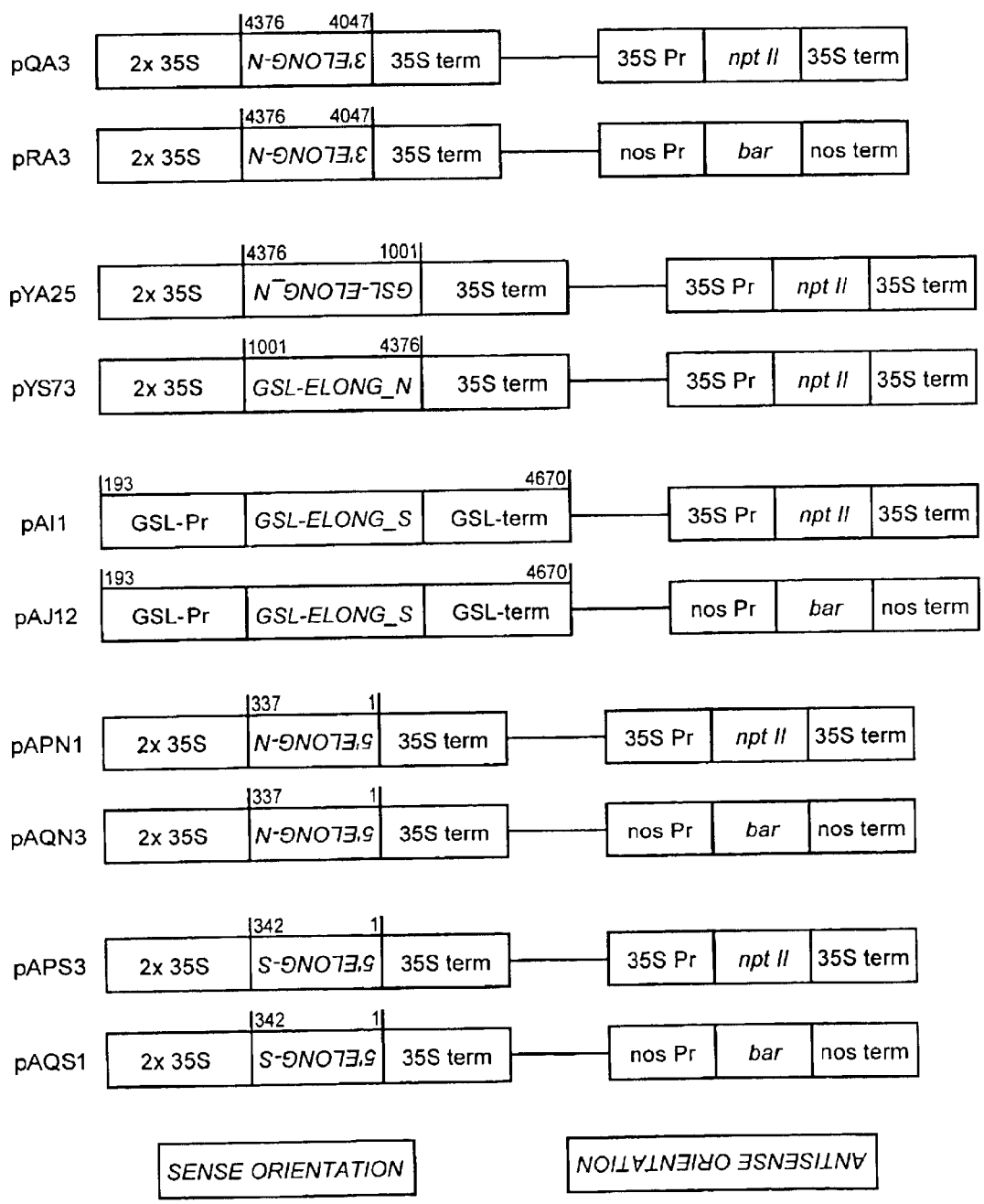

FIG. 19 provides schematic representations of various constructs including sequences of the present invention in sense and antisense orientations. Genomic sequences of GSL ELONG SOUTH and GSL ELONG NORTH were employed.

Genetics of Side Chain Elongation

Genetic Mapping

The Landsberg erecta ecotype of *Arabidopsis thaliana* has predominantly 3-hydroxypropyl glucosinolate in its leaves, while the ecotype Columbia has predominantly 4-methylsulphinylbutyl glucosinolate. The difference is due to alleles at two unlinked loci; GSL-ELONGASE which determines the length of the side chain, and GSL-ALK which determines its side chain structure. To study the genetic basis of this difference, glucosinolates were extracted and analysed from 265 recombinant inbred (RI) lines. 113 RI lines had predominantly 4-methylsulphinylbutyl GSL, while the remaining RI lines had either 3-hydroxypropyl GSL or 3-methylsulphinylpropyl GSL. The approximate 1:1 segregation of side chain lengths indicate that the difference in side chain length is due to segregation of two alleles at a single locus, GSL-ELONGASE. The mapping data was integregated with existing RFLP mapping data from 100 of the RI lines as described by Lister C and Dean C (Plant J (1993) 4 745–750). Additional data was obtained through RFLP mapping with the remaining 165 lines. The GSL-ELONGASE locus was positioned between markers pCIT718 and g21503 (FIG. 3A). There were two recombination events between GSL-ELONGASE and pCIT718, and five recombination events between GSL-ELONGASE and g21503.

Physical Mapping

Schmidt et al (1997) Plant J 11 563–572 provides an outline physical map of *Arabidopsis* chromosome 5 in which YAC clones have been anchored through hybridisation with RFLP markers. Contig 7 contains the YAC clone yUP21F7 situated in the region between the flanking RFLP markers, pCIT718 and g4556. The left end of yUP21F7 was cloned and used as an additional RFLP probes on the RI mapping population. Two recombinants were found between this marker and the GSL-ELONGASE locus indicating that the locus was between this marker and pCIT718 (FIG. 3A). The YAC clone yUP6F5, which hybridises to pCIT718, was then used to select BAC clones from the TAMU BAC library. An overlapping BAC contig was constructed via hybridisation studies. End probes of BAC clones within the contig were cloned and used as RFLP probes to genomic DNA from the RI lines digested with several different restriction enzyme.

Both ends of the clone T19E20 (i.e. T19E20TFB and T19E20TR, see FIG. 3A), the right end of T23B18 (T23B18TR) and the left end of T28J9 (T28J9TFB) cosegregated with the gene.

There was one recombination event between the GSL-ELONGASE locus and the right end of clone T28J9 (T28J9TR) and two recombination events between the GSL-ELONGASE locus and the left end of T28b18 (T23B18TFB, FIGS. 3A and 3B). Thus the gene was located within the BAC contig defined by the three overlapping BACs T23B18, T19E20 and T28J9 (FIG. 3B).

Figure 3:
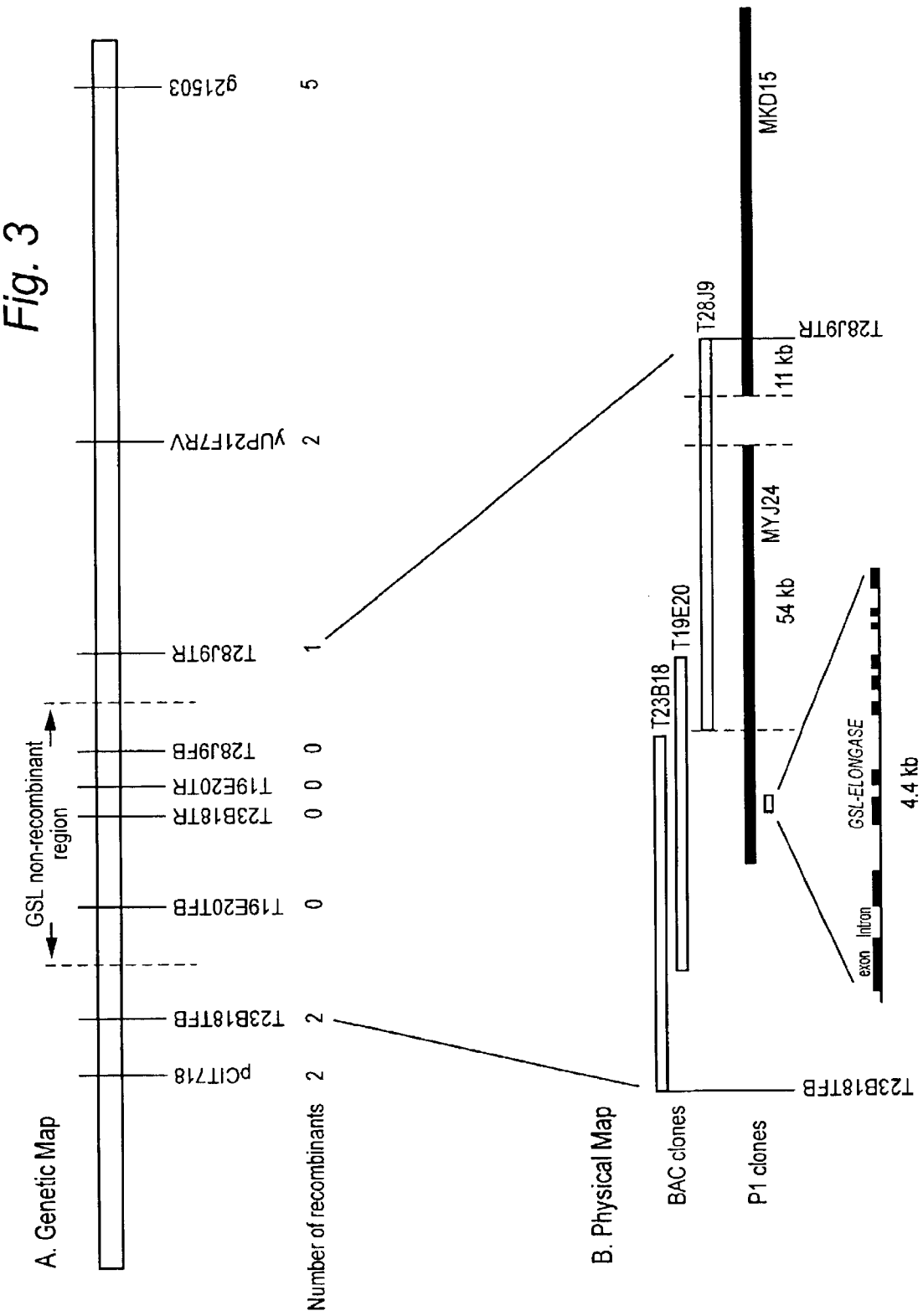
FIG. 3A shows a genetic map of GSL-ELONGASE in *Arabidopsis thaliana*.
FIG. 3B shows a physical map of GSL-ELONGASE in *Arabidopsis thaliana*.

The P1 clone MYJ24 is located on chromosome 5 and hybridises to YAC clone CIC4D, which is also located with the YAC contig 7 as defined by Schmidt (1997) and which contains the BAC clones T28B18, T19E20 and T28J9 kasuza.or.jp/chr5/map/8–10Mb.html. Through the use of the software provided by tigr.org/docs/tigr-ser/al_bac_script/ bac_end_search_spl it was shown that MYJ24 contains the left end sequence of BAC T28J9 and indicates a 54 kb overlap. The right end sequence of T28J9 is found on the P1 clone MKD15, with an overlap of 11 kb. T28J9 was shown to be 70 kb in length resulting in 6 kb of sequence not represented on either MKD15 or MYJ24 (FIG. 3B). Thus a significant part of MYJ24 must be within the GSL-ELONGASE non-recombinant regions (FIG. 3)

Identification of the GSL-ELONGASE Gene kasuza.or.jp/ arabi/chr5/clone/MYJ24/ provides information on gene organisation and putative function of genes on clone MYJ24. The nucleotide and predicted amino acid sequence of a potential gene located between bases 8230 and 11604 has significant homology to a soybean late nodulin cDNA, GmN56 (alignment overlap 448 amino acids, 53% identity, FIG. 5) (Kouchi H and Hata S (1995) Mol Plant Microbe Inter 8 172–176). Further analysis of this region of the P1 clone suggests a gene of 4.9 kb, taking into consideration non-transcribed up-stream and down-stream regions. The predicted amino acid sequence of the *Arabidopsis* gene and the soybean cDNA also has high homology to an isopropylmalate synthase gene of Tomato (EC 4.1.3.12) and several microorganisms, and to NifV (homocitrate synthase) of several nitrogen fixing bacteria (FIG. 5).

Homologies between GSL-ELONGASE and other genes known to catalyse reactions involving acetyl CoA and keto acids

|  | Gene bank accession # | % identity nucleotides | % identity amino acids | % similarities amino acids |
|---|---|---|---|---|
| soybean late nodulin | Q39891 | 41.72 | 53.33 | 73.11 |
| Tomato isopropyl-malate | O04974 | 42.51 | 52.06 | 72.71 |
| Azotobacter NifV | X99902 | 41.45 | 32.16 | 53.51 |

Similarity was calculated using the GAP program of the University of Wisconsin Genetics Computer Group (GCG) programs, employing the parameters in Needleman and Wunsch (journal of Molecular Biology (1970) 48: 443–453). The default parameters used for GAP, BESTFIT and LOCALPILEUP are the same for both GSL-ELONG North and South (see below), as well as for soybean late nodulin, tomato isopropyl malate and *Azotobacter* NifV (gap creation penalty=12; gap extension penalty=4).

These homologies provide indication that the *Arabidopsis* gene encodes an enzyme catalyzing a reaction involving acetyl CoA and α-keto acid as substrates (see for example Kouchi H and Hata S (1995) Mol Plant Microbe Inter 8 172–176; Zheng et al (1997) J. Bacteriology, 179, 5963–5966).

This putative enzyme activity is exactly the predicted activity of the GSL-ELONGASE gene. Thus the combined genetic and biochemical data suggests that this gene is GSL-ELONGASE.

Conserved Regions Between Bacterial and Plant Genes

FIG. 5 shows amino acid conservation between the predicted protein structure of the transcribed regions of the putative GSL-ELONGASE and that from the soybean nodulin, a tomato isopropylmalate synthase and NifV from *Azotobacter vinelandii*. There are three highly conserved regions (underlined). Regions 1 and 2 have been associated with putative binding sites for keto acids based upon comparison with amino acid sequences of pyruvate carboxylase and oxaloacetate decarboxylase which also have binding sites for keto groups (Meijer W and Tabita P (1992) J Bacter 174 3855–3866). Region 3 may therefore be concerned with binding acetyl CoA. These highly conserved regions provide opportunities to isolate additional GSL-ELONGASE alleles and other plant genes which are involved in reactions concerning acetyl CoA and keto acids.

Comparative Mapping Studies.

Several GSL-ELONGASE loci occur in *B.oleracea* and *B.napus*, which possess alleles of different specificities, including an allele which is likely to convert methionine directly to dihomomethionine, the precursor of 4 C glucosinolates (GSL-ELONGASE$^{2C \rightarrow 4C}$) and an allele (GSL-ELONGASE$^{4C \rightarrow 5C}$) which converts dihomomethionine to trihomomethionine (or their respective keto acids). Two GSL-ELONGASE loci have been mapped in *Brassica* (FIG. 7). In *B.oleracea*, a gene on linkage group G2 regulates the conversion of 3C to 4C glucosinolates in a precisely analogous way to the GSL-ELONGASE$^{3C \rightarrow 4C}$ gene in *Arabidopsis*. DNA probes which identified RFLPs near to the GSL-ELONGASE$^{3C \rightarrow 4C}$ gene in *Arabidopsis* also identify RFLPs which are linked to the GSL-ELONGASE$^{3C \rightarrow 4C}$ gene in *B.oleracea*. In *B.napus*, a gene has been mapped on linkage group G13 which converts 4C to 5C glucosinolates, presumably via the condensation of acetyl coA to 2-keto-6-methylthiohexanoic acid. The gene product from the *B.napus* GSL-ELONGASE$^{4C \rightarrow 5C}$ gene thus has a different specificity to that from the *Arabidopsis* and *B.oleracea* GSL-ELONGASE$^{3C \rightarrow 4C}$ gene. The RFLP marker T19E20L cosegregates with the *Arabidopsis* GSL-ELONGASE$^{3C \rightarrow 4C}$ gene and also cosegregates with the *B.napus* GSL-ELONGASE$^{4C \rightarrow 5C}$ gene. The synteny between the *Arabidopsis* and *Brassica* genomes in regions of GSL-ELONGASE genes strongly suggests that the *Brassica* GSL-ELONGASE genes are homologues of the *Arabidopsis* gene and will have a very high degree of similarity at both the nucleotide and amino acid level (average degree of similarity between *Brassica* and *Arabidopsis* gene is 85% at nucleotide level).

Further Comparative Mapping Studies

Comparative genetic studies between *Brassica* and *Arabidopsis thaliana*, identified members of an isopropylmalate synthase-like gene family which catalyse the condensation of keto acids with acetyl CoA as the genes underlying QTLs regulating glucosinolate biosynthesis. These genes regulate the expression of both antinutritional glucosinolates in rapeseed and anticarcinogenic glucosinolates in broccoli via the synthesis of chain elongated homologs of methionine and phenylalanine. This study also illustrates the mechanisms by which novel biochemical diversity in secondary metabolism can rapidly evolve by the recruitment of genes from primary metabolism into existing secondary metabolic pathways.

As noted above glucosinolates (GSLs) are thioglycosides which occur in the Capparales (Rodman et al. (1996) *Systematic Botany* 21, 289–307). The molecule consists of a common glycone moiety and a variable aglycone side chain derived from an amino acid. In the majority of Capparalean families, glucosinolates have aromatic side chains derived from phenylalanine and branched side chains, derived from valine and leucine. However, the predominant glucosinolates in the Brassicaceae possess side chains derived from chain elongated forms of methionine and phenylalanine. Lower amounts of GSLs with indolyl side chains derived from tryptophan also occur. The methionine derived ('aliphatic') GSLs exhibit considerable variation in the length and structure of the side chain (Table 1). Aliphatic GSLs in cruciferous crops are of economic and biological importance, largely as a result of hydrolytic products released upon tissue disruption. For example, the presence of 2-hydroxy-3-butenyl and 2-hydroxy-4-pentenyl GSL in the seeds of Brassica oilseed crops, severely limits the use of rapeseed meal as a high protein animal feed as these two GSLs produce goitrogenic compounds upon ingestion. In contrast, isothiocyanates derived from 3-methylsulfinylpropyl and 4-methylsulfinylbutyl GSLs in broccoli are potent inducers of phase 2 detoxification enzymes which are associated with protection from carcinogens (Zhang et al. (1992). *Proc. Natl. Acad. Sci. USA* 89, 2399–2403). Moreover, many aliphatic GSLs have been implicated in mediating plant-herbivore interactions (Giamoustaris A & Mithen, R. F. (1995) Ann Appl Biol. 126, 347–363).

Biochemical genetic models of aliphatic glucosinolate biosynthesis have suggested three distinct phases: methionine elongation→glucosinolate biosynthesis→side chain modifications. Previous studies in Brassica have shown that while certain side chain modifications of aliphatic GSLs can be attributed to allelic variation at single loci (Giamoustaris A & Mithen R. F. (1996). Theor Appl Genet. 93, 1006–1010.), the amount of aliphatic GSLs is inherited in a quantitative manner regulated by alleles at several QTLs, and that the inheritance of aliphatic and indolyl GSL is independent from each other (Magrath et al. (1993) *Plant Breed.* 111, 55–72). This suggests that the total amount of aliphatic GSL may be regulated by the supply of methionine homologs.

The following describes comparative mapping between Brassica and A. thaliana to identify genomic regions in A. thaliana of interest, followed by physical mapping in A. thaliana to identify a candidate gene family which regulates GSL biosynthesis, and then use DNA probes based upon conserved domains in this gene family to analyse QTLs in economically important Brassica species.

MATERIALS AND METHODS
Comparative Mapping

The position of Mendelian genes which regulate side chain elongation of methionine derived GSLs, and QTLs which regulate the total accumulation of these GSLs were compared among B.napus, B.oleracea and A.thaliana. Results of B.napus QTL mapping have been previously reported (Toroser et al. (1995). *Theor Appl Genet* 91, 802–808.). The B.oleracea mapping population consisted of an $F_2$ population derived from a cross between B.atlantica, a wild form of B.oleracea (von Bothmer et al. (1995) Genet Res Crop Evol 42, 165–178.), and B.oleracea var alboglabra RM2; the B.atlantica parent having >99% 2-propenyl GSL (i.e. 3C side chain), and the B.oleracea parent>95% 3-butenyl and 2-hydroxy-3-butenyl GSL (Mithen et al. (1987). *Phytochemistry* 26, 1969–1973.). DNA from the mapping populations and parents were extracted, restricted with EcoRI, separated by electrophoresis and blotted as described by (Sharpe et al. (1995). *Genome* 38, 1112–1121.). Filters were probed with the 'Osborn' RFLP probes (Ferreira et al. (1994). Theor Appl Genet 89, 615–621.) and a selection of A.thaliana RFLP probes (see below). Linkage analysis was undertaken with the MAPMAKER ver 3.0 software. Glucosinolates were extracted from freeze dried leaf material and analysed as described previously (Magrath et al. (1993) *Plant Breed.* 111, 55–72).

Previous studies had positioned an A.thaliana Mendelian gene (ELONG$^{\rightarrow 4C}$) which regulates side chain length on chromosome 5 (Magrath et al. (1994). *Heredity* 72, 290–299.). To fine map this gene, DNA was extracted from 264 Columbia X Landsberg erecta RI lines, restricted with HindIII, separated by electrophoresis and blotted as described previously (Dean et al. (1992). Plant J 2 69–81.). Filters were probed with A.thaliana RFLP probes, mi219, mi433, mi90, mi138, mi322, mi438, mi291, pCIT718, g21503, g4556, Y21F7LE and CR12, and the Brassica RFLP probes wg2d11, wg7a8 and wg4e12 which flank a major QTL and Mendelian gene regulating GSL in Brassica (Toroser et al. (1995). Theor Appl Genet 91, 802–808).

QTL analysis was undertaken with 60 randomly selected RI lines. Thirty plants of each line were grown in 8.5 cm×8.5 cm pots under standard glasshouse conditions in a standard compost (chemical composition available upon request). Each line and parents were replicated three times and randomised. After six weeks growth, leaf tissue was harvested, freeze dried and glucosinolates analysed by hplc. ANOVA was used to initially analyse QTL data. Threshold values of significance were calculated using bootstrapping procedures as described previously (Wang et al. (1994) Theor Appl Genet 136, 1421–1434; Ray et al. (1996) Theor Appl Genet 92, 627–636). MAPMAKER/QTL software was used to confirm position of QTLs. While this software does not contain an algorithm specifically for RI lines, it has been shown to be sufficently robust to analyse data of this nature (Wang et al. (1994) Theor Appl Genet 136, 1421–1434. and Ray et al. (1996). Theor Appl Genet 92, 627–636) and has been used to map QTLs for trichome number in the same mapping population (Larkin et al. (1996). Development 122, 997–1005.).

Physical Mapping in A. thaliana and Identification of a Candidate Gene Family

The YAC clone yUP6F5 which was located in the region of ELONG$^{\rightarrow 4C}$ was used as a probe into the TAMU BAC library stanford.edu/Arabidopsis/ww/Vol12/choi.html. Manipulation of YAC clones, and library screening was as described previously (Schmidt R & Dean C (1995) Meth. Mol. Cell. Biol. 5, 309–318.). Twenty three clones were selected, assembled into a contig by restriction mapping and orientated through hybridisation to pCIT718. Ends of several of these clones were isolated by iPCR and used as RFLP probes to genomic DNA from RI lines, N4692, N4741, N4665 and N4684, which were shown to have crossovers near to ELONG$^{\rightarrow 4C}$. In order to obtain polymorphisms for mapping, DNA from these lines was restricted with the following enzymes, BamHI, BglII, DraI, EcoRI, EcoRV, HaeIII, HindIII, HincII, HpaII, KpnI, PvuII, RsaI and SacI. End sequences of BACs (http://www.(tigr.org/docs/tigr-ser/al_bac_scripts/bac_end_search_spl) were used to integrate the physical map with sequenced P1 clones (http://(kasuza.org.jp/chr5/map/8–10Mb.html). BACs T19E20 and T23B18 were additionally used as probes into a Columbia cosmid library. Selected cosmids were used as RFLP probes and ends sequenced and integrated with the physical map. DNA sequence from P1 cones was analysed by BLAST and GCG Wisconsin Package version 8 software (with default parameters as indicated above).

Association Between Candidate Gene Family and QTLs in Brassica

For QTL analysis of glucosinolates in Brassica, two novel mapping populations were used. Firstly a B.napus (oilseed rape) population of 75 doubled haploid (DH) lines derived from two $F_1$ individuals from a cross between a homozygous oilseed rape breeding line obtained from Cambridge Plant Breeders-Twyfords Ltd, and the experimental line JICF32. The JIC line was derived by backcrossing a synthetic *B.napus* line four times to oilseed rape cultivars/breeding lines.

The DH lines were grown in replicated field experiments, bagged to prevent cross pollination, and glucosinolates analysed from seeds as described previously (Toroser et al. (1995). Theor Appl Genet 91, 802–808.). Secondly, a *B.oleracea* (broccoli) population of 74 $BC_1$ individuals derived by backcrossing an $F_1$ hybrid between a doubled haploid line derived from the broccoli cultivar Green Duke and B.villosa (another wild member of the *B.oleracea* complex) to the broccoli parent. $BC_1$ plants were grown under standard glasshouse conditions and florets harvested, freeze dried and glucosinolates analysed as described previously. Identification of GSLs in the mapping populations were based upon comparison of retention times with standards. Additional confirmation of structures were obtained by GC-MS analysis of degradation products. Freeze dried leaf tissue was hydrolysed and degradation products extracted with dichloromethane and analysed by GC-MS (Faulkner et al. (1998) *Carcinogenesis* 19(4): 605–609).

DNA from both mapping populations and parents were extracted, restricted with EcoRI, separated by electrophoresis and blotted as described by (Sharpe et al. (1995). *Genome* 38, 1112–1121.). Filters were probed with DNA probes based upon candidate genes identified from the *A.thaliana* physical mapping studies. The distribution of levels of individual GLS segregating in the *B.napus* and *B.oleracea* populations were tested for normality (Anderson-Darling Normality Test), and then for associations between RFLP loci and the quantitative level of glucosinolates using both parametric statistics (single factor ANOVA and two-way ANOVA using the GLM procedure) which assume normality, and non parametric statistics (Kruskal-Wallis), which make no assumptions about distribution of phenotypes. All analyses were undertaken with the Minitab v.10 software.

RESULTS AND DISCUSSION

Comparative Mapping

In an $F_2$ population from a cross between *B.atlantica*, a wild member of the *B.oleracea* n=9 species complex which possessed only 2-propenyl GSL (i.e. a 3C side chain) and *B.oleacea* var *alboglabra*, which possessed 3-butenyl and 2-hydroxy-3-butenyl GSL (i.e. 4C), 55 individuals had >55% 4C GSLs while 17 individuals had <2%. This ratio was not significantly different from a 3:1 ratio indicating the presence of a dominant allele at a single locus determining the presence of 4C GSLs. This locus (ELONG$^{\rightarrow 4C}$-Bo) was positioned between the RFLP markers wg2d11 and wg7a8 (FIG. 7). Two previous and independent studies on QTL mapping of aliphatic GSLs in seeds of oilseed rape had positioned a major QTL between the same flanking markers (Toroser et al. (1995). Theor Appl Genet 91, 802–808 and Uzunova et al. (1995). Theor Appl Genet 90, 194–204.). The major GSL phenotype segregating in these studies was the quantitative level of 2-hydroxy-3-butenyl GSL, i.e. a GSL with a 4C side chain.

This type of qualitative variation in side chain length was also observed in *A. thaliana*. Ecotypes were found to accumulate either predominantly 3C or 4C glucosinolates. For example, the ecotype Columbia accumulates 4-methylsulfinylbutyl GSL (i.e. 4C) while Landsberg erecta accumulates 3-hydroxypropyl (i.e. 3C) (Byrne et al. (1996) Proc Natl. Acad. Sci. USA. 93, 8820–8825.). A previous study positioned a gene which regulates side chain length on chromosome 5 (Byrne et al. (1996) *Proc Natl. Acad. Sci. USA*. 93, 8820–8825.). To map this gene with a higher degree of precision as a prelude to positional cloning, GSLs were analysed in leaf tissue of 264 RI lines derived from a cross between these two ecotypes. 111 lines had 4C GSL (i.e. >70% 4-methylsulfinylbutyl GSL) and 153 lines had 3C GSL [i.e >70% 3-hydroxypropyl GSL or 3-methylsulfinylpropyl GSL depending upon genotypes at the GSL-ALK locus on chromosome 4 (Mithen et al. (1995). *Heredity* 74, 210–215.)]. A single Mendelian locus (ELONG$^{\rightarrow 4C}$-At) was mapped to chromosome 5 which regulates the presence of 4C glucosinolates. This locus was linked to an RFLP locus identified with the probe mi219. This probe also identfied a RFLP locus linked to the putative homologous *B.oleracea* ELONG$^{\rightarrow 4C}$ locus (FIG. 7). Thus, this comparative mapping sudy suggests that the *A. thaliana* ELONG$^{\rightarrow 4C}$ gene may be a homolog of the gene which underlies the *B.napus* QTL, but necessitated the use of *B.oleracea* as a 'bridge' species.

To provide further information on the regulation of GSLs in *A. thaliana*, a QTL mapping study of total aliphatic glucosinolates was undertaken. The aliphatic GSL composition of leaves of Columbia was similar to that previously described (Haughn et al. (1991) Plant Physiol. 97, 217–226.); the major GSL (~70%) was 4-methylsulfinylbutyl GSL, and there were lower amounts of 3-methylsulfinylpropyl GSL, 5-methylsulfinylpentyl GSL, 6-methylsulfinylhexyl GSL and 8-methylsulfinyloctyl GSL. Leaves of Landsberg erecta had predominantly 3-hydroxyprpyl GSL as opposed to 4-methylsulphinylbutyl GSL, but had similar levels of other GSLs as Columbia. The total amount of aliphatic GSLS, regardless of side chain structure, was used for QTL mapping. While there was no significant differences in the total aliphatic GSL content of either Columbia or Landsberg erecta, transgressive variation was observed. Five RI lines had significantly less GSLs than either parent, and five lines had higher levels than either parent (Table 3). Statistical analysis with either single marker analysis or interval mapping revealed the presence of a single major QTL, which explained 57% of the variation in glucosinolate content, and two minor QTLs. At the major QTL, Landsberg erecta alleles resulted in higher levels of GSLs, while at the minor QTLs Columbia alleles resulted in higher levels, thus explaining the genetic basis of trangressive segregation. The major QTL was coincident with the ELONG$^{\rightarrow 4C}$ locus (FIG. 7). Thus studies in both *Brassica* and *A.thaliana* provide indication of an association between quantitative variation in GSL amount and qualitative variation in GSL side chain length. This is consistent with the quantitative regulation of aliphatic GSL expression being determined by the supply of methionine elongated homologs.

Physical Mapping in *Arabidopsis*

A positional cloning approach was employed to elucidate the nature of ELONG$^{\rightarrow 4C}$. The locus was fine mapped with additional RFLP probes and positioned between the cosmid RFLP marker pCIT718 and the YAC end yUP21F7LE. Out of 264 RI lines, there were two recombinants between the locus and pCIT718 (RI lines N4692 and N4741) and two between the locus and yUP21F7LE (N4665 and N4684). YAC clone yUP6F5, which had been positioned adjacent (but not overlapping) to yUP21F7 as part of contig 7 on chromosome 5 (nasc.nott.ac.uk/JIC-contig/chr5_YAC-contig7.GIF), was used as a probe into the TAMU BAC library. Twenty three clones were selected, assembled into a contig and orientated through hybridisation to pCIT718. Ends of several of these clones were isolated by iPCR and used as RFLP probes to genomic DNA from RI lines with recombination events near to the target gene.

Polymorphisms were obtained with the following BAC end probes/enzyme combinations, T23B18LE/XbaI, T19E20RE/HpaII, T19E20LE/DraI, T5K20RE/HpaII, T23B18RE/HincII, T28J9RE/EcoRI, T28J9LE/HincII, T21B12RE/SacI, T14D2RE/BamHI and T14D2LE/EcoRV. Both ends of T19E20 and a single end of each of clones T2007 and T28J9 cosegregated with the phenotype. These results were consistent with the physical map based upon restriction mapping (FIG. 4).

The end sequence of several BACs were used to integrate the physical map to P1 clones which had been sequenced as part of the international *Arabidopsis* genome programme. The non-recombinant interval spanned two clones, MYJ24 and MRN17, and a non sequenced gap between the clones, estimated to be approximately 12 kb. Two cosmids from a Columbia library were selected via hybridsation with BAC T19E20 which were located partially in the interval between the P1 clones. As expected, when these two cosmids were used as probes on to genomic DNA they identifed cosegregating RFLPS. Further cosmids were obtained which helped to delimited the non recombinant regions by mapping and end sequencing. BAC clones T19E20, T21B12 and T28N6 were positioned entirely within the non recombinant regions. Restriction mapping and comparison of physical distances between the ends of these BACs and physical markers revealed that each of these clones had an insert of approximately 60 kb which was not present in the P1 clones, the cosmid library or in genomic DNA from several accessions of Columbia from different sources. These inserts therefore seem to be cloning artifacts.

Identification of a Candidate Gene Family

Figure 2:
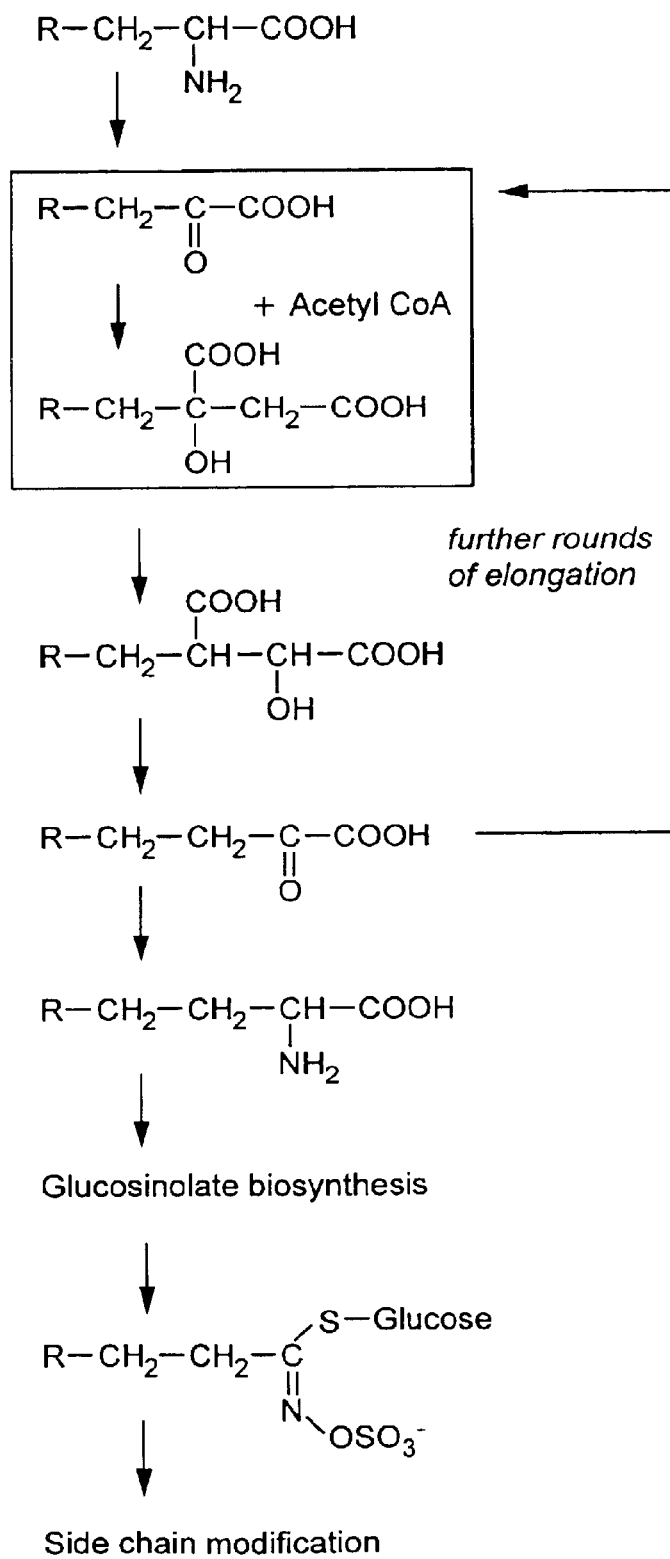

Sequence analysis of the P1 clones within the non-recombinant region revealed the presence of an open reading frame, MYJ24.1 (kasuza.org.jp/arabi/chr5/clone/MYJ24), with high homology to isopropylmalate synthase ('ISPM synthase') and to homocitrate synthase from nitrogen fixing microorganisms (FIG. 6). These two genes catalyse the condensation of a keto acid with acetyl CoA. Furthermore, both genes will accept keto acids of a variety of side chain lengths as substrates (FIG. 17). This activity is the predicted activity of the second step in the derivation of chain elongated GSLs (FIG. 2). Moreover, ISPM synthase is a structural gene which has an additional role in regulating branch chain amino acid biosynthesis (Umbager H E. (1996) in *Escherichia coli* and *Salmonella*: cellular and molecular biology ed Neidhardt F.C. (ASM Press, Washington D.C.) 442–456.).

Sequence comparison of the *A. thaliana* gene and a variety of homocitrate synthase and isopropylmalate synthase genes reveal several regions of high homology. Some of these regions near the 5' end have been associated with binding of the keto group with acetyl CoA (Zheng et al. (1997). *J. Bacter.* 179, 5963–5966 and Stricker et al. (1997). *J. Bacter.* 2930–2937) (FIG. 6). A DNA probe containing the *A. thaliana* coding sequences for the highly conserved domains 1 and 2 of gene MYJ24.1 (FIG. 6) was made via PCR using the primer sequences ATGGTTCTCCGGT-CAGGGTTA (SEQ ID NO:16) and TCTTCGCAC-CCAAATTGGATG (SEQ ID NO:19). This probe is thus diagnostic for genes with keto acid/acetyl CoA binding sites. The probe hybridised to five restriction fragments in *A. thaliana*, three of which cosegregated with ELONG$^{\rightarrow 4C}$. One of these fragments ($\approx$9 kb) was the size predicted from the MYJ24.1 gene, while the other two fragments ($\approx$3.3 and 1 kb) were from a second gene within the non recombinant interval. Fragments the same size was found when the probe was hybridsed to restricted DNA from either of the cosmids spanning the gap between the P1 clones (FIG. 4).

Thus it is likely that there are two genes with keto acid/acetyl CoA binding sites within the non recombinant region. The two genes are designated GSL-ELONG NORTH (syn. MYJ24.1) and GSL-ELONG SOUTH (FIG. 4).

Similarity and identity calculated for the North and South sequences using the GAP program of the University of Wisconsin Genetics Computer Group (GCG) programs, employing the parameters in Needleman and Wunsch (Journal of Molecular Biology (1970) 48: 443–453), with default parameters (gap creation penalty=12; gap extension penalty=4), are 81.437% similarity and 76.647% identity.

To obtain the genomic sequence of GSL-ELONG SOUTH the cosmid 63H5 (FIG. 4) was sequenced. Sequence comparison shows that GSL-ELONG SOUTH has the same conserved domains as ELONG NORTH. The two other RFLP fragments (1.7 and 1.9 kb) were not polymorphic between Columbia and Landsberg erecta. Thus there are either three of four ISPM-synthase like genes in *A.thaliana*, two of which cosegregate with the GSL phenotype and are coincident with the maximum LOD score for the most significant QTL.

To provide further evidence of isopropylmalate synthase homologs in glucosinolate biosynthesis, the DNA probe, diagnostic for keto acid/acetyl CoA binding genes, was hybridised to DNA from novel mapping populations of oilseed rape and broccoli. The *B.napus* population consisted of 76 doubled haploid lines derived from two $F_1$ hybrids between a commercial low glucosinolate rape breeding line ($\approx$16 $\mu$moles g$^{-1}$), and a breeding line with intermediate levels of glucosinolates ($\approx$25 $\mu$moles g$^{-1}$), this latter level being greater than that permitted for Canola quality rapeseed. Three types of chain elongated glucosinolates segregated in the DH lines. Firstly, GSL with 4C side chains (3-butenyl and 2-hydroxy-3-butenyl), secondly, GSL with 5C side chains (4-pentenyl and 2-hydroxy-4-pentenyl) and, lastly, phenylethyl GSL. The 4C GSL were normally distributed while the distributions of 5C GSL and phenylethyl GSL deviated significantly from normality and were skewed towards lower values (Table 4). These two GSL were also significantly correlated with each other ($r^2$=38.8%, p=0.000).

The probe identified 18 fragments, of which 5 were polymorphic. An allelic pair (=2.5 kb and 3.5 kb) was significantly associated with the level of 4C GSLs (p=0.000). Thus, these restriction fragment are likely to contain a gene which catalyses the condensation of acetyl CoA and 2-keto-5-methylthiopentanoic acid ('ELONG$^{\rightarrow 4C}$'). A second allelic pair (=20 kb and 25 kb) was significanlty associated with the levels of both 5C GSLs (p=0.000) and phenylethyl GSL (p=0.000), regardless of whether tested with parametric (ANOVA) or non parametric (Kuskal-Wallis) statistics (Table 4). Therefore it is likely that on this large restriction fragment there are two genes, one catalysing the condensation between acetyl CoA and 2-keto-6-methylhexanoic acid (ELONG$^{\rightarrow 5C}$) to form the precursor of 5C GSL, and a second catalysing the condensation between acetyl CoA and 2-keto-3-phenylethanoic acid (ELONG$^{\rightarrow PNE}$) to form the precursor of phenylethyl GSL. The presence of two genes on a restriction fragment of this size is consistent with the results from physical mapping in *A. thaliana* where two acetyl CoA/keto acid binding genes were found within the non recombinant regions. The results are also consistent with a previous study which suggested an association between a QTL and the presence of 5C GSLs (Toroser et al. (1995). Theor Appl Genet 91, 802–808.).

Figure 1:
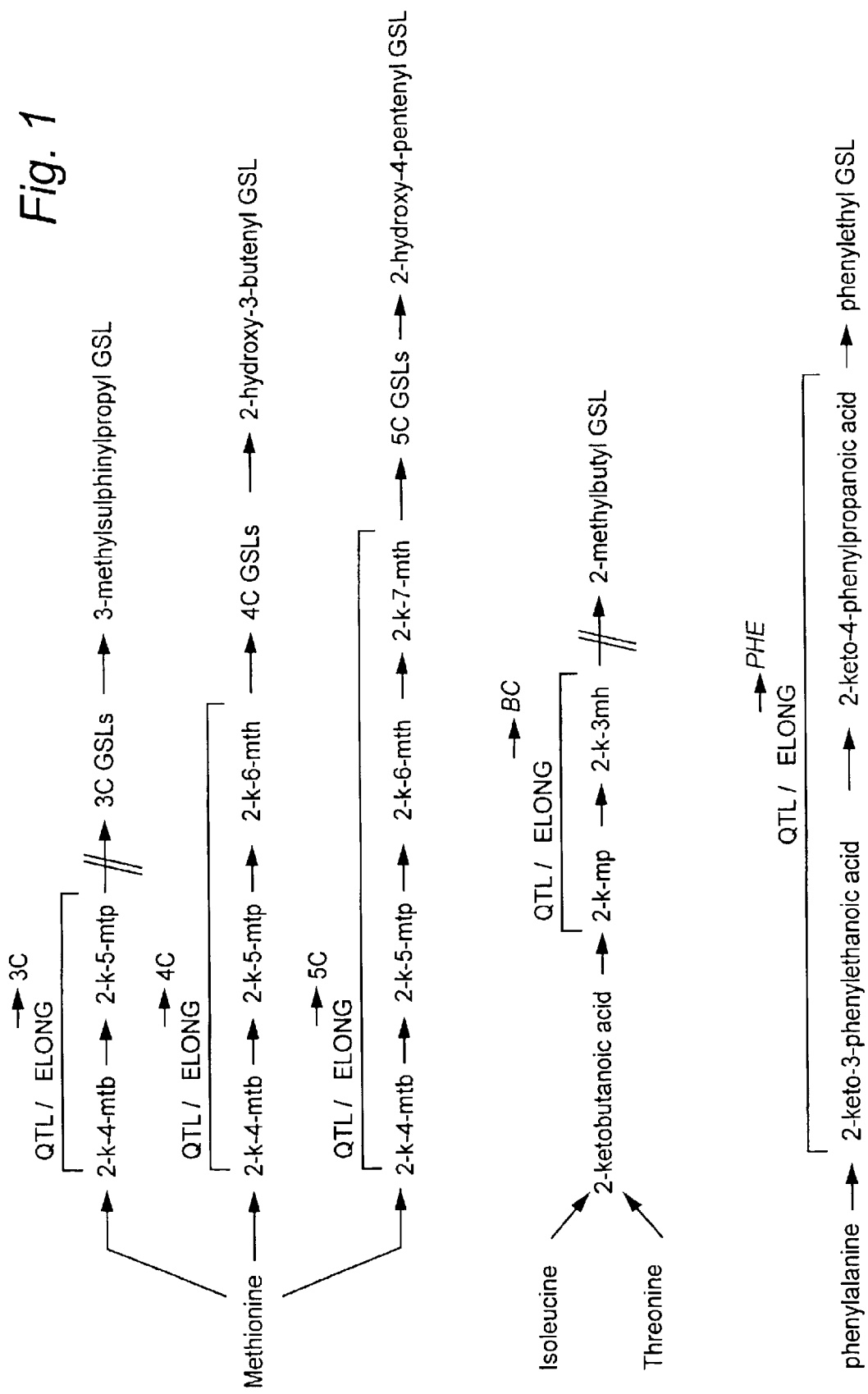

The broccoli population consisted of 74 $BC_1$ lines derived from a cross between the $F_1$ hybrid of a homozygous broccoli breeding line and B.villosa (a wild member of the B.oleracea n=9 complex), and the broccoli parent. In this population there was segregation of two glucosinolates; 3-methylsulphinylpropyl GSL, derived from 2-amino-5-methylthiopentanoic acid, and 2-methylbutyl GSL. This latter GSL is likely to be derived from a chain elongated form of isoleucine (FIG. 1). Both GSL exhibited Mendelian segregation regulated by alleles at two unlinked loci; the presence of a dominant allele from the non recurrent parent at these loci determine the qualitative presence or absence of these GSLS. However, if either GSL was present, there was quantitative variation in the amount. Nine fragments were identified when genomic DNA was hybridised with the diagnostic probe, of which two were polymorphic. One of these (=25 kb) was significantly associated with quantitative variation of both GSLs (Table 4), regardless of whether parametric or non parametric tests were used (Table 3). Hence, there may be a single gene on this DNA restriction fragment which catalyses the condensation of acetyl CoA with 2-keto-4-methylthiobutanoic acid ($ELONG^{\to 3C}$) and 2-keto-3-methylpentanoic acid ($ELONG^{\to BC}$). Alternatively, there may be two or more genes on this DNA fragment with different substrate specificities.

In neither population was there an association between ELONG alleles and non chain elongated glucosinolates. This is consistent with previous reports of the independent inheritance of aliphatic and indolyl GSLs.

DNA probes representing other coding and non-coding sequences in the non-recombinant regions were also made, and used as RFLP probes for the Brassica mapping populations. There were no associations between RFLPs identified with these probes and GSLs in B.oleracea, and GSLs with 4C side chain in B.napus. However, there were significant associations between RFLPs identified with both coding and non coding probes and 5C GSLs in B.napus. This is likely to result from synteny between the respective regions of the B.napus and A.thaliana genomes.

This study has provided evidence for the presence of a complex gene family in Brassicacae which regulates the synthesis of chain elongated GSLs. Different specifities of members of this gene family for methylthioalkyl keto acids of different chain length determine the length of the aliphatic GSL side chain. Allelic variation of alleles with the same keto acid specificities determine the quantitative amount of these GSL, via a mechanism which may involve a negative feed backcontrol as is found with the regulation of leucine biosynthesis by ISPM synthase. This contrast with the regulation of flavanoid biosynthesis in maize in which transcription factors underlie several QTLs (Byrne et al. (1996) Proc Natl. Acad. Sci. USA. 93, 8820–8825.). These GSL ELONG genes can be used in either marker assisted selection or genetic modification programmes to reduce antinutritional GSLs in rapeseed, to enhance anticarcinogenic GSL in horticultural brassicas and to modify plant-herbivore interactions.

Evolution of Biochemical Diveristy

One likely evolutionary scenario for the origin of this gene family is by the duplication of isopropylmalate synthase (a gene required for primary metabolism) and subsequent changes in substrate specificity resulting in the synthesis of chain elongated forms of methionine. These novel amino acids were able to act as substrates for existing enzymes involved in GSL biosynthesis from valine and leucine, thus generating GSLs with novel methylthioalkyl side chains. Interestingly, the isopropylmalate synthase homologs have retained their regulatory role. Subsequent gene recruitment resulted in further modifications to the methylthioalkyl side chain. A similar mechanism of ISPM synthase duplication and mutation is likely to have occurred in order to generate phenylethyl GSL from chain elongated phenylalanine which was able to be used as a substrate for existing GSL biosynthetic enzymes.

Novel biochemical diversity resulting from these processes may have been under positive natural selection pressure by enabling plants to escape from insect herbivores which had become adapted to exisiting GSLs in the ancestors of Brassica and Arabidopsis.

In crucifers, aliphatic glucosinolates are found with side chains up to n=11 (Daxenbichler et al (1991) Phytochemistry 30 2623–2638). Thus it is likely that a large number of alleles of GSL-ELONGASE are present with a different specificities for the chain elongated keto acids. Table 1 illustrates the possible sources of GSL-ELONGASE alleles. PCR primers based upon the highly conserved regions (FIG. 5; FIG. 6) may be used to isolate these alleles.

Chain Elongated Aromatic Glucosinolates

In addition to the different alleles for GSL-ELONGASE for aliphatic glucosinolates, a similar gene may be identified which regulates the chain elongation of phenylethyl glucosinolates. Probes based upon the highly conserved regions may be used to obtain this gene from genomic or cDNA libraries of Brassica, or more preferably watercress (Rorippa nasturtium-aquaticum) which accumulates very high levels of this glucosinolate.

Down-Regulation of GSL-ELONGASE Using Antisense Constructs

Conserved regions of GSL-ELONGASE are amplified using primers as indicated above and the amplified PCR products used to probe to select cDNA clones from Arabidopsis cDNA. Selected clones are sequenced to check homology at the nucleotide level and predicted amino acid sequence of transcribed regions with GSL-ELONGASE.

Full-length and partial length antisense cDNA constructs are produced in which clones containing selected parts of the transcribed nucleotide sequence are engineered into suitable vectors in reverse orientation, driven by a heterologous promoter. Arabidopsis ecotypes Columbia and Landsberg erecta are transformed via Agrobacterium-mediated transformation.

Glucosinolates from the plants are analysed using hplc and found to have altered structures.

Up-Regulation of GSL-ELONGASE Through Addition of Extra Copies and/or Use of a Heterologous Promoter to Achieve Overexpression.

Vectors are constructed containing the full length cDNA or genomic clone in a sense orientation driven by a suitable promoter, either heterologous or, in the case of genomic clones, the endogenous GSL-ELONGASE promoter.

Aradipsis ecotypes are transformed and glucosinolates quantified via hplc.

Additionally, tissue specific promoters are used to change spatial distribution of glucosinolates, and wound inducible promoters are used to achieve overexpression of glucosinolates following damage.

Modification of Glucosinolate Side-Chain Structure

A GSL-ELONGASE allele is introduced into a plant (e.g. Columbia allele introduced into Landsberg).

Glucosinolates are quantified via hplc to check for conversion of 3-hydroxypropyl glucosinolate to 4-methylsulphinylbutyl glucosinolate due to chain elongation.

Obtaining Brassica Alleles and Alleles from Other Species

Probes as discussed containing highly conserved regions obtained via PCR are used to select Brassica GSL-ELONGASE homologues from cDNA and genomic libraries. The above experiments with Arabidopsis are repeated using economically important Brassica species. Longer chain glucosinolate alleles up to C-11 are obtained from species such as shown in Table 1, and these are introduced into economically important Brassica to obtain expression of novel very long chain glucosinolates.

Use of GSL-ELONGASE as a Marker for Marker-Assisted Breeding Programmes

A complete or part of GSL-ELONGASE nucleotide sequence is used as a DNA probe to identify restriction fragment length polymorphisms occurring between plant breeding lines of Brassica and other glucosinolate producing taxa, which possess different GSL-ELONGASE alleles.

Primers are designed to amplify PCR products of different sizes from plant breeding lines containing different alleles. CAPS markers are developed by restricting amplified PCR products.

The markers are used in Brassica breeding programmes aimed at manipulating glucosinolate content of the plants.

Generation and Use of the Vector pGreen for Agrobacterium-Mediated Plant Transformation The pGreen vector system for Agrobacterium-mediated transformation has been developed at the John Innes Centre, Norwich, UK, and derivatives employed as described below for GSL-ELONG transformation of plants to modify glucosinolates therein.

Construction of the pGreen Plasmids

The components of pGreen were constructed as follows:
The pSa Replicon and Construction of pSoup (pJIC Sa Rep)

A 1.7 kb Sau3A partial fragment of pGV1122 (ATCC37171) was cloned into the BamHI site of pJIT134 (Guerineau and Mullineaux, (1993) Plant Mol. Biol. pp. 121–147) and selected for replication in Agrobacterium. The 1.7 kb Sau3A fragment in the resulting plasmid, called pJIT134Sa, was sequenced. Site-directed mutagenesis introduced a BamHI site between the pSa RepA and pSa ori, creating pJIT134SaBam. The 1.2 kb XbaI-BamHI fragment containing the RepA gene was cloned between the BglII sites of pBIN19 (Bevan, (1984) Nucl. Acids Res. 12, 8711–8721; Frisch et al., (1995) Plant Mol. Biol. 27, 405–409) replacing the pBIN19 T-DNA. The NptIII of this pBIN19 derivative was replaced by inserting an EcoRI-StyI fragment, harbouring the tetracycline resistance gene, from pAlter (Promega) between the remaining pBIN19 EcoRV sites to produce pSoup.

pGreen Backbone

The kanamycin resistance gene (NptI) from pACYC177 (Chang and Cohen, (1978) Bacteriol. 134, 1141–1156) was cloned as a NheI-NcoI fragment into the SpeI-BspHI sites of pBluescript SKII+, creating intermediate B. The NcoI site had been introduced into the NptI gene prior to this step and also restriction sites which would have been duplicated in the final pGreen plasmid were removed by site-directed mutagenesis. A unique BglII site was introduced to create intermediate C. The pSa ori sequence was inserted as a BamHI-SmaI fragment from pJIT134Sa-Bam into the BamHI-SmaI sites in intermediate C (remaining from the original pBluescript plasmid). These sites along with an intervening PstI site were removed by successive rounds of treatment with T4 DNA polymerase I (T4 polI) and religations. The StuI site in the NptI promoter and ClaI and NotI sites, introduced when the pSa ori was inserted, were removed by transformation into E. coli strain SCS110 (dam;dcm), digesting with T4 polI and re-ligation. This produced the pGreen backbone which was ready to receive the T-DNA cassette.

T-DNA

A DNA fragment consisting of a StuI site, the RB "overdrive" sequence, the RB sequence and a BglII site, going from 5' to 3' on the sequence, was produced. This RB DNA fragment was inserted into the AflIII site of pBluescript-SKII– and its orientation determined by sequencing. A recombinant plasmid (intermediate A) was selected which had the orientation of the RB fragment such that its StuI site was nearest to the SK multiple cloning site. A LB DNA fragment flanked by a HpaI and BglII site was produced. This fragment was inserted between the two SspI sites of intermediate A, simultaneously deleting the pBluescript SKII-fl ori. This 815 bp BglII fragment was cloned into the pGreen backbone to produce pGreen0000 and 1000 (corresponding to RB-LB and LB-RB orientations). This strategy was also performed on pBluescript KSII–, to produce the T-DNA for pGreen 3000 and 4000.

Construction of Selectable Marker and Reporter Gene Cassettes

The promoter-terminator cassettes into which the selectable marker and reporter gene coding sequences were inserted were constructed as follows. The CaMV35S-CaMV polyadenylation/terminator cassette was based on pJIT61; equivalent to pJIT60 (Guerineau and Mullineaux, (1993) Plant Mol. Biol. pp. 121–147) except that pJIT61 contains a single CAMV 35S enhancer region and multiple cloning site harbouring HindIII, XbaI, BamHI, SmaI, SacI and EcoRI restriction sites in a 5' to 3' order. The KpnI site at the 5' end of the 35S promoter was converted to an EcoRV site. In the same way the BglII site at the 3' end of the CaMV polyadenylation region was converted to an EcoRV site. The plasmid pSLJ261 (Jones et al., (1992) Transgenic Res. 1, 285–297) was the starting plasmid for the construction of the nos promoter-terminator cassette. The internal GUS gene of this plasmid was replaced with a XhoI-XbaI fragment from the pBluescript multiple cloning site. The GUS-deleted pSLJ261 was prepared from the E. coli dam- strain GM2109 and digested with BclI, which was 51 to the nos promoter, and converted to an EcoRV site. In the same way a HindIII site, 3' of the nos terminator, was converted to a second EcoRV site. Both these basic promoter-terminator cassettes were the precursors for all of the CaMV35S and nos selectable marker and reporter gene cassettes.

Restriction sites in the cassettes which would have been duplicated in the pGreen cloning sites were removed by site-directed mutagenesis. More sites were removed after insertion of coding sequences into promoter-terminator cassettes by using T4 DNA polI treatment of DNA cut with the restriction enzyme, followed by religation and selection for loss of the site.

Plant Transformation

Protocols for plant transformation were as follows:

Arabidopsis was transformed with either the root explant method (Valvekens et al., (1989) Proc. Natl. Acad. Sci. USA. 85, 5536–5540) or by vacuum infiltration of developing inflorescences (Bechtold et al., (1993) J. Comptes Rendus Acad. Sci. Paris. 316, 1194–1199) were used as specified.

Cabbage and oil-seed rape were transformed as previously described (Moloney et al., (1989) Plant Cell Rep. 8, 238–242) as was pea (Bean et al., (1997) Plant Cell Rep. 16, 513–519), potato (Edwards et al., (1995) Plant J. 8, 283–294) and tobacco (Guerineau et al., (1990) Plant Mol. Biol. 15, 127–136).

Preparation of plant DNA and associated Southern blotting techniques were employed as described in the quoted papers for these particular species. $P^{12}$-labelled probes were prepared from DNA fragments by a random priming method (Feinberg and Vogelstein, (1983) Anal. Biochem. 132, 6–13).

Materials and In Vitro Cloning Procedures

All in vitro recombination techniques employed were standard (Sambrook et al., (1989) Molecular cloning: A laboratory manual. New York: Cold Spring Harbor Laboratory Press). Site-directed mutagenesis was carried out using the pAlter system (Promega, Wis.) as recommended by the manufacturer. Sequencing was carried out using a dye terminator labelling procedure and employing an ABI 373A Automated Sequencing machine according to the manufacturer's instructions (Applied Biosystems, Foster City Calif.). The sequencing of pGreen is available on the EMBL/Genbank database and on the pGreen website (address given below).

All restriction and DNA modifying enzymes were from Boehringer Mannheim (Lewes, U.K.). All antibiotics were purchased from Sigma (St. Louis, Mo.).

Transformation of Bacteria

*E. coli* (unless otherwise mentioned, strain DH5α) was transformed routinely by the procedure of Hanahan (1983).

Electroporation competent *Agrobacterium* cells were prepared according to (Shen and Forde, (1989) Nucl. Acids Res. 17, 8385) and electroporated in 2 mm cuvettes (BioRad, Hemel Hempstead, U.K.), with the following conditions: 2.5 kV, 400 Ω, 25 μF and 10–100 ng plasmid DNA. The electroporated cells were recovered in Luria broth for 4 h at 28° C. and plated on Luria broth agar plates (Sambrook et al., (1989) Molecular cloning: A laboratory manual. New York: Cold Spring Harbor Laboratory Press) containing kanamycin sulphate (50 μg/ml) and rifampicin (100 μg/ml).

Alternatively, plasmids were transformed into *Agrobacterium* using a freeze-thaw method (An et al., (1988) Plant Mol. Biol. Manual A3, pp 1–19).

Development of the pGreen Vector and the Dual Plasmid System

For replication in *Agrobacterium*, the pSa replication locus has been used in the pGreen vector. This locus is defined by a 1.7 kb Sau3A fragment from the plasmid pGV1122 (ATCC37171). Sequencing of this fragment showed that the pSa replication locus consists of an ori and repA gene. Pilot experiments established that the pSa RepA gene can act in trans on the pSa ori, and was not needed on the pGreen vector, offering a substantial saving on size. Therefore, pSa RepA was subcloned into pBIN19, replacing the T-DNA region. The pBIN19 NptIII gene, coding for bacterial kanamycin resistance, was replaced with the tetracycline resistance gene (tet) from pAlter (Promega), to create pSoup. This plasmid has the RK2 incW replication origin whereas the pSa origin is in the IncR compatibility group, and as such these two plasmids can co-reside in *Agrobacterium*.

The pGreen vector is based on the general cloning vector, pBluescript (Alting-Mees and Short, (1989) Nucl. Acids Res. 17, 9494) and therefore contains a colE1 ori for replication in *E. coli*. This plasmid's ampicillin resistance gene was replaced with the NptI gene (encoding kanamycin resistance), the pSa ori was inserted, the f1 ori and Lac Z' region deleted and a BglII site was left for the introduction of a T-DNA cassette.

The T-DNA cassette, in the case of pGreen0000 is a 813 bp BglII fragment including the pBluescript SKII LacZ gene and multiple cloning site, synthetic LB and RB sequences, derived from the border sequences of PTiT37 and with an additional T-DNA transfer enhancer ("overdrive") motif immediately adjacent and external to the RB (Slightom et al., (1985) *EMBO J.* 4, 3069–3077; Van Haaren et al., (1988) Plant Mol. Biol. 11, 773–781).

Selectable Marker and Reporter Gene Cassettes

The basic pGreen vectors contain no selectable marker or reporter genes for plant transformation. Internal to the T-DNA (LB and RB respectively) are unique HpaI and StuI sites for the insertion of selectable marker or reporter gene cassettes. Four selectable marker genes and two reporter genes have been modified, by site-directed mutagenesis, to remove all the restriction sites which would have been duplicated in the pGreen multiple cloning site. These genes are aph3'II (kan; resistance to kanamycin; Bevan et al., 1983), aphIV (hyp; resistance to hygromycin; Waldron et al., 1985), suII (sul; resistance to sulfonamides and the herbicide asulam; Guerineau et al., 1990), pat (bar; resistance to bialaphos and phosphinothricin; DeBlock et al., 1987), uidA (GUS; Jefferson et al., 1987) and GFP. The aph3'II gene does not contain the mutation that can affect its function as a selectable marker gene in some plant species (Yenofsky et al., (1990) Proc. Natl. Acad. Sci. USA. 87, 3435–3439). The function of all these enzymes has not been affected by the DNA sequence changes introduced. In addition, a synthetic firefly luciferase gene (LUC+) was already available from Promega (Lonsdale et al., (1998) Plant Cell Rep. 17, 396–399) which fulfilled the above criteria. These genes were fused to both (CaMV) 35S promter-19S terminator and nopaline synthase (nos) promoter-terminator and all extraneous sites at cloning junctions were removed. All these gene cassettes are flanked by EcoRV sites which are compatible with both the HpaI and StuI cloning sites of pGreen.

pGreen Nomenclature

Using a computer-generated matrix a number 1 to 728 has been assigned for all the possible 35S and nos-containing cassettes cloned into the LB and/or RB cloning sites of pGreen0000. A KS version of pGreen is available, though not extensively tested and is called pGreen3000. The same designation of marker gene combinations can be assigned to any basic pGreen variant produced in the future. A complete list of the different combinations is available on the pGreen World Wide Web site: intranet.jic.bbscr.ac.uk/INFOSERV/DEPART/appgen/pgreen/A_hom_fr.htm.

Plasmid Handling and Copy Number in *Agrobacterium*

In *Agrobacterium* the pGreen plasmid requires the function of the RepA of pSoup. pGreen contains no mobilisation function (which permitted further savings in size) and so the plasmid is introduced into *Agrobacterium* using either electroporation or freeze-thawing. A mixture of the pGreen plasmid and the pSoup (tetracycline resistant) can be used in a mixed electroporation. In this instance, selection for co-transformed *Agrobacterium* can be achieved by selection on kanamycin-containing medium only, since pGreen cannot replicate in *Agrobacterium* without pSoup being co-resident. Alternatively, electro-competent *Agrobacterium* containing the pSoup can be generated and re-electroporated with pGreen. *A. tumefaciens* strains LBA4404, GV2260, GV3280, AGL-1 and EHA105 and *A. rhizogenes* strain LBA9402 support pGreen replication, provided that pSoup is also present.

Additional Vectors pGreen 0229 pGreen 0229 contained a nos-bar-nos cassette at the left border of the SK T-DNA, LR orientation, in the "+" orientation (see creation of pGreen example). pGreen 0229 was made by digesting pUC119 containing the nos-bar-nos cassette with EcoRV restriction endonuclease. The product was processed further by removing the restriction endonuclease and non-DNA contamination using DNA clean-up columns supplied by Qiagen Corporation using their methodology. Simultaneously, the pGreen 0000 vector was digested with Hpal restriction endonuclease. The products of the two reactions were mixed together forming the cloned DNA molecule, with the assistance of DNA ligase proteins and appropriate substrates (Maniatis et al supra). The product was subsumed into *E. Coli* using the DNA transformation protocol outlined in the published PhD thesis of Roger Hellens "The CHS-1 Genes of Pea", University of East Anglia, 1994. The required clone was identified using conventional molecular biology techniques, and confirmed by sequencing.

pGreen 0104 pGreen 0104 contained a CaMV35S-Kan-CaMV terminator cassette at the left border of the SK T-DNA, LR orientation, in the "−" orientation (see creation of pGreen above). pGreen 0104 was made by digesting the pUC19 derivative plasmid containing the CaMV35S-Kan-CaMV terminator cassette with EcoRV restriction endonuclease. The product was processed further by removing the restriction endonuclease and non-DNA contamination using clean-up columns supplied by Qiagen Corporation using their methodology. Simultaneously, the pGreen 0000 vector was digested with Hpal restriction endonuclease. The products of the two reactions were mixed together forming the cloned DNA molecule with the assistance of DNA ligase proteins and appropriate substrates (Maniatis et al supra). The product was submitted into *E. Coli* using the DNA transformation protocol outlined in Hellens supra. The required clone was identified using conventional molecular biology techniques, and confirmed by sequencing.

pJIT 160

PJIT60 (Guerineau F. et al (1992) Plant Molecular Biology 18, pages 815–818) was treated with restriction enzymes HindIII and Pst1, taking the enzyme restricted DNA and blunt ending with mung bean nuclease for 5 minutes.

The treated DNA was then ligated with a synthetic DNA fragment made from two oligonucleotides, forming pJIT 160. The sequence of the top strand was ACAGCCCAA-CAATGGCG (SEQ ID NO:20).

Genetic Modification of Glucosinolates in Arabidopsis and Brassica

To genetically modify the glucosinolate content in *Arabidopsis* and *Brassica*, constructs were developed in the vector pGreen (described above) and introduced via *Agrobacterium tumefaciens*-mediated transformation. Inserts were based upon sequences of the GSL-ELONG_South and GSL-ELONG_North genes.

Two different types of constructs were made. Firstly, sense constructs containing full length genomic sequences. Secondly, antisense constructs containing either complete or partial genomic sequences in reverse orientation in order to down regulate production of glucosinolates. Constructs either contained the marker gene npt II, for introduction into *Brassica*, or bar for introduction into *Arabidopsis*. Constructs were introduced into *Arabidopsis thaliana* ecotypes Columbia and Landsberg erecta by the method described by Bechtold et al., (1993) (C.R. Acad. Sci. Paris, Sciences de la vie/Life sciences 316: 1194–9). Constructs were introduced into *Brassica napus* var Wetsar by the method of Moloney et al (1989) (Plant Cell Reports 8: 238–242).

GSL-ELONG Construct Design

Generation of pQA3 and pRA3

The 3'-terminus of GSL-ELONG_North was amplified by polymerase chain reaction (PCR) from *Arabidopsis thaliana* ecotype Columbia genomic DNA with the primers: 5'-CAGTGATGAGAAATTCAACGAC-3' (nts. 4047–4068) (SEQ ID NO:21) and 5'-TACAACAGCGGAAATCTGAG-3' (nts. 4376–4357) (SEQ ID NO:22).

The resultant 329 bp (0.3 Kb) fragment was cloned into the vector pGemT-Easy (Promega Corporation) using supplied protocols, producing plasmid pG3. Plasmid pG3 was cut with Eco RI and the 0.3 Kb fragment was cloned into the Eco RI site of plasmid pJIT160 to yield plasmid pH6 with the GSL-ELONG_North fragment in antisense orientation. Plasmid pH6 was digested with Kpn I and Xho I and the 1.9 Kb fragment was cloned into the Kpn I and Xho I sites of; 1, plasmid pGreen 0104 to produce plasmid pQA3; or 2, plasmid pGreen 0229 to produce plasmid pRA3.

Generation of pYA25 and pYS73

The majority of the coding sequence of GSL-ELONG_North was amplified by PCR from *Arabidopsis thaliana* ecotype Columbia genomic DNA with the primers: 5'-ATGGTTCTCCGGTCAGGGTTA-3' (nts. 1001–1021) (SEQ ID NO:16) and 5'-TACAACAGCGGAAATCTGAG-3' (nts. 4376–4357) (SEQ ID NO:22). The resultant 3375 bp (3.3 Kb) fragment was cloned into the vector pGemT-Easy using supplied protocols, producing plasmid pJ4. Plasmid pJ4 was cut with Not I and the 3.3 Kb fragment was cloned into the Not I site of plasmid pSport 1 (Gibco-BRL) to yield; 1, plasmid pM34 with the GSL-ELONG_North fragment in antisense orientation; 2, plasmid pM29 with the GSL-ELONG_North fragment in sense orientation. Plasmid pM34 was digested with Bam HI and Sal I and the 3.3 Kb fragment was cloned into the Bam HI and Sal I sites of plasmid pJIT160 to yield plasmid p2TA5. Plasmid pM29 was digested with Bam HI and Sal I and the 3.3 Kb fragment was cloned into the Bam HI and Sal I sites of plasmid pJIT160 to yield plasmid p2TS1. Plasmid p2TA5 was digested with Sal I and the 4.9 Kb fragment was cloned into the Sal I site of plasmid pQA3 to yield plasmid pYA25. Plasmid p2TS1 was digested with Sal I and the 4.9 Kb fragment was cloned into the Sal I site of plasmid QA3 to yield plasmid pYS73.

Generation of pAI1 and pAJ12

The genomic copy of GSL-ELONG_South from *Arabidopsis thaliana* ecotype Columbia is found on cosmid 63H5. There are Cla I restriction sites at nt. 193 within GSL-ELONG_South and 2075 nts. 3' of the GSL-ELONG_South gene. Cosmid 63H5 was digested with Cla I and the 6.5 kb Cla I fragment was cloned into the Cla I site of; 1 plasmid pGreen 0104 to produce plasmid pAI1; or 2, plasmid pGreen 0229 to produce plasmid pAJ12.

Generation of pAPN1 and pAQN3

A clone of GSL-ELONG_North cDNA in vector pCR2.1-TOPO (Invitrogen), pJ3 (Max Plank Institute of Chemical Ecology) was digested with Eco RI and Hind III. There is an Eco RI site in the vector 26 bp 5 of the cDNA insert and a Hind III site at nt. 311 within the cDNA insert. The resultant 337 bp (0.3 Kb) Eco RI-Hind III fragment was cloned into the Eco RI and Hind III sites of pBluescript II SK+ (Stratagene) to yield plasmid pAL1. Plasmid pAL1 was digested with Eco RI and Sal I and the resultant 0.3 Kb fragment was cloned into the Eco RI and Sal I sites of pJIT160 to yield plasmid pAN1. Plasmid pAN1 was digested with Kpn I and Xho I and the 1.9 Kb fragment was cloned into the Kpn I and Xho I sites of; 1, plasmid pGreen 0104 to produce plasmid pAPN1; or 2, plasmid pGreen 0229 to produce plasmid pAQN3.

Generation of pAPS3 and pAQS1

A clone of GSL-ELONG_South cDNA in vector pCR2.1-TOPO (Invitrogen), p10a (Max Plank Institute of Chemical Ecology) was digested with Eco RI and Hind III. There is an Eco RI site in the vector 27 bp 5' of the cDNA insert and a Hind III site at nt. 315 within the cDNA insert. The resultant 342 bp (0.3 Kb) Eco RI-Hind III fragment was cloned into the Eco RI and Hind III sites of pBluescript II SK+ (Stratagene) to yield plasmid pAM1. Plasmid pAM1 was digested with Eco RI and Sal I and the resultant 0.3 Kb fragment was cloned into the Eco RI and Sal I sites of pJIT160 to yield plasmid pAO1. Plasmid pAO1 was digested with Kpn I and Xho I and the 1.9 Kb fragment was cloned into the Kpn I and Xho I sites of; 1, plasmid pGreen 0104 to produce plasmid pAPS3; or 2, plasmid pGreen 0229 to produce plasmid pAQS1.

Mobilisation of pGreen-Based Constructs into *Agrobacterium tumefaciens*

Preparation of Competent *Agrobacterium tumefaciens* Cells

Two strains of *A. tumefaciens* were used in plant transformation; strain GV3101 (Koncz and Schell (1986) *J. Mol. Gen. Genet.* 204: 383–396) for *Arabidopsis thaliana* transformation and strain LBA4404 (John Innes Centre) for *Brassica oleracea* and *B. napus* transformation. *A. tumefaciens* was grown in Luria Broth (Sambrook et al., 1989) supplemented with rifampicillin (50 $\mu$g/ml) at 28° C. with shaking for 48 hours. Cells were harvested at 2000×g for ten minutes at 4° C. Cells were washed three times in 0.5 volumes of sterile 10% glycerol. Cells were resuspended in 0.01 volumes of sterile 10% glycerol, incubated at 4° C. for two hours, divided into 401 aliquots and stored at −80° C.

Electroporation of Competent *A. tumefaciens* Cells

Electroporation experiments were carried out using a Cell-Porator and supplied cuvettes (Gibco-BRL). Competent *A. tumefaciens* cells were thawed at 4° C. To 20 $\mu$l aliquots of cells was added, 50 ng pGreen-based plasmid and 50 ng pJIC Sa_Rep. The cells were placed in a pre-chilled electroporation cuvette and cells were electroporated under the following conditions; 330 mF, voltage boost 4 KW, charge rate fast, low W, 405V and 2.3 ms pulse time.

Following electroporation 200 ml Luria Broth was added to the cells. Cells were allowed to recover for one hour at room temperature and then spread on plates of selective media (Luria Broth amended with rifampicillin 50 mg/ml and kanamycin 50 mg/ml). Plates were incubated at 28° C. for 48 hours.

RESULTS

Results were obtained by analysis of the inflorescence of transgenic plants of Landsberg erecta (Ler) containing the RA3 constructs. This construct contains a non-conserved part of the 3' end of ELONG NORTH. More than 95% of the glucosinolates in the inflorescence of wild type Ler is 3-hydroxypropyl glucosinolate.

3-hydroxypropyl GSL $\mu$mol g$^{-1}$ dry weight

| Ler (wild type) | 10.2 ± 1.03 | (mean ± sd, n = 3) |
| Ler + RA3 | 5.6 | (n = 1) |

These results indicated in the transgenic Ler there is a significant reduction of 3-hydroxypropyl glucosinolates ($p<0.01$).

TABLE 1

Possible sources of novel alleles of GSL-ELONGASE for different length side chains.

| Taxa | →3C | →4C | →5C | →6C | →7C | →8C | →9C | →10C | →11C |
|---|---|---|---|---|---|---|---|---|---|
| A. thaliana | + | + | | | | | | | |
| B. oleracea | + | + | | | | | | | |
| B. rapa | | + | + | | | | | | |
| B. napus | | + | + | | | | | | |
| Alyssum argenteum | | + | + | | | | | | |
| Hesperis matronalis | | | + | + | | | | | |
| Lepidium ovalifolia | | | | | + | | | | |
| Sibaria spp | | | | | + | + | | | |
| Arabis glabra | | | | | + | + | | | |
| Arabis hirsuta | | | | | | + | + | | |
| Biscutella auriculata | | | | | | + | + | | |
| Arabis alipina | | | | | | | + | + | |
| Arabis turrita | | | | | | | + | + | |
| Camelina spp | | | | | | | | + | + |

TABLE 2

Chain elongated glucosinolates found in *Brassicaceae*.

| From methionine | | |
|---|---|---|
| Methylthioalkyl | $CH_3-S-CH_2-CH_2-[CH_2]_n-GSL$ | n = 1–8 |
| Methylsulphinyl-alkyl | $CH_3-SO-CH_2-CH_2-[CH_2]_n-GSL$ | n = 1–9 |
| Alkenyl | $CH_2=CH-[CH_2]_n-GSL$ | n = 1, 2, 3 |
| 2-Hydroxy-3-butenyl | $CH_2=CH-\underset{\underset{OH}{\mid}}{CH}-CH_2-GSL$ | |
| 2-Hydroxy-4-pentenyl | $CH_2=CH-CH_2-\underset{\underset{OH}{\mid}}{CH}-CH_2-GSL$ | |
| Hydroxyalkyl | $\underset{\underset{OH}{\mid}}{CH_2}-CH_2-[CH_2]_n-GSL$ | n = 1, 2 |

TABLE 2-continued

Chain elongated glucosinolates found in Brassicaceae.

From phenylalanine  n = 1, 2, 3

From branch chain amino acids

Isobutyl 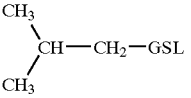

2-Methylbutyl 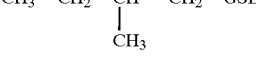

TABLE 3

Aliphatic glucosinolate content of Columbia and Landsberg erecta and high and low transgressive Rl lines, and genotype at RFLP markers linked to QTLs. LOD scores > 2.1 are usually considered to be of biological significance.

| | Total aliphatic GSLs mean = SE | QTL-1/CHR5 LOD 11.4 p < 0.000* mi433 | QTL-2/ CHR1 LOD 2.6 p < 0.01 g4026 | QTL-3/CHR4 LOD 1.3 p < 0.01 m506 |
|---|---|---|---|---|
| Columbia | 21.0 ± 3.40 | C | C | C |
| Landsberg | 20.4 ± 2.82 | L | L | L |
| erecta | | | | |
| High transgressives | | | | |
| 113 | 34.6 ± 5.96 | L | C | C |
| 177 | 30.2 ± 3.78 | L | C | C |
| 179 | 31.1 ± 0.88 | L | C | C |
| 209 | 31.0 ± 0.50 | L | C | C |
| 235 | 28.9 ± 2.95 | L | C | L |
| Low transgressives | | | | |
| 13 | 8.1 ± 1.22 | C | L | C |
| 194 | 12.0 ± 0.56 | C | L | L |
| 237 | 10.8 ± 1.44 | C | L | L |
| 264 | 9.9 ± 0.72 | C | L | L |
| 390 | 10.6 ± 2.03 | C | L | C |

*p values calculated from single marker analysis at closest RFLP locus

TABLE 4

Quantitative association between glucosinolates and ELONG genes. For each locus, D11 lines and BC, individuals can be divided into two genotypic classes based upon possessing one of two restriction fragments designated the + allele (ie increasing GSL content) and the − allela (decreasing GSL content).

| | | | ANOVA | | | | Kruskal-Wallis | | | | |
|---|---|---|---|---|---|---|---|---|---|---|---|
| | | | mean ± se $\mu$mol g$^{-1}$ | | | | median $\mu$mol g$^{-1}$ | | | | |
| Glucosinolate | locus* | p(normal)$^\phi$ | − allele | + allela | F | P | − allela | + allele | H | P | r$^2$% |
| Oilseed rape seeds | | | | | | | | | | | |
| 3-butenyl + 2-hydroxy-3-butenyl | E-N6 | 0.263 | 16.9 ± 0.58 | 20.0 ± 0.42 | 19.6 | 0.000 | 16.6 | 20.0 | 16.3 | 0.000 | 21.2 |
| 4-pentanyl + 2-hydroxy-4-pentenyl | E-N1 | 0.000 | 0.51 ± 0.08 | 2.2 ± 0.23 | 51.5 | 0.000 | 0.36 | 1.76 | 38.1 | 0.000 | 41.1 |
| phenylethyl | E-N1 | 0.000 | 0.22 ± 0.021 | 0.41 ± 0.049 | 14.2 | 0.000 | 0.21 | 0.34 | 18.5 | 0.000 | 16.1 |
| Broccoli florets | | | | | | | | | | | |
| 3-methylsulphinylpropyl | E-O1 | 0.067 | 9.3 ± 1.07 | 17.7 ± 1.71 | 15.8 | 0.001 | 8.85 | 17.6 | 1.3 | 0.001 | 41.7 |
| 2-methylbutyl | E-O1 | 0.048 | 3.1 ± 0.31 | 6.3 ± 0.46 | 15.0 | 0.001 | 2.53 | 4.62 | 8.6 | 0.004 | 24.6 |

*RFLP locus identfied with the diagnostic DNA probe.
$^\phi$probability of normal distribution (Anderson-Darling test).

What is claimed is:

1. An isolated polynucleotide encoding a polypeptide which catalyses a condensation reaction of a 1n α-keto acid with acetyl CoA, which polypeptide includes an amino acid sequence which has at least 90% amino acid sequence identity with the full-length amino acid sequence shown in SEQ D NO:1.

2. The isolated polynucleotide of claim 1, wherein said polynucleotide is operably linked to a regulatory sequence for expression.

3. An isolated polynucleotide which is fully complementary to the sequence of nucleotides 4047 to 4376 of SEQ ID NO:2
    wherein said polynucleotide is suitable for use in antisense regulation of expression of said coding sequence and under control of a regulatory sequence for transcription.

4. A nucleic acid vector suitable for transformation of a plant cell and including the polynucleotide according to claim 1.

5. A host cell containing a polynucleotide according to claim 1, wherein said polynucleotide is heterologous to said host cell.

6. The host cell according to claim 5 which is microbial.

7. The host cell according to claim 5 which is a plant cell.

8. The plant cell according to claim 7 having said heterologous polynucleotide within its chromosome.

9. The plant cell according to claim 8 having more than one copy of said polynucleotide per haploid genome.

10. A method of producing the cell according to claim 5, the method including incorporating said polynucleotide into the cell by means of transformation.

11. The method according to claim 10 which includes recombining the polynucleotide with the cell genome nucleic acid such that it is stably incorporated there.

12. The method according to claim 10 which includes regenerating a plant from one or more transformed cells.

13. A plant comprising the plant cell according to claim 7.

14. A part or propagule of a plant comprising the plant cell according to claim 7.

15. A method of producing a plant, the method comprising incorporating the polynucleotide according to claim 1 into a plant cell and regenerating a plant from said plant cell.

16. The method according to claim 15 including sexually or asexually propagating or growing off-spring or a descendant of the plant regenerated from said plant cell, said off-spring or descendent comprising said polynucleotide.

17. A method of decreasing the level of 3 C glucosinolates in a plant, the method comprising expressing the polynucleotide from the vector according to claim 4 within cells of the plant, thereby decreasing the level of 3 C glucosinolates.

* * * * *